United States Patent
Ghiron

(12) 
(10) Patent No.: US 11,000,693 B2
(45) Date of Patent: May 11, 2021

(54) MAGNETIC STIMULATION COILS AND FERROMAGNETIC COMPONENTS FOR TREATMENT AND DIAGNOSTIC PROCEDURES

(71) Applicant: Neuronetics, Inc., Malvern, PA (US)

(72) Inventor: Kenneth Marc Ghiron, Malvern, PA (US)

(73) Assignee: Neuronetics, Inc., Malvern, PA (US)

(*) Notice: Subject to any disclaimer, the term of this patent is extended or adjusted under 35 U.S.C. 154(b) by 446 days.

(21) Appl. No.: 15/900,477

(22) Filed: Feb. 20, 2018

(65) Prior Publication Data

US 2019/0255346 A1 Aug. 22, 2019

(51) Int. Cl.
| | | |
|---|---|---|
| *A61N 2/02* | (2006.01) | |
| *A61N 2/00* | (2006.01) | |
| *H01F 1/153* | (2006.01) | |
| *H01F 7/06* | (2006.01) | |
| *H01F 7/20* | (2006.01) | |
| *H01F 27/28* | (2006.01) | |
| *H01F 27/255* | (2006.01) | |

(52) U.S. Cl.
CPC ............ *A61N 2/02* (2013.01); *A61N 2/006* (2013.01); *H01F 1/15325* (2013.01); *H01F 7/064* (2013.01); *H01F 7/20* (2013.01); *H01F 27/255* (2013.01); *H01F 27/28* (2013.01)

(58) Field of Classification Search
CPC .................................. A61N 2/006; A61N 2/02
See application file for complete search history.

(56) References Cited

U.S. PATENT DOCUMENTS

| 4,985,089 A | 1/1991 | Yoshizawa et al. |
| 6,179,771 B1 | 1/2001 | Mueller |
| (Continued) | | |

FOREIGN PATENT DOCUMENTS

| CN | 102727997 A | 10/2012 |
| WO | WO 2008-070001 A2 | 6/2008 |

OTHER PUBLICATIONS

Aron Tendler, Noam Barnea Ygael, Yiftach Roth & Abraham Zangen (2016) Deep transcranial magnetic stimulation (dTMS)—beyond depression, Expert Review of Medical Devices, 13:10, 987-1000.

(Continued)

*Primary Examiner* — Christine H Matthews
(74) *Attorney, Agent, or Firm* — Flaster Greenberg, P.C.

(57) ABSTRACT

An example system may include an electromagnet, a drive circuit electrically coupled to the electromagnet, and a controller configured to control the drive circuit to provide current to the electromagnet to generate a pulsing magnetic field. The electromagnet may include a first conductive winding, a second conductive winding, and a magnetic core. The first conductive winding may be crescent shaped. The first conductive winding may define an inner surface and an outer surface. The outer surface of the first conductive winding may include a convex portion and a concave portion. The second conductive winding may reside proximate to the concave portion of the outer surface of the first conductive winding. The outer concave segment of the first conductive winding may define a concavity, and at least a portion of the second conductive winding may reside within the concavity of the first conductive winding.

29 Claims, 17 Drawing Sheets

(56) References Cited

U.S. PATENT DOCUMENTS

| | | | |
|---|---|---|---|
| 6,425,852 B1 | 7/2002 | Epstein et al. | |
| 6,500,110 B1 | 12/2002 | Davey et al. | |
| 6,527,695 B1 | 3/2003 | Davey et al. | |
| 6,663,556 B2 | 12/2003 | Barker | |
| 6,827,681 B2 | 12/2004 | Tanner et al. | |
| 7,008,370 B2 | 3/2006 | Tanner et al. | |
| 7,087,008 B2 | 8/2006 | Fox et al. | |
| 7,239,910 B2 | 6/2007 | Tanner | |
| 7,407,478 B2 | 8/2008 | Zangen et al. | |
| 7,520,848 B2 | 4/2009 | Schneider et al. | |
| 7,591,776 B2 | 9/2009 | Phillips et al. | |
| 7,854,232 B2 | 12/2010 | Aho et al. | |
| 7,857,746 B2 | 12/2010 | Riehl | |
| 7,998,053 B2 | 8/2011 | Aho | |
| 8,267,850 B2 | 9/2012 | Schneider et al. | |
| 8,777,831 B2 | 7/2014 | Aho | |
| 8,845,508 B2 * | 9/2014 | Schneider | A61N 2/006 600/14 |
| 8,956,274 B2 | 2/2015 | Schneider et al. | |
| 9,533,168 B2 | 1/2017 | Zangen et al. | |
| 9,675,815 B1 | 6/2017 | Fischell et al. | |
| 9,724,533 B1 | 8/2017 | Fischell et al. | |
| 9,744,373 B2 | 8/2017 | Hernandez-Garcia et al. | |
| 9,802,058 B2 | 10/2017 | Zangen et al. | |
| 9,808,642 B2 | 11/2017 | Zangen et al. | |
| 2001/0031906 A1 | 10/2001 | Ishikawa et al. | |
| 2002/0097125 A1 | 7/2002 | Davey | |
| 2006/0019992 A1 | 1/2006 | Wu et al. | |
| 2006/0094924 A1 | 5/2006 | Riehl | |
| 2007/0260107 A1 | 11/2007 | Mishelevich et al. | |
| 2008/0058581 A1 | 3/2008 | Aho | |
| 2008/0058582 A1 | 3/2008 | Aho et al. | |
| 2010/0286470 A1 | 11/2010 | Schneider et al. | |
| 2011/0015464 A1 | 1/2011 | Riehl et al. | |
| 2011/0039700 A1 | 2/2011 | Fischer | |
| 2011/0125203 A1 | 5/2011 | Simon et al. | |
| 2014/0235926 A1 | 8/2014 | Zangen et al. | |
| 2014/0235928 A1 | 8/2014 | Zangen et al. | |
| 2014/0276182 A1 | 9/2014 | Helekar et al. | |
| 2015/0165226 A1 | 6/2015 | Simon et al. | |
| 2016/0346562 A1 | 12/2016 | Saitoh et al. | |

OTHER PUBLICATIONS

Zhi-De Deng, Sarah H. Lisanby, Angel V. Peterchev. Electric field depth-focality tradeoff in transcranial magnetic stimulation: Simulation comparison of 50 coil designs. 2013 Elsevier Inc. www.brainstimjrnl.com.

Zhi-De Deng, Sarah H. Lisanby, Angel V. Peterchev. Electric field depth-focality tradeoff in transcranial magnetic stimulation: Simulation comparison of 50 coil designs. NIH Public Access. Brain Stimul. Author manuscript; available in PMC Feb. 9, 2013.

CN 102727997 A, 45, Cited in International Search Report dated Jun. 7, 2018.

Davey, K. R., "Suppressing the Surface Field During Transcranial Magnetic Stimulation", IEEE Transaction on Biomedical Engineering, vol. 53, No. 2. Feb. 2006, pp. 190-194.

* cited by examiner

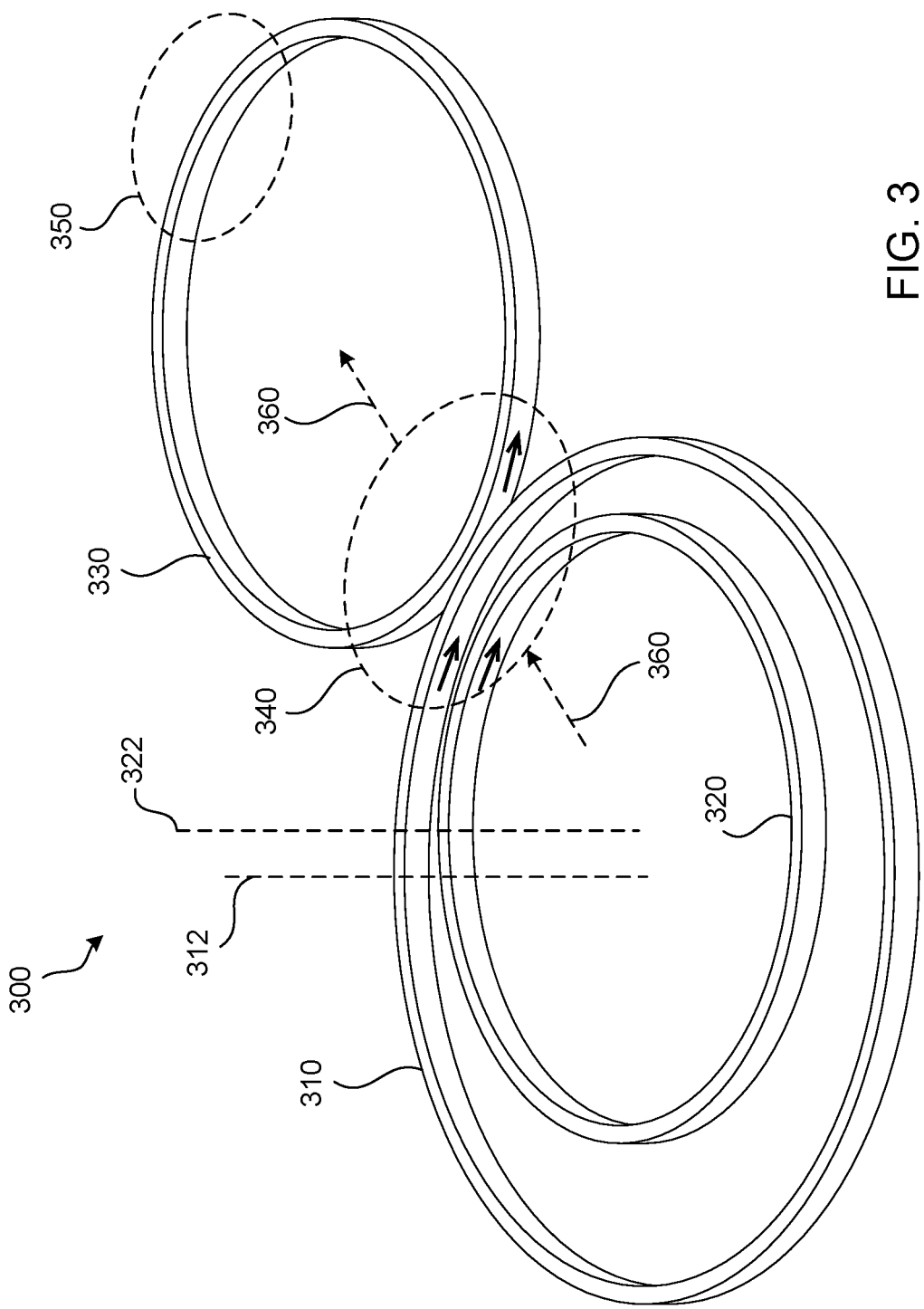

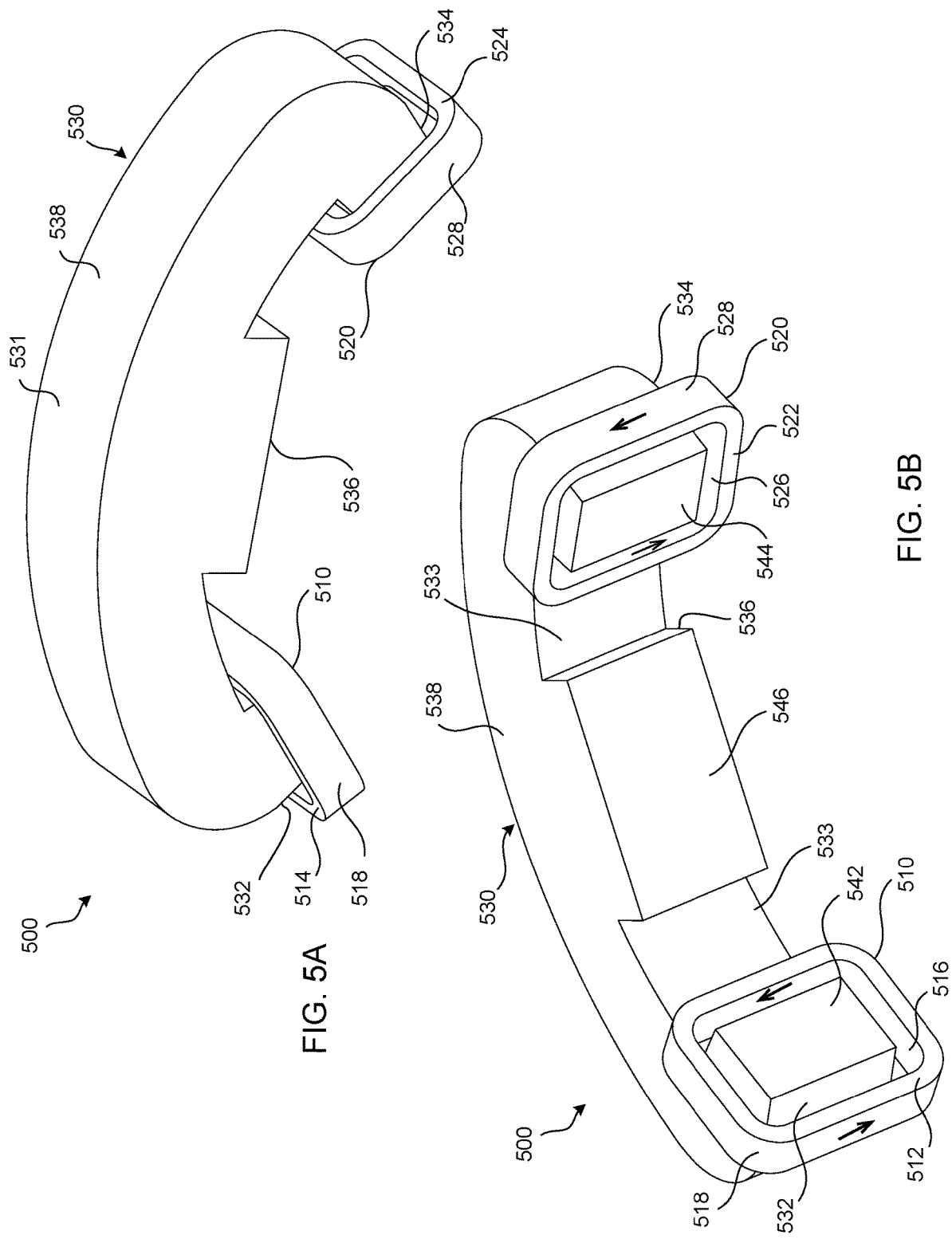

MAGNETIC STIMULATION COILS AND FERROMAGNETIC COMPONENTS FOR TREATMENT AND DIAGNOSTIC PROCEDURES

BACKGROUND

A number of medical ailments may be treated and/or diagnosed through the application of a magnetic field to an afflicted portion of a patient's body. Neurons and muscle cells may be a form of biological circuitry that carry electrical signals and respond to electromagnetic stimuli. When a conductive wire loop is passed through a magnetic field or is in the presence of a changing magnetic field, an electric current may be induced in the wire. The same principle may hold true for conductive biological tissue. When a changing magnetic field is applied to a portion of the body, neurons may be depolarized and stimulated. Muscles associated with the stimulated neurons may contract as though the neurons were firing by normal causes.

A nerve cell or neuron may be stimulated in a number of ways, for example, transcutaneously via transcranial magnetic stimulation (TMS). TMS may use a rapidly changing magnetic field to induce a current on a nerve cell, without having to cut or penetrate the skin. The nerve may "fire" when a membrane potential within the nerve rises with respect to its normal negative ambient level of approximately −90 mV, for example, depending on the type of nerve, local pH of the surrounding tissue, and/or peripheral nerve stimulation.

A magnetic stimulation component may be used to produce the rapidly changing magnetic field inducing a current on a nerve cell. The magnetic stimulation component may fail or operate improperly during treatment, which may result in improper treatment for the patient. For example, the magnetic component may appear to operate correctly, but actually may be producing magnetic field pulses outside of designed device specifications, potentially resulting in improper diagnosis and/or therapy being administered to the patient. Administering an incorrect magnetic field pulse to a patient can affect the magnetic stimulation diagnosis and/or treatment adversely. For example, the treatment provider may believe that the patient is not responding to the treatment, when in fact the intended treatment is not being administered to the patient. Thus, the treatment provider and/or diagnosing clinician may be led to make treatment decisions based on faulty information.

Typical TMS treatment apparatuses generate pulsed magnetic fields that induce currents in electrically sensitive cells (e.g., nerve cells or neurons). These induced currents typically form a complete circuit in the body, such that a path of zero current through the body is created. The currents induced by a TMS treatment apparatus typically drop off to zero in approximately the middle of this path. The rate of this current drop off may be slowed, for example by spreading the current density generated the TMS apparatus over a wide surface area. However, employing this approach may concentrate return currents, which may lead to higher rates of undesirable side effects (e.g., the stimulation of untargeted regions of a subject's brain).

A typical TMS treatment apparatus may include one or more electrically conductive stimulating coils. Such coils may be configured (e.g., wound) in a single layer, such that the coils may be disposed as close as possible to the tissue that is to be stimulated. Such coils may be capable of stimulating brain tissue at a desirable depth relative to the skull. However, such coils are traditionally only configured to stimulation a single location within a subject, and in order to stimulation multiple locations, multiple coils, which may be large and cumbersome, may be required.

SUMMARY

A method, system, and apparatus for treating or diagnosing a patient are described herein. An example system may include an electromagnet, a drive circuit electrically coupled to the electromagnet, and a controller configured to control the drive circuit to provide current to the electromagnet to generate a pulsing magnetic field. The electromagnet may include a first conductive winding and a second conductive winding. The first conductive winding may define an inner surface and an outer surface. The outer surface of the first conductive winding may include a convex portion and a concave portion. The second conductive winding may reside proximate to the concave portion of the outer surface of the first conductive winding.

The first conductive winding may be crescent shaped (e.g., bow, kidney, or falcate shaped). For example, the outer concave segment of the first conductive winding may define a concavity, and at least a portion of the second conductive winding may reside within the concavity of the first conductive winding. Accordingly, the first conductive winding may not encapsulate (e.g., completely surround) the second conductive winding. The first conductive winding may define any shape, such as a non-circular or non-oval shape. Together, the first conductive winding and the second conductive winding may form a kidney shape. The first conductive winding may include a first number of turns and the second conducive winding may include a second number of turns, where the first and second number of turns may be different.

The first and second conductive winding may be configured at a relative distance to one another within a housing such that when the first and second conductive windings are driven they generate at least two independent activation zones within a brain of a subject. The activation zone may be a stimulation or sub-stimulation zone. The stimulation zone may include a region of the brain where the induced current is above a depolarization threshold of neurons of the brain. For example, a first stimulation zone may include currents moving in a first direction and a second stimulation zone may include currents moving in a second direction. The first and second stimulation zones may relate to two different functional regions of the brain.

The electromagnet may further include a magnetic core (e.g., one or more ferromagnetic components). The magnetic core may be comprised of any combination of a powdered magnetic material, a laminated magnetic material, an amorphous magnetic material, one or more of an alloy of iron, nickel, or cobalt, and/or a rare earth element or alloy such as gadolinium, neodymium, or holmium. For example, the magnetic core may include a single ferromagnetic component defining two poles, a first pole defining a substantially circular cross-sectional shape, and a second pole defining a crescent cross-sectional shape. The first pole may define a first pole face and the second pole may define a second pole face. The first and second pole faces may be non-planar with one another. The magnetic core may include a plurality of ferromagnetic components.

An example system for treating or diagnosing a patient may include an electromagnet, a drive circuit electrically coupled to the electromagnet, and a controller configured to control the drive circuit to provide current to the electromagnet to generate a pulsing magnetic field. The electromagnet may include a magnetic core, a first winding, and a second winding. The magnetic core may define a first pole face, a second pole face, and a third pole face, where the third pole face resides between the first and second pole faces. For example, the three pole faces of the magnetic core may be linearly arranged. Further, the first pole face may reside at least partially within an aperture of the first conductive winding, and the second pole face may reside at least partially within an aperture of the second conductive winding. As such, the third pole face may reside between the first and second conductive windings.

The electromagnet may include a third conductive winding. The third pole face of the magnetic core may reside at least partially within the third conductive winding. The third conductive winding may include more turns than each of the first conductive winding and the second conductive winding. Alternatively or additionally, the first conductive winding may include more turns than the second and/or third conductive windings. The third conductive winding may not be concentric with the third pole face.

The electromagnet may include a fourth conductive winding that is configured to at least partially surround the third conductive winding. The electromagnet may also include a return path magnetic core that is configured to cover at least a portion of the fourth conductive winding. For example, the return path magnetic core may define a channel, and one or more of the third and/or fourth conductive winding may be configured to reside at least partially within the channel of the return path magnetic core. In some examples, the return path magnetic core may include two portions, a first portion configured to reside on a first side of the magnetic core and a second portion configured to reside on a second side of the magnetic core. The return path magnetic core may be non-linear in shape.

The magnetic core may define a first pole defining the first pole face, a second pole defining the second pole face, a third pole defining the third pole face, and a fourth pole defining a fourth pole face. The third pole face may reside between the first pole face and the fourth pole face, and the fourth face may reside between the third pole face and the second pole face. For example, the first, second, third, and fourth pole faces may be linearly arranged. The third pole may be configured to cover a portion of a top surface of the first conductive element. Similarly, in some examples, the fourth pole may be configured to cover a portion of a top surface of the second conductive element.

The magnetic core may include multiple segments that are configured to be added or removed to change the shape of each activation zone, the separation of the activation zones, or the relative activation directions. When driven, the first and second conductive windings may circulate current in the same direction (e.g., or opposite directions). The first conductive winding may include a different number of turns that the second conductive winding. The first conductive winding may be configured to be driven at a different level than the second conductive winding to, for example, modify a shape of the pulsing magnetic field generated by the electromagnet. The electromagnet may include a housing that encases one or more magnetic core(s) and/or conductive windings of the electromagnet. The magnetic core may be comprised of any combination of a powdered magnetic material, a laminated magnetic material, an amorphous magnetic material, one or more of an alloy of iron, nickel, or cobalt, and/or a rare earth element or alloy such as gadolinium, neodymium, or holmium.

Another example system for treating or diagnosing a patient may include an electromagnet, a drive circuit electrically coupled to the electromagnet, and a controller configured to control the drive circuit to provide current to the electromagnet to generate a pulsing magnetic field. The electromagnet may include a first conductive element having a central axis, a second conductive element located proximate to the first conductive element and having a central axis, and an external conductive element that defines an aperture. The first and second conductive elements may not be disposed within the aperture of the external conductive element, but the central axis of the first conductive element and the central axis of the second conductive element may pass through the aperture of the external conductive element.

The first and second conductive elements may be placed asymmetrically offset from a central axis of the external conductive element. For example, a center of the first conductive element may reside closer to the external conductive element than a center of the second conductive element. The external conductive element may be a crown coil that is configured to go around a coronal plane of the patient. A magnetic core may include a first pole face and a second pole face, wherein the first pole face resides at least partially within an aperture of the first conductive element and the second pole face resides at least partially within an aperture of the second conductive element.

The first and second conductive elements may be circular or elliptical in shape and together form a figure 8 coil. The first and second conductive elements together may form a B-shaped coil. For example, the first and second conductive elements may form a non-circular coil. The first and second conductive elements may be of different shapes or sizes. The external conductive element may be electrically coupled in series with the first and second conductive elements. The pulsing magnetic field generated by the electromagnet may be configured to induce a first stimulation zone and a second stimulation zone within a brain of a human subject, where a stimulation zone may comprise a region of a brain where the induced current is above a depolarization threshold of neurons of the brain. The system may further comprise a housing encasing the electromagnet.

Another example system for treating or diagnosing a patient may include an electromagnet, a drive circuit electrically coupled to the electromagnet, and a controller configured to control the drive circuit to provide current to the electromagnet to generate a pulsing magnetic field. The electromagnet may include a first conductive winding, a second conductive winding, and a third conductive winding. The second conductive winding may reside at least partially within an aperture of the third conductive windings. For example, the third conductive element may be configured to surround an outer surface of the second conductive element. At least one of the first and second conductive elements may be "B" shaped.

The electromagnetic may also include a first magnetic core and a second magnetic core. The first magnetic core may define a first pole face and a second pole face, and the second magnetic core may define a first pole face and a second pole face. The first pole face of the first magnetic core and the first pole face of the second magnetic core may reside at least partially within an aperture of the first conductive element. The second pole face of the first magnetic core and the second pole face of the second magnetic core may reside at least partially within an aperture of the second conductive element.

BRIEF DESCRIPTION OF THE DRAWINGS

FIG. 3 is a diagram of an example treatment coil that is configured to generate a changing magnetic field in a target anatomy of a subject.

FIG. 5A is a diagram illustrating an overhead perspective of an example treatment coil that is configured to generate a changing magnetic field in a target anatomy of a subject.

FIG. 5B is a diagram illustrating an underneath perspective of the example treatment coil of FIG. 5A that is configured to generate a changing magnetic field in a target anatomy of a subject.

DETAILED DESCRIPTION

Figure 1:
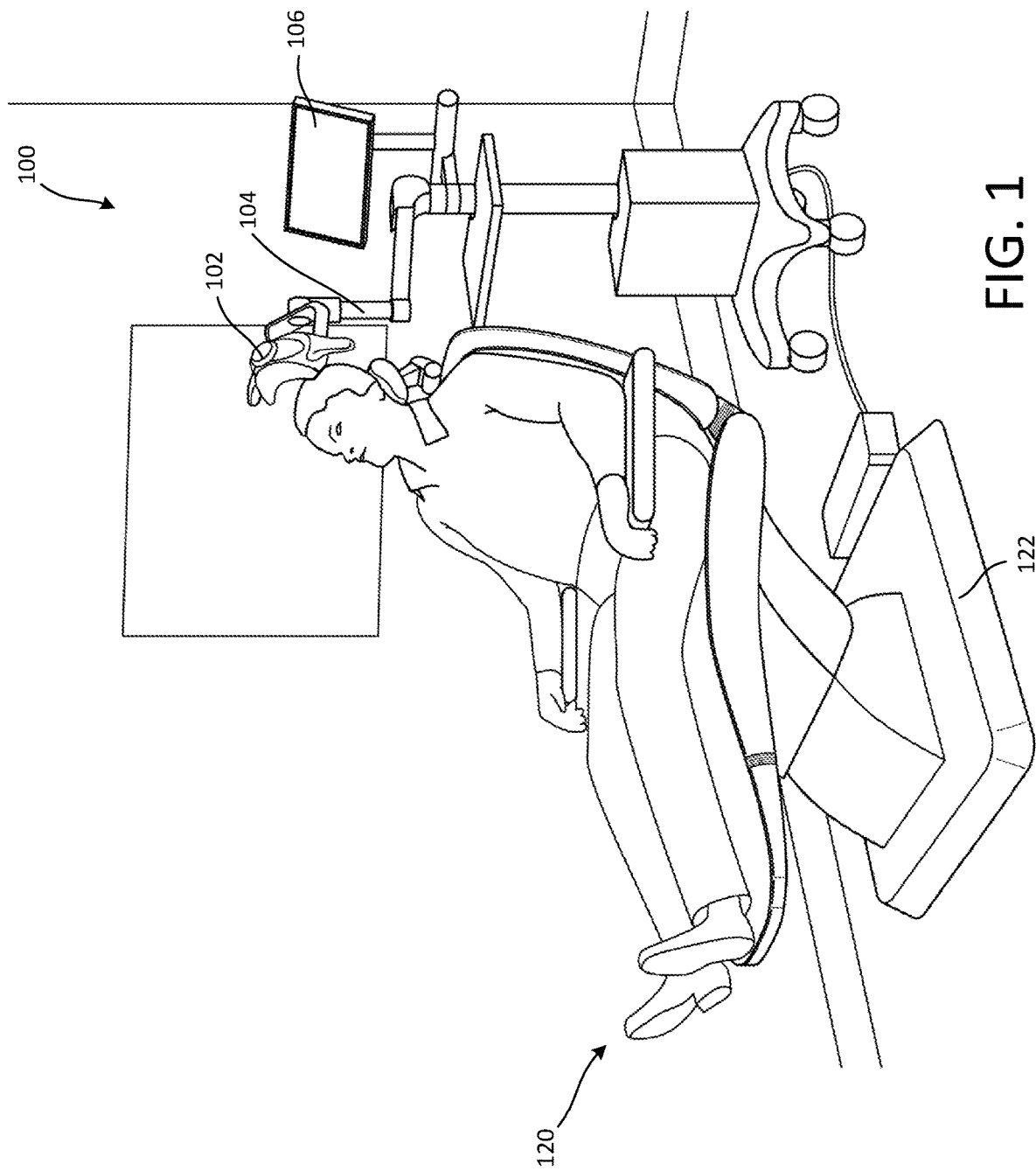
FIG. 1 is a diagram of an example of a treatment or diagnostic system.

In 1831, Michael Faraday discovered that the magnitude of an electric field induced on a conductor is proportional to the rate of change of magnetic flux that cuts across the conductor. Faraday's law, well known to those skilled in the art, may be represented as $E \sim -(A*dB/dt)$, where E is the induced electric field in volts/meter and $dB/dt$ is the time rate of change of magnetic flux density in Tesla/second. In other words, the amount of electric field induced in an object, such as a conductor, may be determined using two factors: the area density and the time rate of change of the flux. The greater the flux density and its derivative, the greater the induced electric field and resulting current density. Magnetic flux may be a function of distance. For example, because the magnetic flux density may decrease in strength with relation to the distance from the source of the magnetic field (e.g., $1/r^3$, $1/r^5$, or the like), the flux density may be greater the closer the conductor is to the source of the magnetic field. When the conductor is a coil, the current induced in the coil by the electric field may be increased in proportion to the number of turns of the coil.

An overview of an example operation and application of a magnetic system in which aspects of the various embodiments may be implemented may be provided. The magnitude of an electric field induced on a conductor may be proportional to the rate of change of magnetic flux density across the conductor. When an electric field is induced in a conductor, the electric field may create a corresponding current flow in the conductor. The current flow may be in the same direction of the electric field vector at a given point. The peak electric field may occur when the time rate of change of the magnetic flux density is the greatest and may diminish at other times. During a magnetic pulse, the current may flow in a direction that tends to preserve the magnetic field (e.g., Lenz's Law).

Certain parts of the anatomy (e.g., nerves, tissue, muscle, brain) may act as a conductor and may carry electric current when an pulsed magnetic field is applied. The pulsed magnetic field may be applied to these parts of the anatomy transcutaneously. For example, in the context of TMS, a time-varying magnetic field may be applied across the skull to create an electric field in the brain tissue, which may produce a current. If the induced current is of sufficient density and/or duration, neuron action potential may be reduced to the extent that the membrane sodium channels open and an action potential response is created. An impulse of current may be propagated along the axon membrane that transmits information to other neurons via modulation of neurotransmitters. Such magnetic stimulation may acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations, metabolism, and/or nerve changes to stimulation thresholds, for example, such that depression may be alleviated.

Non-cortical neurons (e.g., cranial nerves, peripheral nerves, sensory nerves) may be stimulated by an induced electric field. For example, peripheral nerves may be intentionally stimulated to diagnose neuropathologies, for example, by observing response times and conduction velocities in response to a pulsed magnetic field induced stimulus. Discomfort and/or pain may result if the induced electric field applied to a peripheral and/or cranial nerve is very intense, and/or focused on a small area of the nerve. This discomfort may be diminished, for example, by intentionally over-stimulating the sensory nerves in the affected nerve bundle so that they can no longer respond to external pain stimuli, or by reducing the intensity and/or focus of the induced electric field that is causing the pain sensation.

Transcutaneous magnetic stimulation may not be limited to treatment of depression. Transcutaneous magnetic stimulation may be used to treat a patient, such as a human, for example, suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and/or generalized anxiety disorder), post-traumatic stress disorder (one of the anxiety disorders in DSM), obsessive compulsive disorder (e.g., one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, *cannabis* and the like), spinal cord injury and regeneration/ rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, autism spectrum disorders, and/ or eating disorders (such as bulimia, anorexia and binge eating).

A device may take advantage of the above principles to induce an electric field used in a variety of applications. For example, a magnetic device may be used for electrical stimulation of the anatomy. While the discussion herein focuses on magnetic devices that are used in connection with magnetic stimulation of anatomical tissue, a magnetic device may be utilized in any field of endeavor. Further, as the devices provided herein are described with reference to magnetic stimulation such as, for example, Transcranial Magnetic Stimulation (TMS), the devices may be used for any treatment or diagnostic procedure.

A ferromagnetic core may be used in connection with a magnetic device to produce a magnetic field. For example, a ferromagnetic core may include an arc-shaped (e.g., approximately hemispherical) magnetic material. A ferromagnetic core may include a highly saturable magnetic material having a magnetic saturation of at least 0.5 Tesla. A ferromagnetic core may be shaped to optimize the magnetic field distribution in the treatment area. For example, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), deep TMS (dTMS), controlled and/or varied pulse shape TMS (cTMS), reduction of peripheral nerve discomfort, etc. Although examples described herein may be discussed in connection with TMS and rTMS, the examples described herein may be utilized in connection with any type of magnetic stimulation, such as transcutaneous magnetic stimulation, for example. Furthermore, the embodiments presented herein are not limited to the use of ferromagnetic core magnetic stimulation systems, as other core materials may be used such as, for example, an air core.

FIG. 1 is a diagram of an example of a treatment or diagnostic system 100. The treatment or diagnostic system 100 may comprise a processor (not shown), a power supply (not shown), memory (not shown), a transceiver, (not shown), a treatment coil 102, an articulating arm 104, a display device 106, and/or a human subject positioning apparatus 122. The treatment system 100 may be stationary or movable. For example, the treatment system 100 may be integrated into a movable cart, for example, as shown in FIG. 1. In one or more examples, the treatment system 100 may be a TMS treatment system (e.g., NeuroStar®) and/or any other therapeutic and/or diagnostic procedure system.

The treatment coil 102 may be used to administer a therapeutic and/or diagnostic procedure to a human subject 120, for example, TMS. Example treatment coils 102 may include one or more treatment coils and one or more ferromagnetic components that are configured to be disposed proximate to corresponding ones of the one or more treatment coils. The one or more treatment coils and ferromagnetic components of each TMS device may cooperatively generate a magnetic field that exhibits one or more characteristics that differ from those of a magnetic field that is generated by the one or more treatment coils alone. Although illustrated to include the treatment coil 102 and described primarily with respect to TMS, the treatment system 100 may include any device for administration of therapeutic and/or diagnostic procedure of the human subject. In some examples, the treatment system 100 may be used for a diagnostic procedure (e.g., solely for a diagnostic procedure).

The processor of the treatment system 100 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor may perform signal coding, data processing, power control, input/output processing, and/or any other functionality that enables the treatment system 100 to operate. The processor may be integrated together with one or more other components of the treatment system 100 in an electronic package or chip.

The processor of the treatment system 100 may be coupled to and may receive user input data from and/or output user input data to the treatment coil 102, the articulating arm 104, the display device 106 (e.g., a liquid crystal display (LCD) display unit or organic light-emitting diode (OLED) display unit), and/or the human subject positioning apparatus 122. The processor may access information from, and store data in, any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The processor may access information from, and store data in, memory that is not physically located within the treatment system 100, such as on a server (not shown).

The processor may receive power from the power supply, and may be configured to distribute and/or control the power to the other components in the treatment system 100. The power supply may be any suitable device for powering the treatment system 100.

The human subject 120 may be positioned within the human subject positioning apparatus 122. The human subject positioning apparatus 122 may be a chair, recliner, bed, stool, and/or the like. When performing treatment, the treatment coil 102 may be situated such that the human subject's head is positioned under the treatment coil 102. The treatment coil 102 may be adjusted by means of the articulating arm 104 and/or the like.

The treatment system 100 may comprise one or more computer software applications running on the processor. The computer software applications may provide a system graphical user interface (GUI) (e.g., a TMS system GUI) on the display device 106. The computer software applications may incorporate work flow management to guide a technician through the therapeutic and/or diagnostic procedure, and/or supervise and/or control one or more subsystems of the treatment system 100. For example, the computer software applications may control internal system functions, monitor the system status to ensure safe operation, and/or provide the user with a graphical means to manage the preparation for and/or the administration of the therapeutic and/or diagnostic procedure.

Interaction with the computer software applications may be provided via a user interface. In one or more embodiments, the user interface may be the display device 106, which may be a touch screen display. The display device 106 may include touch activated images of alphanumeric keys and/or buttons for user interaction with the treatment system 100. The display device 106 may provide graphic representations of the system activity, messages, and/or alarms. Interactive buttons, fields, and/or images may be displayed via the display device 106, and may enable the technician to direct and/or interact with system functions, for example, such as entering data, starting and stopping the procedure, running diagnostics, adjusting positioning and/or configuration of the treatment coil 102, adjusting the position of one or more sensor(s), and/or the like.

The treatment system 100 may be used for any therapeutic and/or diagnostic procedure. For example, the treatment system may be used for TMS, transcranial direct current stimulation (tDCS), Electroencephalography (EEG), Deep brain stimulation (DBS), a diagnostic procedure, and/or the like. For example, the treatment system 100 may be used for any therapeutic and/or diagnostic procedure that includes the placement of electrodes, sensors, probes, and/or the like on a human subject, such as on the surface of a human subject's head. Although described with reference to a head model, the treatment system 100 may be configured to generate a model of any part of the human subject 120, such as, but not limited to, the arm, neck, chest, leg, and/or the like.

Figure 2:
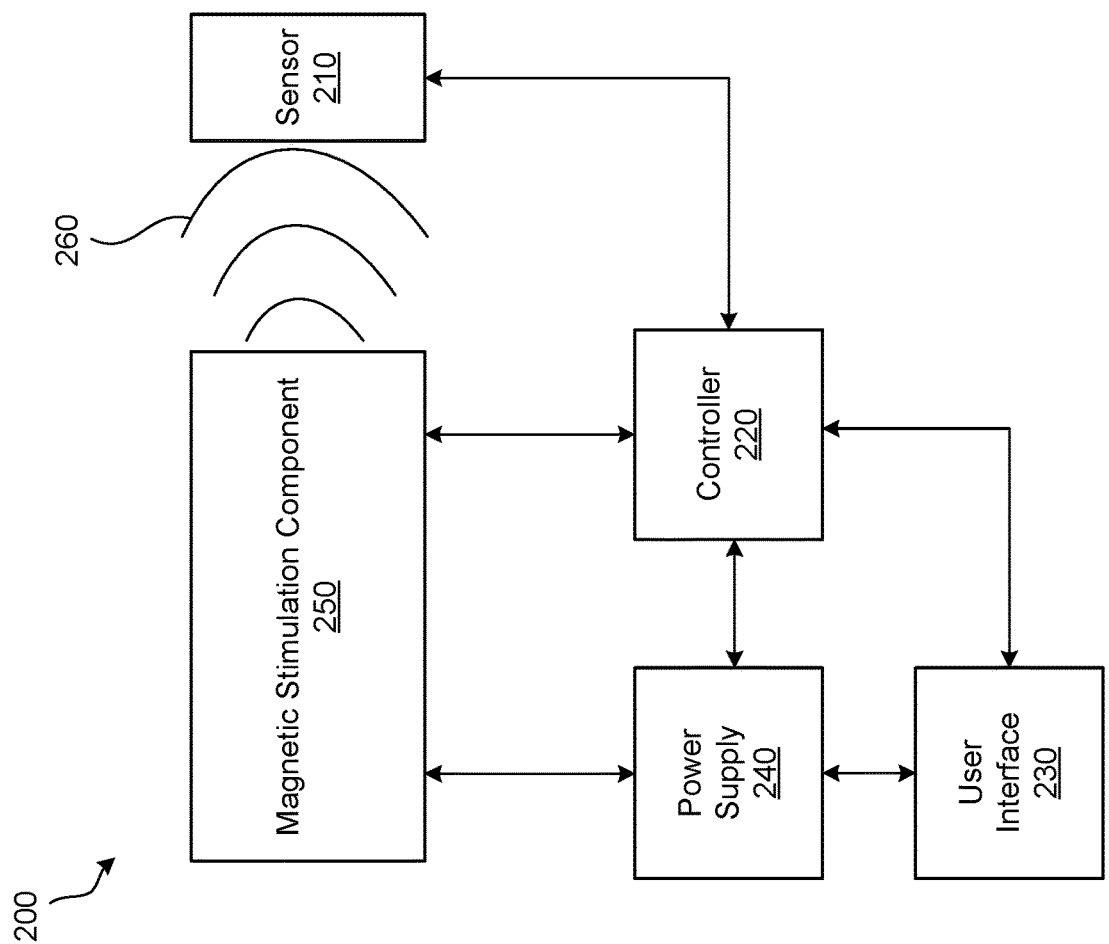
FIG. 2 is a block diagram illustrating an example of a magnetic stimulation system.

FIG. 2 is a block diagram illustrating an example of a magnetic stimulation system 200. The magnetic stimulation system 200 may be an example of the treatment system 100. The magnetic stimulation system 200 may comprise a sensor 210, a controller 220, a user interface 230, a power supply 240, and a magnetic stimulation component 250. The magnetic stimulation component 250 may be an example of the treatment coil 102 of the treatment system 100 of FIG. 1.

The magnetic stimulation component 250 may be configured to generate a pulsing magnetic field 260 to conduct magnetic stimulation therapy on a treatment area of a patient. The magnetic stimulation therapy may be, for example, transcranial magnetic stimulation (TMS). TMS may refer to TMS, repetitive transcranial magnetic stimulation (rTMS), deep TMS (dTMS), cTMS, or the like. The magnetic stimulation component 250 may be a treatment coil. The magnetic stimulation component 250 may include a single treatment coil, multiple treatment coils, and/or an array of treatment coils. The treatment area may be the prefrontal cortex, for example. The magnetic stimulation component 250 may or may not include a core, such as a magnetic core (e.g., ferromagnetic core), for example. The pulsing magnetic field 260 may include one or more pulse bursts. A pulse burst (e.g., each pulse burst) of the pulsing magnetic field 260 may include one or more pulses.

The sensor 210 may be configured to generate a signal associated with a pulsing magnetic field 260. The sensor 210 may be placed between the magnetic stimulation component 250 and a treatment area of a patient. The sensor 210 may be configured to generate a signal associated with the pulsing magnetic field 260 of the magnetic stimulation component 250 (e.g., a signal induced by the pulsing magnetic field 260). For example, the sensor 210 may convert a physical property (e.g., the strength of pulsing magnetic field 260) into a corresponding electrical signal (e.g., a current signal or a voltage signal). As such, the sensor 210 may detect and/or measure a physical parameter of the pulsing magnetic field and generate a signal associated with the pulsing magnetic field using the detected/measured physical parameter. The generated signal may be a voltage signal, a current signal, and/or the like that may be proportional to a change in the pulsing magnetic field 260. For example, a current may be generated in the sensor 210 that may be proportional to the pulsing magnetic field 260. The sensor 210 may generate a voltage that may be proportional to the magnetic flux density (dB/dt) of the pulsing magnetic field 260.

The sensor 210 may include one or more of a conductive coil, a loop (e.g., having a number of turns based on the pulsing magnetic field), a Hall sensor, a magnetoresistive material, a Faraday effect sensor, a Kerr effect sensor, a flux gate sensor, an inductance change element, a nerve tissue response measurement device, an electric field sensor (e.g., in a conductive field), and/or the like. The sensor 210 may be configured to generate more than one signal, for example, more than one signal that is associated with the pulsing magnetic field 260 generated by the magnetic stimulation component 250.

The controller 220 may be any type of hardware, software, or combination thereof. The controller 220 may be configured to control one or more of the components of the magnetic stimulation system 200, such as the sensor 210, the user interface 230, the power supply 240, and/or the magnetic stimulation component 250, for example to conduct magnetic stimulation therapy. For example, the controller 220 may include a general purpose processor, a special purpose processor, a conventional processor, a digital signal processor (DSP), a plurality of microprocessors, one or more microprocessors in association with a DSP core, a microcontroller, any other type of integrated circuit (IC), a state machine, and/or the like.

The controller 220 may be configured to receive inputs from the user interface 230 and/or the sensor 210 to conduct magnetic stimulation therapy accordingly. For example, the controller 220 may perform signal coding, data processing, power control, input/output processing, and/or any other functionality that enables the controller 220 to operate the magnetic stimulation component for magnetic stimulation. The controller 220 may include a drive circuit that generates a drive signal for driving (e.g., powering, such as pulsing) the magnetic simulation component 250. In some examples, the drive circuit may be separate from the controller 220 and electrically coupled to the magnetic stimulation component 250.

Further, the controller 220 may be configured to alter the drive signal provided to the magnetic stimulation component 250 based on inputs received from the user interface 230 and/or the sensor 210. The controller 220 may be configured to estimate (e.g., measure) characteristics associated with the signal generated by the sensor 210 (e.g., associated with one or more peaks of the signal). The controller 220 may estimate a subset of the pulses of the signal or may estimate the signal continuously. By estimating characteristics of the signal, the controller 220 may estimate a model of what is occurring in the brain of a patient in response to the pulsing magnetic field.

Further, the controller 220 may determine whether a failure has occurred based on one or more characteristics of the signal generated by the sensor 210. In the event a failure is determined to have occurred, the controller 220 may enter a failure mode. In the failure mode, the controller 220 may pause the magnetic stimulation procedure, shut down the magnetic stimulation component 250, alert a user of the magnetic stimulation system 200, and/or alter a current applied to the magnetic stimulation component 250. For example, when the controller 220 enters the failure mode, the controller 220 may adjust the frequency at which it estimates characteristics of the generated signal. For example, the controller 220 may check for failures more frequently after a first failure is detected. Further, the magnetic stimulation system 200 may include an indicator that may indicate to a user of the magnetic stimulation system 200 that a failure has occurred. For example, the indicator may be a light, a speaker, an icon displayed on the user interface 230, and/or the like.

The user interface 230 may be any type of interface in which a user of the magnetic stimulation system 200 may initiate, adjust, and/or end the magnetic stimulation procedure. For example, the user interface may include a personal computer (PC), a keyboard, a mouse, a touchscreen, a wireless device, and/or the like, that allows for an interface between the user and the magnetic stimulation system 200.

The power supply 240 may be any type of power source that provides sufficient energy for the magnetic stimulation component 250 to generate the pulsing magnetic field 260 for its intended purpose, for example, for TMS, rTMS, MST or any other type of application. For example, the power supply 240 may be a conventional 120 or 240 VAC main power source.

FIGS. 3-11H are examples of treatment coils that may be used in the treatment system 100 and/or magnetic stimulation system 200. The treatment coils described with reference to FIGS. 3-11H may be used as a treatment coil in a treatment or diagnostic system (e.g., the treatment coil 102 in the treatment or diagnostic system 100) and/or as a part of a magnetic stimulation component of a magnetic stimulation system (e.g., the magnetic stimulation component 250 of the magnetic stimulation system 200). Further, although described as driven by a single drive circuit, the treatment coils described with reference to FIGS. 3-11H may be driven by more than a single drive circuit, for example, driven by a drive circuit for each conductive element or a subset of the conductive elements of the treatment coil. Also, the conductive elements described with reference to FIGS. 3-11H may comprise any suitable material, such as Litz wire.

The treatment coils described with reference to FIGS. 3-11H may include one or more ferromagnetic components. In some examples, the ferromagnetic component(s) may be referred to as a magnetic core. The ferromagnetic components may be comprised of any combination of a powdered magnetic material, a laminated magnetic material, an amorphous magnetic material, one or more of an alloy of iron, nickel, or cobalt, and/or a rare earth element or alloy such as gadolinium, neodymium, or holmium. For instance, the ferromagnetic components described herein may be comprised of any suitable material, and, in some examples, the ferromagnetic components may be made of a plurality of different materials, where the materials define different saturation levels. Although the examples of some of the treatment coils are described with the inclusion of a ferromagnetic component(s), any of the treatment coils described herein may include a subset of the illustrated ferromagnetic component(s) and/or the ferromagnetic component(s) may be omitted.

Also, it should be appreciated that a direct current (DC) magnetic field and/or permanent magnet may be used in any of the treatment coils described herein, for example, to modify the susceptibility of the ferromagnetic component to reshape the magnetic field and/or alter the separation of the activation zones created by the treatment coil.

Finally, it should be appreciated that any of the treatment coils described herein (e.g., the treatment coil 300, 400, 500, 600, 700, 800, 900, 1000, and/or 1100) may be configured to generate a magnetic field that induces one or more activation zones (e.g., two activation zones) within a subject (e.g., at one or more target locations). Accordingly, although the treatment coils are primarily described as generating a magnetic field that induces two activation zones, any of the treatment coils described herein may be configured to generate a magnetic field that induces more or less than two activation zones.

FIG. 3 depicts an example treatment coil 300 that is configured to generate a changing magnetic field in a target anatomy of a subject, such as a human subject (not shown). The target anatomy of the subject may be, for example, brain tissue of the subject. The treatment coil 300 includes a first conductive element 310, a second conductive element 320, and a third conductive element 330. The treatment coil 300 may be disposed proximate to the head of the subject in preparation for or during TMS treatment, for example as shown in FIG. 1. Although not illustrated, the treatment coil 300 may further include a ferromagnetic component. The combination of the conductive elements 310, 320, 330 and the ferromagnetic component collectively may be, for example, referred to as an electromagnet. It should be appreciated that the treatment coil 300 may include more or fewer conductive elements than illustrated. The conductive elements may be referred to as conductive windings.

The conductive elements 310, 320, 330 may be made of any material that exhibits suitable electrical conductivity, such as copper. The first and second conductive elements 310, 320 may be fabricated from different pieces of material or a monolithic piece of material. For example, a length of material (e.g., wire) may be continuously wound so as to define each of the first and second conductive elements 310, 320. The conductive elements 310, 320, 330 may be separately fabricated and supported relative to each other, for example, attached to each other using one or more attachment members (not shown). A plurality of conductive elements (e.g., the first and second conductive elements 310, 320) that are separately fabricated may be placed in electrical communication with one another, for example using one or more electrically conductive attachment members that interconnect respective ones of the conductive elements.

The conductive elements 310, 320, 330 may define any suitable shapes, for example, a substantially circular shape, as illustrated. For example, the conductive elements 310, 320, 330 may have the same or different shapes as illustrated and may have the same or different shapes from each other (e.g., circular, elliptical, oval, rectangular, etc.). Further, one or more of the conductive elements 310, 320, 330 may be configured to define a geometry that conforms to a region of the subject's head. For example, one or more of the conductive elements (in part of in their entirety) may define a concave, band-shaped coil geometry that conforms to a portion of the subject's head (e.g., or other target anatomy).

The treatment coil 300 may define an asymmetric figure 8 coil (e.g., a figure 8 coil where one loop of the "8" is sized or shaped differently than the other loop of the "8," where one or more additional conductive elements are added to a traditional figure 8 coil to break the symmetry of the "8," and/or the like). For example, the treatment coil 300 may include two conductive elements, 310, 320 that define one loop of the "8," and one conductive element 330 that defines the other loop of the "8." As such, the treatment coil 300 may define an asymmetric figure 8 coil. Further, the conductive element 310 may define a larger circumference than the circumference defined by the conductive element 320 and/or the circumference defined by the conductive element 330. Further, in some examples, the circumference defined by the conductive element 330 may be equal to the circumference defined by the conductive element 320. However, it should be appreciated that in some examples, the circumference defined by the conductive element 330 may be larger than or smaller than the circumference defined by the conductive element 320.

The conductive elements 310, 320, and 330 may be situated such that the second conductive element 320 is placed with an aperture defined by the first conductive element 310. Further, a central axis 322 of the second conductive element 320 may be offset from a central axis 312 of the first conductive element 310. As such, the first and second conductive elements 310, 320 are not concentric. The distance between the second conductive element 320 and the first conductive element 310 may be any suitable distance (e.g., such that the first and second conductive elements are not concentric). In other examples, the first and second conductive elements 310, 320 may be concentric. The third conductive element 330 may be located outside of the peripheral of the first conductive element 310, but the first and third conductive elements 310, 330 may be located proximate to one another. There may be a small gap (not shown) located between the proximate sides of the first and third 310, 330 conductive elements, while in some examples, there first and third conductive elements 310, 330 may come into contact with one another. Further, in some examples, the conductive element 310 may be disposed closer to the conductive element 330 than to the conductive element 320.

During a treatment of diagnostic procedure, the treatment coil 300 may be disposed so that an area 340 where the first conductive element 310 is proximate to the third conductive element 330 is placed above a target stimulation zone of the subject. Thereafter, the treatment coil 300 may be driven by a drive circuit of a treatment system and/or magnetic stimulation system. For example, the treatment coil 300 may be configured such that, when driven, currents circulate through the first and second conductive elements in a first direction (e.g., a clockwise direction when viewed from an overhead perspective, as illustrated), while currents circulate through the third conductive element in a second, opposite direction (e.g., counter-clockwise when viewed from the overhead perspective, as illustrated).

As a result, the treatment coil 300 may be configured to generate a magnetic field that causes increased stimulation (e.g., via a stronger pulsing magnetic field) proximate to the area 340 where the first conductive element 310 is proximate to the third conductive element 330, as compared to areas on the substantially opposite side of the third conductive element 330, such as the area 350. As such, the coil configuration of the treatment coil 300 may provide for increased stimulation around the treatment area (e.g., proximate to, for example, below, the area 340) and provides for reduced stimulation (e.g., reduced return currents) in areas outsides of the target stimulation zone (e.g., the area 350).

Further, the conductive element 310 may be disposed closer to the conductive element 330 than to the conductive element 320. The inclusion of the conductive element 310 along with the relative location of the conductive element 310 with respect to the conductive elements 320 and 330 (e.g., the conductive element 310 being disposed closer to the conductive element 330 than the conductive element 320) may shift the magnetic field generated by the treatment coil 300 in the direction defined by the arrows 360 closer to the area 350, as compared to situations where the conductive element 310 isn't included (e.g., as compared to a symmetrical figure 8 coil) and/or the conductive element 310 is disposed closer to the conductive element 320 than the conductive element 330. For example, the inclusion of the conductive element 310 disposed closer to the conductive element 330 than the conductive element 320 may shift the magnetic field along the direction defined by the arrows 360 from an area that is directly between the conductive elements 320, 330 to an area 340 that is shifted closer to the area 350, while not increasing the induced current level proximate to the area 350.

Shifting the magnetic field from an area directly between the conductive elements 320, 330 (e.g., as is the case with a symmetrical figure 8 coil) closer to the area 350 while not increasing the induced current level proximate to the area 350 may be beneficial for certain treatment or diagnostic procedures. For example, when the treatment coil 300 is in position proximate to a patient, the treatment area may be proximate to the area 340, and there may be an area just beyond the area 350 that would be undesirable to stimulate. For instance, during some procedures it may be desirable to locate the area 340 proximate to the dorsal medial or prefrontal cortex for stimulation of the dorsal medial or prefrontal cortex, while locating the area 350 proximate to the sinuses or the bridge of the nose of the patient, where induction of stimulation may be undesirable.

The treatment coil 300 may be configured in other arrangements in order to shift the magnetic field in the direction defined by the arrows 360 from the area directly between the conductive elements 320, 330 to an area 340 that is shifted closer to the area 350. For example, the generated magnetic field may be shifted closer to the area 350 if the conductive element 330 is made smaller in diameter, if the conductive element 310 and/or 320 is made larger in diameter, and/or if the conductive element 320 is moved farther away from the conductive element 330.

In the illustrated example, the first, second, and third conductive elements 310, 320, 330 each define a single loop (e.g., a single amp-turn). In some examples, the treatment coil 300 may include additional conductive elements and/or conductive elements defining more than a single loop (e.g., amp-turn). For example, the treatment coil 300 may include more conductive elements (e.g., or conductive elements defining more loops) on one side than the other (e.g., the side with the first and second conductive elements 310, 320 or the side with the third conductive element 330). For example, a fourth conductive element may be included within the aperture of the second conductive element 320, and for further example, a fifth conductive element may be included in the aperture of the third conductive element 330. The fourth and fifth conductive elements may be not concentric with the second and third conductive elements, respectively. Accordingly, the treatment coil 300 may include any number of additional conductive elements (e.g., or conductive elements defining more loops) as long as there are more conductive elements on one side than the other. Further, when driven, currents may circulate through the fourth conductive element in the first direction (e.g., the same direction and the first and second conductive elements 310, 320), while currents may circulate through the fifth conductive element in the second, opposite direction (e.g., the same direction as the third conductive element 330).

Further, as noted above, the stimulation coil 300 may include a ferromagnetic component (not shown). The ferromagnetic component may be configured to change one or more characteristics of a magnetic field that is generated by the treatment coil 300. The ferromagnetic component may be made of any material that exhibits suitable ferromagnetic properties, such as powdered ferromagnetic iron particles. Further, the ferromagnetic component may define any suitable shape, for example a circular shape, a semi-elliptical, band shape, etc.

The ferromagnetic component may be located proximate to the treatment coil 300. For example, the ferromagnetic component may be located within the aperture of the first conductive element 310 (e.g., in addition to or in lieu of the second conductive element 320). The center of the ferromagnetic component may be offset from the central axis 312 of the first conductive element 310 (e.g., and the second conductive element 320, if included). For example, if the ferromagnetic component has a circular cross-section, then the ferromagnetic component may not be concentric with the first conductive element 310. By offsetting the ferromagnetic component from the central axis 312 of the first conductive element 310, the treatment coil 300 may be configured to generate a magnetic field that is offset from the area 340 where the first conductive element 310 is proximate to the third conductive element 330. Moreover, in some examples, the ferromagnetic component may be configured to at least partially receive or encompass a portion or the entirety of the treatment coil 300. For example, the ferromagnetic component may define a recess that is configured to receive at least a portion of the treatment coil 300, such that when the treatment coil 300 is disposed in the recess, the ferromagnetic component least partially surrounds respective portions of the conductive elements 310, 320, 330.

In some examples, the treatment coil 300 may include a bend such that the treatment coil 300 defines an angle (e.g., such as a 90 degree angle) that allows for return currents to be raised from the head. For example, any combination of the conductive elements 310, 320, 330 may define a bend that causes the conductive element to define an angle (e.g., such as a 90 degree angle) that allows for return currents to be raised from the head. Further, in some examples, the treatment coil 300 may include one or more additional conductive elements that define an angle (e.g., such as a 90 degree angle) that allows for return currents to be raised from the head.

Figure 4B:
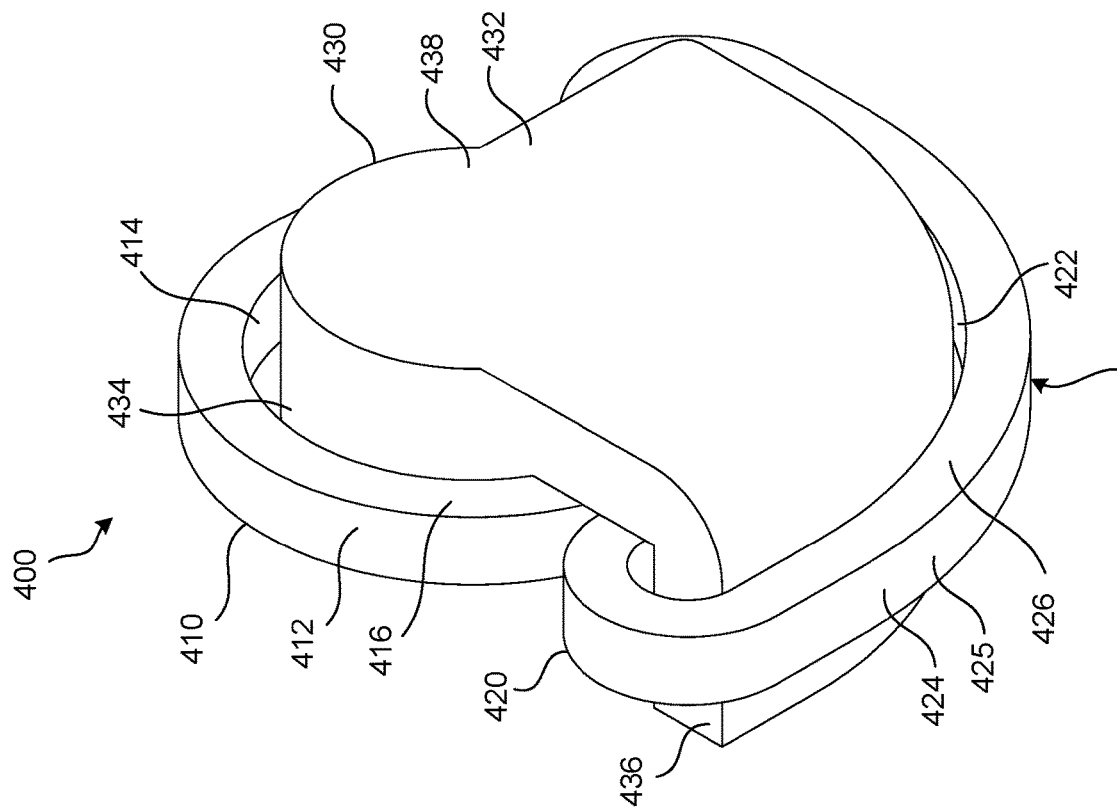
FIG. 4B is a diagram illustrating an overhead perspective of the example treatment coil of FIG. 4A that is configured to generate a changing magnetic field in a target anatomy of a subject.
Figure 4A:
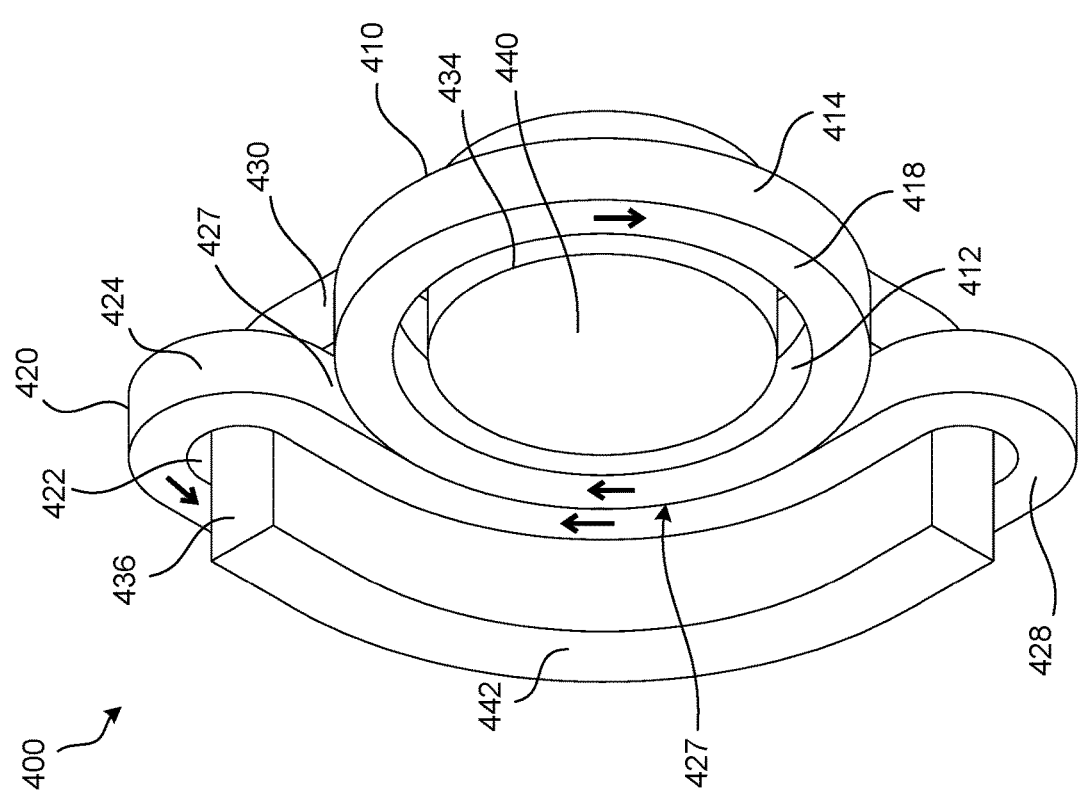
FIG. 4A is a diagram illustrating an underneath perspective of an example treatment coil that is configured to generate a changing magnetic field in a target anatomy of a subject.

FIGS. 4A and 4B depict an example treatment coil 400 that is configured to generate a changing magnetic field in a target anatomy of a subject, such as a human subject (not shown). The target anatomy of the subject may be, for example, brain tissue of the subject. The treatment coil 400 includes a first conductive element 410, a second conductive element 420, and a ferromagnetic component 430. The treatment coil 400 may be disposed proximate to the head of the subject in preparation for or during TMS treatment, for example as shown in FIG. 1. The combination of the conductive elements 410, 420 and the ferromagnetic component 430 collectively may be, for example, referred to as an electromagnet. It should be appreciated that the treatment coil 400 may include more or fewer conductive elements than illustrated. The conductive elements may be referred to as conductive windings. Further, it should also be appreciated that, in some examples, the treatment coil 400 may not include the ferromagnetic component 430.

The first conductive element 410 may be substantially circular in shape, for example, as illustrated. The first conductive element 410 may define an inner surface 412, an outer surface 414, an upper surface 416, and a bottom surface 418. The second conductive winding 420 may define a non-circular or non-oval shape. For example, the second conductive element 420 may be crescent shaped (e.g., bow, kidney, or falcate shaped), for example, as illustrated.

The second conductive element 420 may define an inner surface 422, an outer surface 424, an upper surface 426, and a bottom surface 428. The outer surface 424 of the second conductive element 420 may include a convex portion 425 and a concave portion 427. The first conductive winding 410 may be disposed proximate to the concave portion 427 of the outer surface 424 of the second conductive winding 420. For example, the outer surface 412 of the first conductive winding 410 may be disposed proximate to the concave portion 427 of the outer surface 424 of the second conductive winding 420. For example, the concave portion 427 of the second conductive winding 420 may define a concavity, and at least a portion of the first conductive winding 410 may be disposed within the concavity of the second conductive winding 420. Although at least a portion of the first conductive winding 410 may be disposed within the concavity of the second conductive winding 420, in some examples, such as that illustrated, the second conductive winding 420 may not encapsulate the first conductive winding 410.

The first and second conductive elements 410, 420 may be made of any material that exhibits suitable electrical conductivity, such as copper. The first and second conductive elements 410, 420 may define the same number of turns (e.g., amp-turns), for example, a single turn, as illustrated. Although, it should be appreciated that in some examples, the first conductive element 410 may define a first number of turns, while the second conducive element 420 may define a different, second number of turns. Further, in some examples, the treatment coil 400 may include additional conductive elements and/or conductive elements defining more than a single loop (e.g., amp-turn). For example, the first conductive element 410 may include one or more additional and overlapping conductive elements (e.g., the first conductive element 410 may define more than a single loop) and/or the second conductive element 420 may include one or more additional and overlapping conductive elements (e.g., the second conductive element 420 may define more than a single loop).

The first conductive element 410 and/or the second conductive element 420 may be formed of a single, monolithic piece of conductive material, or, one or more of the first and second conductive elements 410, 420 may be formed by multiple strands of wire. In some examples, the conductive elements 410, 420 may be separately fabricated and supported relative to each other, for example, attached to each other using one or more attachment members (not shown). Further, the treatment coil 400 may include a housing (not shown) that houses the first and second conductive winding 410, 420 and the ferromagnetic component 430.

The ferromagnetic component 430 may be made of any material that exhibits suitable ferromagnetic properties, such as powdered ferromagnetic iron particles. The ferromagnetic component 430 may comprise a body portion 432, a first protruding portion 434, and a second protruding portion 436. The body portion 432 may have a top surface 438 that is substantially parallel with the top surface 416 of the first conductive winding 410 and the top surface 426 of the second conductive winding 420. The first protruding portion 434 may extend from a bottom surface of the body portion 432. The first protruding portion 434 may be disposed within an aperture of the first conductive element 410. The first protruding portion 434 may have a cross-sectional shape that is substantially similar to the shape of the aperture of the first conductive element 410 (e.g., a cross-sectional shape that is substantially circular). Further, in the illustrated example, a bottom surface 440 of the first protruding portion 434 may be substantially planar with the bottom surface 418 of the first conductive element 410. Although, it should be appreciated that in some examples the first protruding portion 434 may be configured so that it extends through the first conductive element 410 such that the bottom surface 440 of the first protruding portion 434 extends beyond the plane of the bottom surface 418 of the first conductive element 410.

The second protruding portion 436 may extend from the bottom surface of the body portion 432. The second protruding portion 436 may be disposed within an aperture of the second conductive element 420. The second protruding portion 436 may have a cross-sectional shape that is substantially similar to the shape of the second conductive element 420 (e.g., a cross-sectional shape that is crescent shaped). Further, in the illustrated example, a bottom surface 442 of the second protruding portion 436 extends beyond the plane of the bottom surface 428 of the second conductive element 420. Although, it should be appreciated that in some examples the second protruding portion 436 may be configured so that the bottom surface 442 of the second protruding portion 436 may be substantially planar with the bottom surface 428 of the second conductive element 420.

During a treatment of diagnostic procedure, the treatment coil 400 may be disposed so that the area where the first conductive element 410 is proximate to the second conductive element 420 may be placed above a target stimulation zone of the subject. For example, the area where the outer surface 412 of the first conductive winding 410 is disposed proximate to the concave portion 427 of the outer surface 424 of the second conductive winding 420 may be placed above the target stimulation zone of the subject. Thereafter, the treatment coil 400 may be driven by a drive circuit of a treatment system and/or magnetic stimulation system. For example, the treatment coil 400 may be configured such that, when driven, currents circulate through the first conductive element 410 in a first direction (e.g., a clockwise direction when viewed from an underneath perspective, as illustrated in FIG. 4A), while currents circulate through the second conductive element 420 in a second, opposite direction (e.g., counter-clockwise when viewed from the underneath perspective, as illustrated in FIG. 4A).

As a result, the treatment coil 400 may be configured to generate a magnetic field that induces an activation zone (e.g., stimulation zone) at the target location that has a crescent shape (e.g., similar to the shape of the second conductive element 420) substantially below the area where the outer surface 412 of the first conductive winding 410 is disposed proximate to the concave portion 427 of the outer surface 424 of the second conductive winding 420. For example, the treatment coil 400 may be configured to generate a magnetic field that induces the activation zone at the target location that has a crescent shape, while also not inducing a stimulation zone proximate to the area of the first conductive element 410 that is disposed away from the concave portion 427 of the outer surface 424 of the second conductive winding 420. Accordingly, the treatment coil 400 may be used to generate a stimulation zone at the target location that wraps around an area where stimulation is not desired (e.g., the interior of the concavity of the activation zone).

Since the treatment coil 400 may be configured such that, when driven, currents circulate through the first conductive element 410 in a first direction, while currents circulate through the second conductive element 420 in a second, opposite direction, the treatment coil 400 may generate a localized activation zone (e.g., that is also crescent shaped). That is, since the currents circulate through the first conductive element 410 and the second conductive element 420 in opposite directions, and since the first and second conductive elements 410, 420 are not concentric with one another, the return currents flow in opposite directions (e.g., the currents flowing through the first and second conductive elements 410, 420 outside of the activation zone are flowing in opposite directions as they leave the activation zone).

Further, it should be appreciated that the concavity of the second conductive element 420 (e.g., the degree or angle of the concave portion 427 of the outer surface 424 of the second conductive winding 420) may be adjusted to adjust the resulting stimulation zone that is caused by the treatment coil 400. For instance, in some examples, the second conductive element 420 may be adjustable to modify the angle of the concavity of the outer surface 424. For example, the second conductive element 420 may include a hinge (e.g., at its midpoint), may be comprised of multiple, interchangeable sections that have varying degrees or angles of concavity, be entirely or partially made of a flexible material, etc. Further, in some examples, the shape of the first conductive element 410 may be adjusted to conform to the degree or angle of the concave portion 427 of the outer surface 424 of the second conductive element 420. Finally, in some examples, one or both of the first and second conductive elements 410, 420 may be substituted for different elements have different, but corresponding curvatures (e.g., as opposed to having the second conductive element 420 be adjustable).

Further, the angle of curvature of the outer surface 424 of the convex portion 425 of the second conductive element 420 may be adjusted, for example, to ensure that the generated stimulation zone wraps around an area where stimulation is not desired. For example, the treatment coil 400 may be disposed such that the convex portion 425 curves up and over top the eyes of the patient (e.g., from the perspective provided by FIG. 4B), where it might be desirable to avoid stimulation.

The treatment coil 400 may be configured such that when the first and second conductive windings 410, 420 are driven the resulting activation zone encompasses two independent areas within a brain of a subject (e.g., the crescent shape encompasses two areas of the brain). The areas within the brain of the subject may be correlated with different functional regions of the brain. For example, the treatment coil 400 may be used to stimulate two different areas within the brain of the subject, such as a first area located below and proximate to one side of the second conductive element 420, and a second area located below and proximate to the other side of the second conductive element 420 (e.g., at either end of the crescent). The currents in the two areas of the brain may move in the same or different directions (e.g., clockwise and/or counter-clockwise).

The activation zone induced by the magnetic field generated by the treatment coil 400 may be a stimulation zone or sub-stimulation zone. The stimulation zone may be at a level where the induced current caused by the pulsing magnetic field generated by the treatment coil 400 is above a depolarization threshold of neurons of the brain, while a sub-stimulation zone may be at a level where the induced current is below the depolarization threshold of neurons of the brain. Further, although described with reference to two activation zones and two treatment areas, the treatment coil 400 may be used to generate a magnetic field that induces more or less activation zones for more or less treatment areas of the patient (e.g., depending on the specific treatment or diagnostic procedure).

The treatment coil 400 may be configured such that the conductive elements 410, 420 and the ferromagnetic component 430 are supported relative to each other. For example, the treatment coil 400 may be configured such that the ferromagnetic component 430 supports the conductive elements 410, 420. One or both of the conductive elements 410, 420 and the ferromagnetic component 430 may include one or more complementary attachment members (not shown) that are configured to enable attachment (e.g., releasable attachment) of the conductive elements 410, 420 to the ferromagnetic component 430. The one or more attachment members may be configured such that the conductive elements 410, 420 and the ferromagnetic component 430 are fixedly supported relative to each other. The one or more attachment members may be configured such that the conductive elements 410, 420 and the ferromagnetic component 430 are movable (e.g., repositionable) relative to each other.

When the conductive elements 410, 420 are supported by (e.g., attached to) the ferromagnetic component 430, the conductive elements 410, 420 may be electrically isolated from the ferromagnetic component 430, for example using a dielectric. The dielectric may be air, and the conductive elements 410, 420 may be spaced from (e.g., not in direct contact with) the ferromagnetic component 430 when the conductive elements 410, 420 are attached to the ferromagnetic component 430. The conductive elements 410, 420 may be attached to the ferromagnetic component 430 using one or more attachment members that are made of any suitable electrically isolating (e.g., dielectric) material.

Further, although not illustrated, in some examples the treatment coil 400 may include a conductive element that surrounds the ferromagnetic element 430. For example, the conductive element may surround the top surface 438 of the ferromagnetic element 430. The conductive element may be raised above the top surface 438, and the conductive element may define an aperture that is raised above the top surface 438 of the ferromagnetic component 430. Further, in some examples, the conductive element may surround the entirety of the first and second conductive elements 410, 420, and the ferromagnetic component 430.

Although not illustrated, in some examples, one or both the conductive elements may define a bend such that the conductive element defines an angle (e.g., such as a 90 degree angle) that allows for return currents to be raised from the patient's head. Also, in some examples, the top surface 438 of the body portion 432 of the ferromagnetic component 430 may be arched or rounded.

Further, it should be appreciated that in some examples, the spacing between the outer surface 414 the first conductive elements 410 and the outer surface 424 of the concave portion 427 of the second conductive element 420 may vary (e.g., may vary throughout the concavity defined by the concave portion 427). For example, the first conductive element 410 may be offset within the concavity defined by the concave portion 427 of the second conductive element 420, or the outer surfaces of the first and second conductive elements 420 may be non-complimentary with one another (e.g., define different shapes and/or curvatures).

FIGS. 5A and 5B depict an example treatment coil 500 that is configured to generate a changing magnetic field in a target anatomy of a subject, such as a human subject (not shown). The target anatomy of the subject may be, for example, brain tissue of the subject. The treatment coil 500 includes a first conductive element 510, a second conductive element 520, and a ferromagnetic component 530. The treatment coil 500 may be disposed proximate to the head of the subject in preparation for or during TMS treatment, for example as shown in FIG. 1. The combination of the conductive elements 510, 520 and the ferromagnetic component 530 collectively may be, for example, referred to as an electromagnet. It should be appreciated that the treatment coil 500 may include more or fewer conductive elements than illustrated. The conductive elements may be referred to as conductive windings.

The first and second conductive elements 510, 520 may be semi-elliptical in shape (e.g., in the shape of a rounded-rectangle). Further, in some examples, the first and second conductive elements 510, 520 may be another shape, such as circular in shape. In some examples, the first and second conductive elements 510, 520 may, together, form a figure 8 coil or a B-shaped coil. The first conductive element 510 may define a bottom surface 512, an upper surface 514, an inner surface 516, and an outer surface 518. Similarly, the second conductive element 520 may define a bottom surface 522, an upper surface 524, an inner surface 526, and an outer surface 528. The first and second conductive elements 510, 520 may be made of any material that exhibits suitable electrical conductivity, such as copper, for example.

The first and second conductive elements 510, 520 may define the same number of turns (e.g., amp-turns), for example, a single turn, as illustrated. Although, it should be appreciated that in some examples, the first conductive element 510 and/or the second conductive element 520 may define multiple turns. For instance, in some examples, the first conductive element 510 may define a first number of turns, while the second conducive element 520 may define a different, second number of turns. Further, in some examples, the treatment coil 500 may include additional conductive elements and/or conductive elements defining more than a single loop (e.g., amp-turn). For example, the first conductive element 510 may include one or more additional and overlapping conductive elements (e.g., the first conductive element 510 may define more than a single loop) and/or the second conductive element 520 may include one or more additional and overlapping conductive elements (e.g., the second conductive element 520 may define more than a single loop).

The first conductive element 510 and/or the second conductive element 520 may be formed of a single, monolithic piece of conductive material, or, one or more of the first and second conductive elements 510, 520 may be formed by multiple strands of wire. In some examples, the treatment coil 500 may include a housing (not shown) that houses the first and second conductive winding 510, 520 and the ferromagnetic component 530.

The ferromagnetic component 530 may be made of any material that exhibits suitable ferromagnetic properties, such as powdered ferromagnetic iron particles. The ferromagnetic component 530 may comprise a main body 538 and a plurality of poles, such as a first pole 532, a second pole 534, and a third pole 536 that extend from the main body 538. Although illustrated as having three poles, in some examples, the ferromagnetic component 530 may include more or less than three poles. The plurality of poles (e.g., the first, second, and third poles 532, 534, 536) may extend outward from the main body 538 (e.g., from a bottom surface 533 of the main body 538). The third pole 536 may reside between the first pole 532 and the second pole 534. For example, the first, second, and third poles 532, 534, 536 may be linearly aligned (e.g., as illustrated). However, it should be appreciated that in some examples, one or more of the first, second, and/or third poles 532, 534, 536 may be aligned in a non-linear manner.

The main body 538 of the ferromagnetic component 530 may define a top surface 531 and a bottom surface 533. The main body 538 may be curved, for example, as illustrated. For example, the top surface 531 of the main body 538 may define a convex surface, while the bottom surface 533 of the main body 538 may define a concave surface. Accordingly, the top surface 531 may be non-planar, and the bottom surface 533 may be non-planar. Further, it should be appreciated that in some examples, the curvature of the top and/or bottom surface 531, 533 of the main body 538 may define a greater or lesser curvature than illustrated. Moreover, it should be appreciated that in some examples, the top surface 531 and/or the bottom surface 533 of the main body 538 may be planar (e.g., flat).

The first pole 532 may define a first pole face 542, the second pole 534 may define a second pole face 544, and the third pole 536 may define a third pole face 546. The first pole 532 may be disposed within an aperture of the first conductive element 510, and the second pole 534 may be disposed within an aperture of the second conductive element 520. The first pole 532 may have a cross-sectional shape that is substantially similar to the shape of the first conductive element 510 (e.g., a cross-sectional shape that is semi-elliptical), and the second pole 534 may have a cross-sectional shape that is substantially similar to the shape of the second conductive element 520 (e.g., a cross-sectional shape that is semi-elliptical). Further, in the illustrated example, a first pole face 542 may be substantially planar with the bottom surface 512 of the first conductive element 510, and the second pole face 544 may be substantially planar with the bottom surface 522 of the second conductive element 520. Although, it should be appreciated that in some examples the first pole face 542 may extend beyond the plane of the bottom surface 512 of the first conductive element 510, and/or the second pole face 544 may extend beyond the plane of the bottom surface 522 of the second conductive element 520.

Although not illustrated, in some examples, the ferromagnetic component 530 may be configured to be adjustable (e.g., the curvature of the ferromagnetic component 530 may be adjustable), for example, relative to the anatomy of the subject's head. For example, the ferromagnetic component 530 may include multiple pieces, such that one or more pieces of the ferromagnetic component 530 may be configured so as to be adjustable relative to one or more other pieces of the ferromagnetic component 530, and/or two or more of the pieces of the ferromagnetic component 530 may be configured to be adjustable (e.g., pivotally adjustable) relative to each other (e.g., through the use of a hinge between the pieces of the ferromagnetic component 530).

The treatment coil 500 may be configured to be driven such that the treatment coil 500 can be used to treat multiple (e.g., two) target areas of a subject. For example, during a treatment or diagnostic procedure, the treatment coil 500 may be disposed so that the bottom surface 533 of the main body 538 between the first pole 532 and the third pole 536 may be placed above a first target area, and the bottom surface 533 of the main body 538 between the third pole 536 and the second pole 534 may be placed above a second target area of the subject. Thereafter, the treatment coil 500 may be driven by a drive circuit of a treatment system and/or magnetic stimulation system. For example, the treatment coil 500 may be configured such that, when driven, currents circulate through the first and second conductive elements 510, 520 in the same direction (e.g., a counter-clockwise direction when viewed from an underneath perspective, as illustrated in FIG. 5B).

As a result, the treatment coil 500 may be configured to generate a magnetic field that induces two activation zones, one at each of the target locations. The activation zones may each define a semi-elliptical shape (e.g., rounded-rectangular in shape) substantially below the bottom surface 533 of the main body 538, where a first activation zone is below the bottom surface 533 between the first pole 532 and the third pole 536 and the second activation zone is below the bottom surface 533 between the second pole 534 and the third pole 536. For example, the treatment coil 500 may be configured to generate magnetic fields that induce two activation zones, while also not inducing a stimulation zone in an area under the third pole face 546. Further, the return currents generated by the treatment coil 500 may be located at either end of the ferromagnetic component 530 (e.g., proximate to the first and second poles 532, 534).

The treatment coil 500 may be configured such that when the first and second conductive elements 510, 520 are driven the resulting activation zone encompasses two independent areas within a brain of a subject. The areas within the brain of the subject may be correlated with different functional regions of the brain. For example, the treatment coil 500 may be used to stimulate two different areas within the brain of the subject, such as a first area located below and proximate to the first pole face 542 and second area located below and proximate the second pole face 544. The currents in the two areas of the brain may move in the same or different directions (e.g., clockwise and/or counter-clockwise). That is, in some examples, the two activation zones may include currents that go in opposite (e.g., antiparallel) directions.

It should be appreciated that, in some examples, the ferromagnetic component 530 may define a third pole 536 that defines a third pole face 546 that is of a trapezoid or parallelogram shape. In such instances, the bottom surface 533 between the first pole 532 and the third pole 536 and the bottom surface 533 between the second pole 534 and the third pole 536 may have different shapes or sizes (e.g., bottom surfaces 533 may be non-mirror images of one another), which may adjust the shape and/or size of the resulting magnetic fields generated by the treatment coil 500 and also the resulting activation zones. Accordingly, the shape of the third pole face 546 may be adjusted based on the particular treatment or diagnostic procedure being performed with the treatment coil 500.

Further, it should be appreciated that in some examples, the ferromagnetic component 530 may be bent such that the first and second poles 532, 534 are brought closer together. In such instances, the bottom surface 533 between the first pole 532 and the third pole 536 and the bottom surface 533 between the second pole 534 and the third pole 536 may have different shapes or sizes (e.g., bottom surfaces 533 may be non-mirror images of one another), which may adjust the shape and/or size of the resulting magnetic fields generated by the treatment coil 500 and also the resulting activation zones. Further, if the ferromagnetic component 530 is bent is such a manner, the resulting the two activation zones may include currents that flow in directions that are exactly antiparallel (e.g., opposite), for example, as compared to the illustrated example where the currents are flowing in directions that are closer to antiparallel.

The activation zone induced by the magnetic field generated by the treatment coil 500 may be a stimulation zone or sub-stimulation zone. The stimulation zone may be at a level where the induced current caused by the pulsing magnetic field generated by the treatment coil 500 is above a depolarization threshold of neurons of the brain, while a sub-stimulation zone may be at a level where the induced current is below the depolarization threshold of neurons of the brain. Further, although described with reference to two activation zones and two treatment areas, the treatment coil 500 may be used to generate a magnetic field that induces more or less activation zones for more or less treatment areas of the patient (e.g., depending on the specific treatment or diagnostic procedure).

The treatment coil 500 may be configured such that the conductive elements 510, 520 and the ferromagnetic component 530 are supported relative to each other. For example, the treatment coil 500 may be configured such that the ferromagnetic component 530 supports the conductive elements 510, 520. One or both of the conductive elements 510, 520 and the ferromagnetic component 530 may include one or more complementary attachment members (not shown) that are configured to enable attachment (e.g., releasable attachment) of the conductive elements 510, 520 to the ferromagnetic component 530. The one or more attachment members may be configured such that the conductive elements 510, 520 and the ferromagnetic component 530 are fixedly supported relative to each other. The one or more attachment members may be configured such that the conductive elements 510, 520 and the ferromagnetic component 530 are movable (e.g., repositionable) relative to each other.

When the conductive elements 510, 520 are supported by (e.g., attached to) the ferromagnetic component 530, the conductive elements 510, 520 may be electrically isolated from the ferromagnetic component 530, for example using a dielectric. The dielectric may be air, and the conductive elements 510, 520 may be spaced from (e.g., not in direct contact with) the ferromagnetic component 530 when the conductive elements 510, 520 are attached to the ferromagnetic component 530. The conductive elements 510, 520 may be attached to the ferromagnetic component 530 using one or more attachment members that are made of any suitable electrically isolating (e.g., dielectric) material.

FIGS. 6A-D depict an example treatment coil 600 that is configured to generate a changing magnetic field in a target anatomy of a subject, such as a human subject (not shown). The target anatomy of the subject may be, for example, brain tissue of the subject. The treatment coil 600 includes a first conductive element 610, a second conductive element 620, a third conductive element 660, a fourth conductive element 670, a first ferromagnetic component 630, a second ferromagnetic component 680, and a third ferromagnetic component 690. The treatment coil 600 may be disposed proximate to the head of the subject in preparation for or during TMS treatment, for example as shown in FIG. 1. The combination of the conductive elements 610, 620, 660, 670 and the ferromagnetic components 630, 680, 690 collectively may be, for example, referred to as an electromagnet. It should be appreciated that the treatment coil 600 may include more or fewer conductive elements and/or ferromagnetic components than illustrated. The conductive elements may be referred to as conductive windings.

The first and second conductive elements 610, 620 may be semi-elliptical in shape (e.g., in the shape of a rounded-rectangle). Further, in some examples, the first and second conductive elements 610, 620 may be another shape, such as circular in shape. In some examples, the first and second conductive elements 610, 620 may, together, form a figure 8 coil or a B-shaped coil. The first conductive element 610 may define a bottom surface 612, an upper surface 614, an inner surface 616, and an outer surface 618. Similarly, the second conductive element 620 may define a bottom surface 622, an upper surface 624, an inner surface 626, and an outer surface 628. The first and second conductive elements 610, 620 may be made of any material that exhibits suitable electrical conductivity, such as copper, for example.

The first and second conductive elements 610, 620 may define the same number of turns (e.g., amp-turns), for example, a single turn, as illustrated. Although, it should be appreciated that in some examples, the first conductive element 610 and/or the second conductive element 620 may define multiple turns. For instance, in some examples, the first conductive element 610 may define a first number of turns, while the second conducive element 620 may define a different, second number of turns. By defining more turns on one side (e.g., one conductive element 610, 620) than the other may result in the treatment coil 600 generating two activation zones that have different strengths or depths (e.g., when each side is driven at the same power level). Further, in some examples, the treatment coil 600 may include additional conductive elements and/or conductive elements defining more than a single loop (e.g., amp-turn). For example, the first conductive element 610 may include one or more additional and overlapping conductive elements (e.g., the first conductive element 610 may define more than a single loop) and/or the second conductive element 620 may include one or more additional and overlapping conductive elements (e.g., the second conductive element 620 may define more than a single loop).

The first conductive element 610 and/or the second conductive element 620 may be formed of a single, monolithic piece of conductive material, or, one or more of the first and second conductive elements 610, 620 may be formed by multiple strands of wire. In some examples, the treatment coil 600 may include a housing (not shown) that houses the first and second conductive winding 610, 620 and the first ferromagnetic component 630.

The first ferromagnetic component 630 may be made of any material that exhibits suitable ferromagnetic properties, such as powdered ferromagnetic iron particles. The first ferromagnetic component 630 may comprise a main body 638 and a plurality of poles, such as a first pole 632, a second pole 634, and a third pole 636 that extend from the main body 638. Although illustrated as having three poles, in some examples, the first ferromagnetic component 630 may include more or less than three poles. The plurality of poles (e.g., the first, second, and third poles 632, 634, 636) may extend outward from the main body 638 (e.g., from the bottom surface 633 of the main body 638). The third pole 636 may reside between the first pole 632 and the second pole 634. For example, the first, second, and third poles 632, 634, 636 may be linearly aligned (e.g., as illustrated). However, it should be appreciated that in some examples, one or more of the first, second, and/or third poles 632, 634, 636 may be aligned in a non-linear manner.

The main body 638 of the first ferromagnetic component 630 may define a top surface 631 and a bottom surface 633. The main body 638 may be curved, for example, as illustrated. For example, the top surface 631 of the main body 638 may define a convex surface, while the bottom surface 633 of the main body 638 may define a concave surface. Accordingly, the top surface 631 may be non-planar, and the bottom surface 633 may be non-planar. Further, it should be appreciated that in some examples, the curvature of the top and/or bottom surface 631, 633 of the main body 638 may define a greater or lesser curvature than illustrated. Moreover, it should be appreciated that in some examples, the top surface 631 and/or the bottom surface 633 of the main body 638 may be planar (e.g., flat).

The first pole 632 may define a first pole face 642, the second pole 634 may define a second pole face 644, and the third pole 636 may define a third pole face 646. The first pole 632 may be disposed within an aperture of the first conductive element 610, and the second pole 634 may be disposed within an aperture of the second conductive element 620.

The first pole 632 may have a cross-sectional shape that is substantially similar to the shape of the first conductive element 610 (e.g., a cross-sectional shape that is semi-elliptical), and the second pole 634 may have a cross-sectional shape that is substantially similar to the shape of the second conductive element 620 (e.g., a cross-sectional shape that is semi-elliptical). Further, in the illustrated example, a first pole face 642 may be substantially planar with the bottom surface 612 of the first conductive element 610, and the second pole face 644 may be substantially planar with the bottom surface 622 of the second conductive element 620. Although, it should be appreciated that in some examples the first pole face 642 may extend beyond the plane of the bottom surface 612 of the first conductive element 610, and/or the second pole face 644 may extend beyond the plane of the bottom surface 622 of the second conductive element 620.

Although not illustrated, in some examples, the first ferromagnetic component 630 may be configured to be adjustable (e.g., the curvature of the first ferromagnetic component 630 may be adjustable), for example, relative to the anatomy of the subject's head. For example, the first ferromagnetic component 630 may include multiple pieces, such that one or more pieces of the first ferromagnetic component 630 may be configured so as to be adjustable relative to one or more other pieces of the first ferromagnetic component 630, and/or two or more of the pieces of the first ferromagnetic component 630 may be configured to be adjustable (e.g., pivotally adjustable) relative to each other (e.g., through the use of a hinge between the pieces of the first ferromagnetic component 630).

The third and fourth conductive elements 660, 670 may be semi-elliptical in shape (e.g., shaped like a rounded-rectangle). Further, in some examples, the third and fourth conductive elements 660, 670 may be another shape, such as circular in shape. The third conductive element 660 may define an inner surface 662, an outer surface 664, an upper surface 663, and a bottom surface 665. Similarly, the fourth conductive element 670 may define an inner surface 672, an outer surface 674, an upper surface 673, and a bottom surface 675. The fourth conductive element 670 may be bent downwards, for example, as illustrated. For example, the bottom surface 675 of the fourth conductive element 670 may be concave, while the upper surface 673 may be convex. Although, it should be appreciated that in some examples, one or more of the upper and/or bottom surfaces 673, 675 of the fourth conductive element 670 may be planar (e.g., such that the fourth conductive element 670 is not bent). Further, the fourth conductive element 670 may define a larger circumference than the third conductive element 660. The third conductive element 600 may, at least partially, reside within an aperture of the fourth conductive element 670. That is, the fourth conductive element 670 may surround (e.g., substantially) the third conductive element 660.

The third and fourth conductive elements 660, 670 may be made of any material that exhibits suitable electrical conductivity, such as copper. The third conductive element 660 and/or the fourth conductive element 670 may be formed of a single, monolithic piece of conductive material, or, one or more of the third and fourth conductive elements 660, 670 may be formed by multiple strands of wire. In some examples, the treatment coil 600 may include a housing (not shown) that houses the first, second, third, and fourth conductive elements 610, 620, 660, 670 and the first, second, and third ferromagnetic components 630, 680, and 690.

The third and fourth conductive elements 660, 670 may define the same number of turns (e.g., amp-turns), for example, a single turn, as illustrated. Although, it should be appreciated that in some examples, the third conductive element 660 and/or the fourth conductive element 670 may define multiple turns. For instance, in some examples, the third conductive element 660 may define a first number of turns, while the fourth conducive element 670 may define a different, second number of turns.

The second and third ferromagnetic components 680, 690 may be made of any material that exhibits suitable ferromagnetic properties, such as powdered ferromagnetic iron particles. The second and third ferromagnetic components 680, 690 may be referred to as return path ferromagnetic components (e.g., return path magnetic cores). The second ferromagnetic component 680 may define a channel 682, a bottom surface 684, an inner surface 685, a top surface 686, an outer surface 687, a first pole 688, and a second pole 689. Similarly, the third ferromagnetic component 690 may define a channel 692, a bottom surface 694, an inner surface 695, a top surface 696, an outer surface 697, a first pole 698, and a second pole 699. Each of the bottom surfaces 684, 694, the top surfaces 686, 696, the first poles 688, 698, and the second poles 689, 699 of the second and third ferromagnetic components 680, 690 may be planar. Although, it should be appreciated that in some examples, one or more of the bottom surfaces 684, 694, the top surfaces 686, 696, the first poles 688, 698, and/or the second poles 689, 699 of the second and third ferromagnetic components 680, 690 may be curved or otherwise shaped.

The second and third ferromagnetic components 680, 690 may be curved. For example, the inner surfaces 685, 695 of the second and third ferromagnetic components 680, 690 may be concave, while the outer surfaces 687, 697 of the second and third ferromagnetic components 680, 690 may be convex. For example, the curvature of the inner and outer surfaces 685, 695, 687, 697 of the second and third ferromagnetic components may be substantially similar to the curvature of the inner and outer surfaces of the fourth conductive element 670. However, the curvature of the inner and outer surfaces 685, 695, 687, 697 of the second and third ferromagnetic components 680, 690 is not limited to that illustrated in FIGS. 6A-D.

The second and third ferromagnetic components 680, 690 may be substantially the same size and shape. However, in some examples, the second and third ferromagnetic components 680, 690 may have a different size and/or shape than illustrated. Further, in some example, the size or shape of the second ferromagnetic component 680 may be different from the size or shape of the third ferromagnetic component 690 (e.g., to shift the size and/or shape of the magnetic field generated by the treatment coil 600). Also, in some examples, one or both of the second or third ferromagnetic components 680, 690 may be omitted from the treatment coil 600.

The size (e.g., depth) and shape of the channels 682, 692 of the second and third ferromagnetic components 680, 690 may be configured so that the fourth conductive element 670 may be received within the channels 682, 692. That is, the channels 682, 692 may be sized and shaped so that at least a portion of the fourth conductive element 670 may reside within the channels 682, 692. It should be appreciated that more or less of the fourth conductive element 670 than illustrated in FIGS. 6A-D may reside within the channels 682, 692 of the second and third ferromagnetic components 680, 690. For example, the channels 682, 692 may be configured such that the bottom surface 675 of the fourth conductive element 670 may be non-planar with the plane defined by the bottom surfaces 684, 694 of the second and third ferromagnetic components 680, 690 (e.g., the fourth conductive element 670 may extend beyond or out of the channels 682, 692, for example, as illustrated). Although, it should be appreciated that in some examples, the channels 682, 692 may be configured such that the bottom surface 675 of the fourth conductive element 670 may be planar with the plane defined by the bottom surfaces 684, 694. Further, the second and third ferromagnetic components 680, 690 may wrap around any portion of the fourth conductive element 670 (e.g., more or less than is illustrated in FIGS. 6A-D). For instance, in some examples, the entirety of the fourth conductive element 670 may reside within the channels 682, 692 of the second and third ferromagnetic components 680, 690 (e.g., second and third ferromagnetic components 680, 690 may be a single, monolithic component).

Figure 6A:
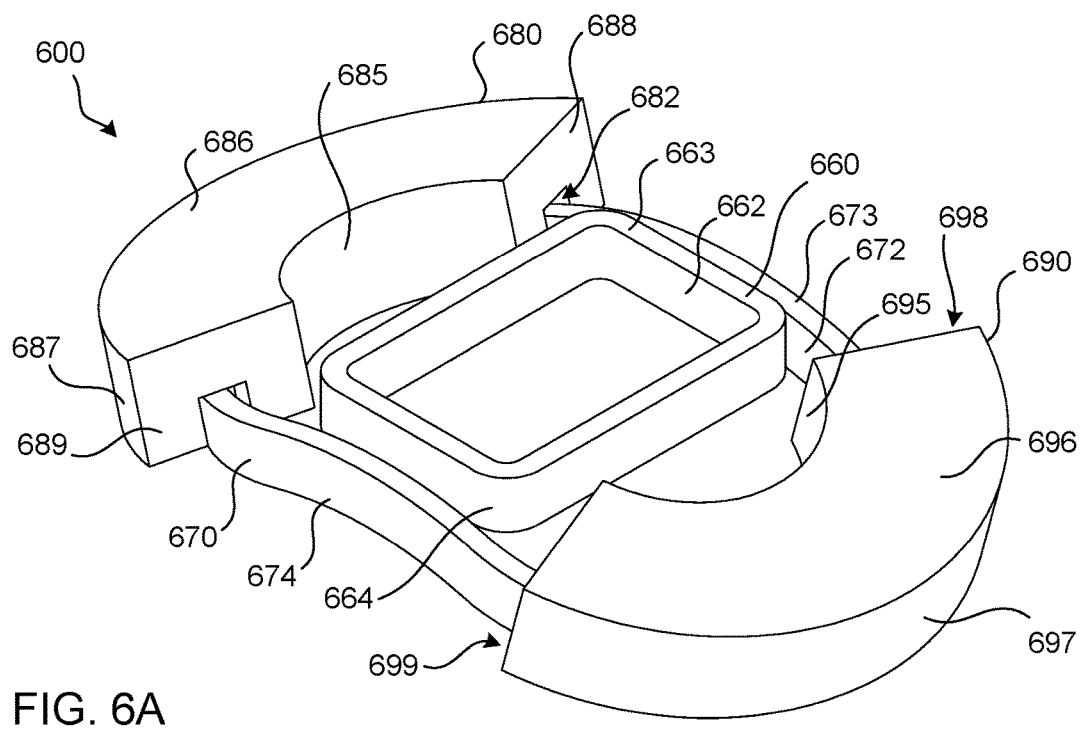
FIG. 6A is a diagram illustrating an overhead perspective of an example treatment coil that is configured to generate a changing magnetic field in a target anatomy of a subject.
Figure 6B:
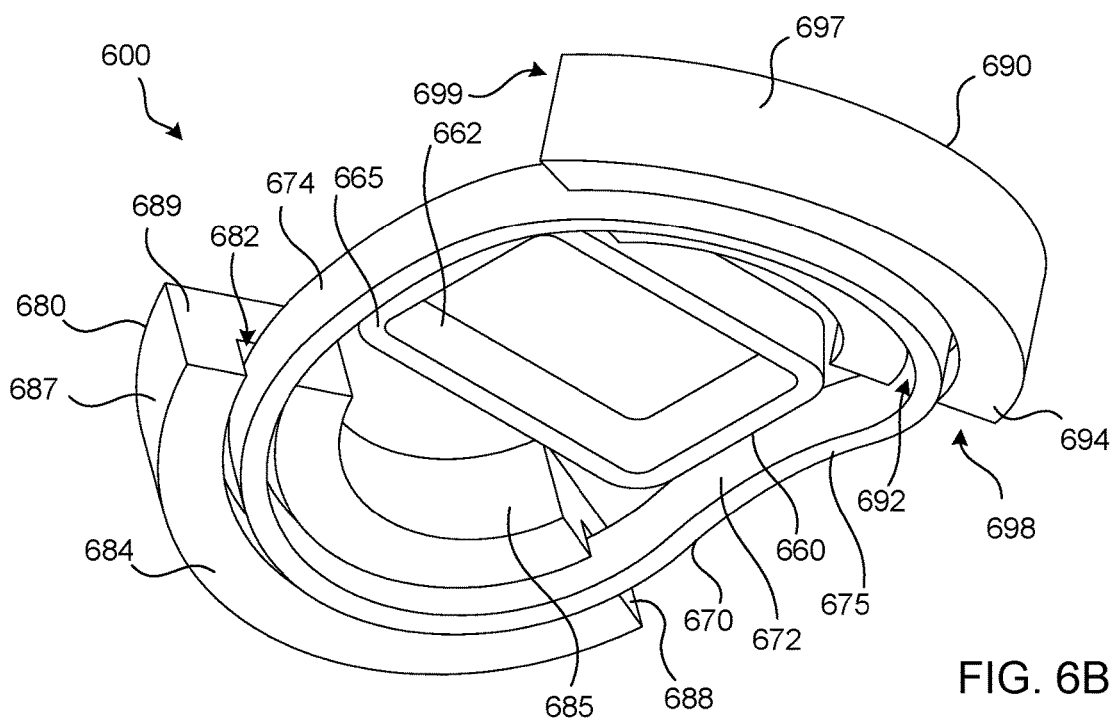
FIG. 6B is a diagram illustrating an underneath perspective of the example treatment coil of FIG. 6A that is configured to generate a changing magnetic field in a target anatomy of a subject.
Figure 6C:
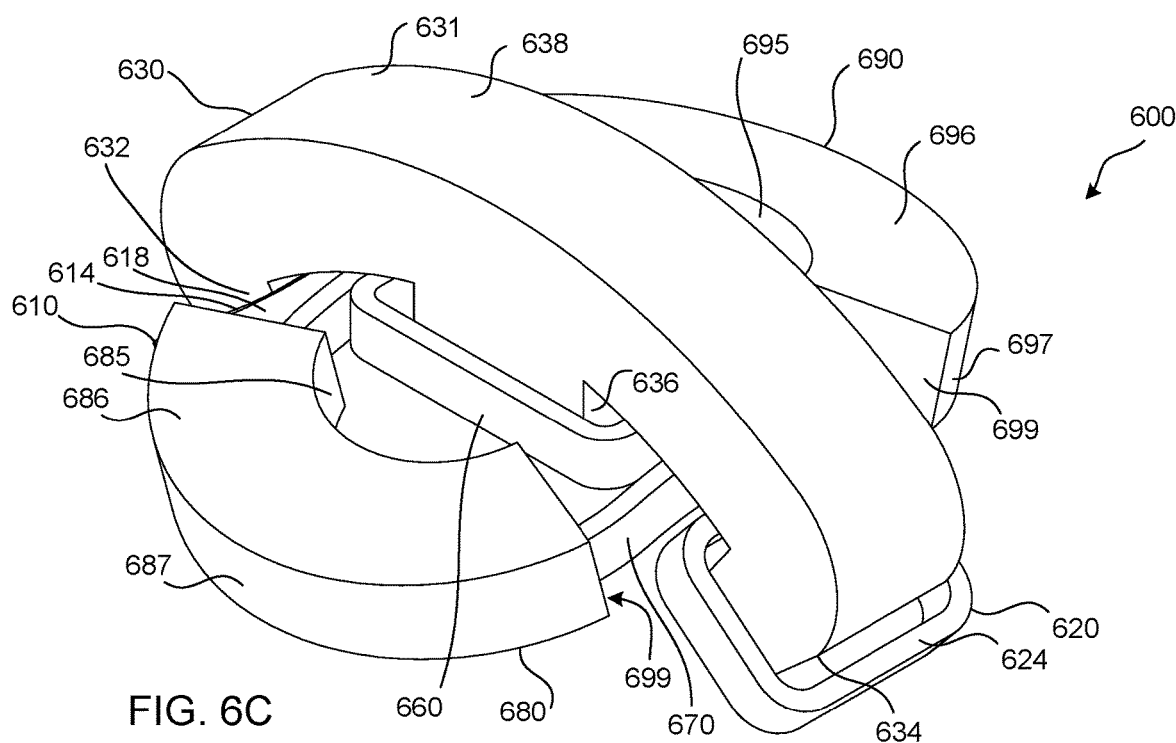
FIG. 6C is a diagram illustrating an overhead perspective of the example treatment coil of FIG. 6A that is configured to generate a changing magnetic field in a target anatomy of a subject.
Figure 6D:
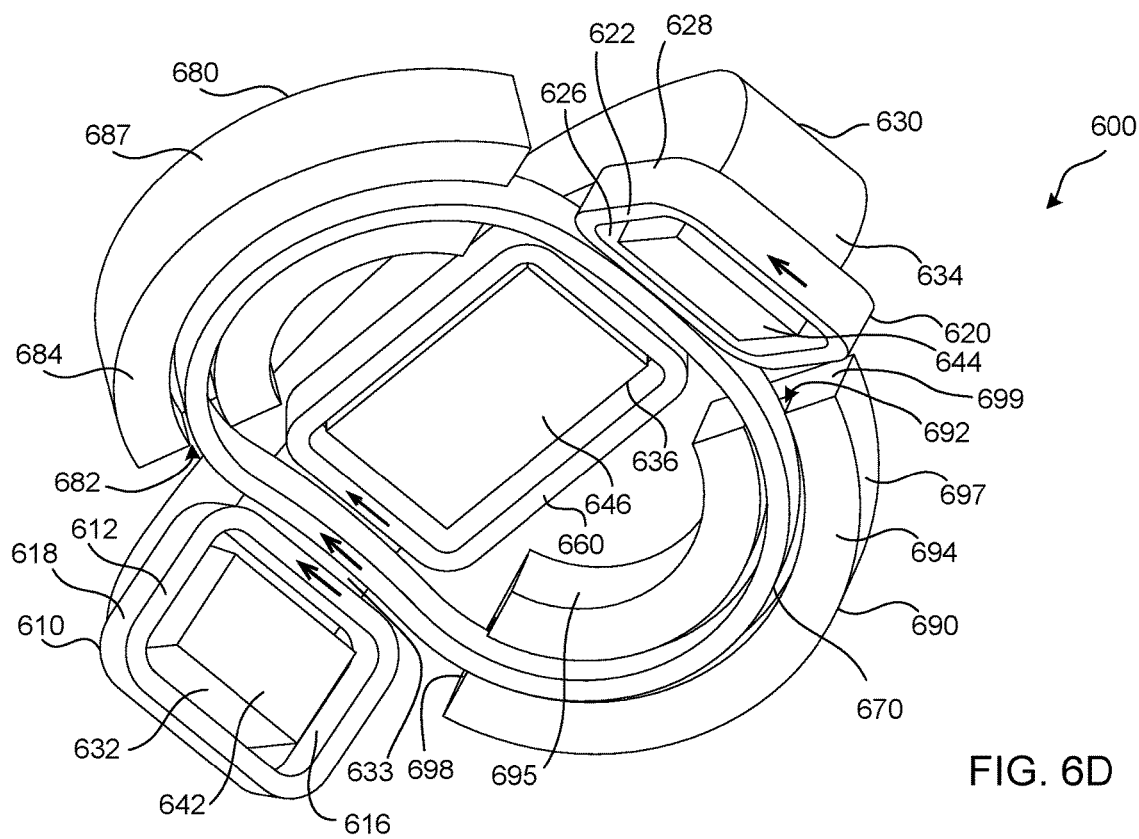
FIG. 6D is a diagram illustrating an underneath perspective of the example treatment coil of FIG. 6A that is configured to generate a changing magnetic field in a target anatomy of a subject.

Referring to FIGS. 6C-D, the treatment coil 600 may be configured such that the third pole 636 of the first ferromagnetic component 630 resides within an aperture of the third conductive element 660. For example, the third pole face 646 of the third pole 636 may be substantially planar with the bottom surface 665 of the third conductive element 660. However, it should be appreciated that in other examples, the third pole face 646 may be non-planar with the bottom surface 665 of the third conductive element 660 (e.g., the third pole face 646 may extend through the third conductive element 660). Further, the third pole 636 may also reside within (e.g., partially within) an aperture of the fourth conductive elements 670. Accordingly, the third and fourth conductive elements 660, 670 may be situated such that the third pole 636 of the first ferromagnetic component 630 resides within apertures of both the third and fourth conductive elements 660, 670, and the third conductive element 660 resides within an aperture of the fourth conductive element 670, for example, as illustrated.

The treatment coil 600 may be disposed so that the area where the first, third, and fourth conductive elements 610, 660, 670 are proximate to each other (e.g., below the bottom surface 633 of the ferromagnetic component 630) may be placed above a first target area, and the area where the second, third, and fourth conductive elements 620, 660, 670 are proximate to each other (e.g., below the opposite bottom surface 633 of the first ferromagnetic component 630) may be placed above a second target area of the subject. Thereafter, the treatment coil 600 may be driven by a drive circuit of a treatment system and/or magnetic stimulation system. For example, the treatment coil 600 may be configured such that, when driven, currents circulate through the first and second conductive elements 610, 620 in the same direction (e.g., a counter-clockwise direction when viewed from an underneath perspective, as illustrated in FIG. 6D), and currents circulate through the third and fourth conductive elements 660, 670 in an opposite direction (e.g., a clockwise direction when viewed from the underneath perspective, as illustrated in FIG. 6D), or vice versa.

As a result, the treatment coil 600 may be configured to generate a magnetic field that induces two activation zones, one at each of the target locations, where each of the activation zones have an elliptical shape (e.g., substantially below the area where the first, third, and fourth conductive elements 610, 660, 670 are proximate to each other, and substantially below the area where the second, third, and fourth conductive elements 620, 660, 670 are proximate to each other, respectively). For example, the treatment coil 600 may be configured to generate magnetic fields that induce two activation zones, while also not inducing a stimulation zone in an area under the third pole face 646.

The inclusion of the third and fourth conductive elements 660, 670 and the second and third ferromagnetic components 680, 690 may act to spread the return currents caused by the magnetic field generated by the treatment coil 600 (e.g., as compared to when any combination of the third and fourth conductive element 660, 670 or the second and third ferromagnetic components 680, 690 are not included). Any combination of the third and fourth conductive elements 660, 670 and the second and third ferromagnetic components 680, 690 may be included in the treatment coil 600 to, for example, further pronounce or enhance the two activation zones created by the magnetic field (e.g., under the first and second target areas) and/or prevent the two activation zones from merging into a single activation zone (e.g., a single oval or circular shaped activation zone under the third pole face 646). For instance, the inclusion of the third and fourth conductive elements 660, 670 may distort the magnetic field generated by the treatment coil 600 by spreading the return currents to areas that are substantially under and proximate to the second and third ferromagnetic components 680, 690, and the inclusion of the second and third ferromagnetic components 680, 690 may enhance this spread of the return currents. For example, the inclusion of the third and fourth conductive elements 660, 670 may pull the return currents further away from the third pole face 646 to, for example, enhance the two activation zones and prevent a single activation zone (e.g., one big ring) from resulting. Further, the inclusion of the third and fourth conductive elements 660, 670 may make the treatment coil 600 more energy efficient when creating the two activation zones. And the inclusion of the second and third ferromagnetic components 680, 690 may cause the return currents to diverge away from the third pole face 646, which may enhance the currents inside of the two activation zones.

To further elaborate, and as can be applied to any of the treatment coils described herein, when a conductive element of a treatment coil is driven, a loop of current may be created through the conductive element. Since the loop of current is changing over time (e.g., being pulsed), the loop of current may induce current in another conductive element that opposes this change (e.g., that is driving current in an opposite direction). The loop of current may have a shape similar to the shape of the conductive element, but the activation zone (e.g., and/or the magnetic field caused by the loop of current) may have different shape than the conductive element. For example, an activation zone may be created when the currents converge, which may create an activation zone of higher current density and/or larger electric field. The activation zone may be defined by how the conductive elements approach each other, and for example, may be changed through the addition of one or more ferromagnetic components (e.g., and/or one or more additional conductive elements). A ferromagnetic component may enhance the local magnetic field and enhance the electric field, for example, by spreading the return currents away from an area between the two activation zones.

For instance, and with specific reference to FIG. 6D, the ferromagnetic component 630 may enhance or further pronounce the two activation zones created when driving the treatment coil 600. That is, the ferromagnetic components 680, 690 may enhance the electric field by drawing the return currents out towards the respective ferromagnetic component 680, 690 when the return currents are leaving an activation zone (e.g., spreading the return currents out away from the third pole face 646) because, for example, the return currents take the path of least resistance. Without the inclusion of the ferromagnetic components 680, 690, the return currents may take a shorter path, for example, the path defined by the conductive element 660. As such, the ferromagnetic components 680, 690 may assist in ensuring that the two activation zones do not combine (e.g., merge) into one, large activation zone (e.g., a single activation zone that includes the area under the third pole face 646).

The treatment coil 600 may be configured such that when the conductive elements 610, 620, 660, 670 are driven the resulting activation zone encompasses two independent areas within a brain of a subject. The areas within the brain of the subject may be correlated with different functional regions of the brain. For example, the treatment coil 600 may be used to stimulate two different areas within the brain of the subject, such as a first area located below and proximate to the first pole face 642 and a second area located below and proximate to the second pole face 644 of the first ferromagnetic component 630. The currents in the two areas of the brain may move in the same or different directions (e.g., clockwise and/or counter-clockwise).

The activation zone induced by the magnetic field generated by the treatment coil 600 may be a stimulation zone or sub-stimulation zone. The stimulation zone may be at a level where the induced current caused by the pulsing magnetic field generated by the treatment coil 600 is above a depolarization threshold of neurons of the brain, while a sub-stimulation zone may be at a level where the induced current is below the depolarization threshold of neurons of the brain. Further, although described with reference to two activation zones and two treatment areas, the treatment coil 600 may be used to generate a magnetic field that induces more or less activation zones for more or less treatment areas of the patient (e.g., depending on the specific treatment or diagnostic procedure).

Further, it should be appreciated that in some examples, the treatment coil 600 may include additional conductive elements that may be situated around the third conductive element 660 (e.g., and/or the third and/or fourth conductive elements 660, 670 may include additional turns (e.g., amp-turns)). Further, in some examples, the second ferromagnetic component 680 and/or the third ferromagnetic component 690 may be shaped such that it covers both of the third and fourth conductive elements 660, 670. For example, the top surfaces 686, 696 of the second and third ferromagnetic components 680, 690 may extend over the top surface 663 of the third conductive element 660.

The treatment coil 600 may be configured such that the conductive elements 610, 620, 660, 670 and the ferromagnetic components 630, 680, 690 are supported relative to each other. For example, one or more of the conductive elements 610, 620, 660, 670 and the ferromagnetic components 630, 680, 690 may include one or more complementary attachment members (not shown) that are configured to enable attachment (e.g., releasable attachment) of the conductive elements 610, 620, 660, 670 to the ferromagnetic components 630, 680, 690. The one or more attachment members may be configured such that the conductive elements 610, 620, 660, 670 and the ferromagnetic components 630, 680, 690 are fixedly supported relative to each other. The one or more attachment members may be configured such that the conductive elements 610, 620, 660, 670 and the ferromagnetic components 630, 680, 690 are movable (e.g., repositionable) relative to each other.

When the conductive elements 610, 620, 660, 670 are supported by (e.g., attached to) one or more of the ferromagnetic components 630, 680, 690, the conductive elements 610, 620, 660, 670 may be electrically isolated from the ferromagnetic components 630, 680, 690, for example using a dielectric. The dielectric may be air, and the conductive elements 610, 620, 660, 670 may be spaced from (e.g., not in direct contact with) the ferromagnetic components 630, 680, 690 when the conductive elements 610, 620, 660, 670 are attached to the ferromagnetic components 630, 680, 690. The conductive elements 610, 620, 660, 670 may be attached to one or more of the ferromagnetic components 630, 680, 690 using one or more attachment members that are made of any suitable electrically isolating (e.g., dielectric) material.

FIGS. 7A-D depict an example treatment coil 700 that is configured to generate a changing magnetic field in a target anatomy of a subject, such as a human subject (not shown). The target anatomy of the subject may be, for example, brain tissue of the subject. The treatment coil 700 includes a first pair of conductive elements 710a, 710b, a second pair of conductive elements 720a, 720b, a third pair of conductive elements 760a, 760b, a fourth pair of conductive element 770a, 770b, a fifth pair of conductive elements 750a, 750b, a first ferromagnetic component 730, a second ferromagnetic component 780, a third ferromagnetic component 790, a fourth ferromagnetic component 745a, and a fifth ferromagnetic component 745b. The treatment coil 700 may be disposed proximate to the head of the subject in preparation for or during TMS treatment, for example as shown in FIG. 1. The combination of the conductive elements 710a/b, 720a/b, 750a/b, 760a/b, 770a/b and the ferromagnetic components 730, 745a/b, 780, 790 collectively may be, for example, referred to as an electromagnet. It should be appreciated that the treatment coil 700 may include more or fewer conductive elements and/or ferromagnetic components than illustrated. The conductive elements may be referred to as conductive windings.

Figure 7A:
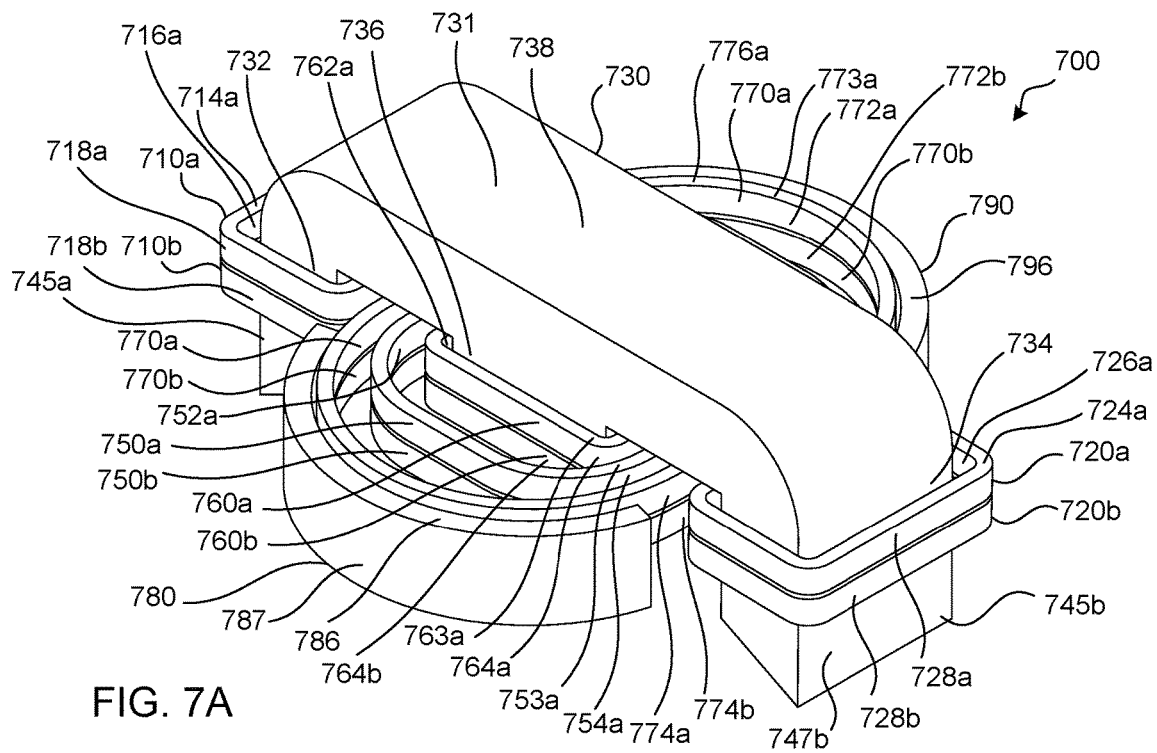
FIG. 7A is a diagram illustrating an overhead perspective of an example treatment coil that is configured to generate a changing magnetic field in a target anatomy of a subject.
Figure 7B:
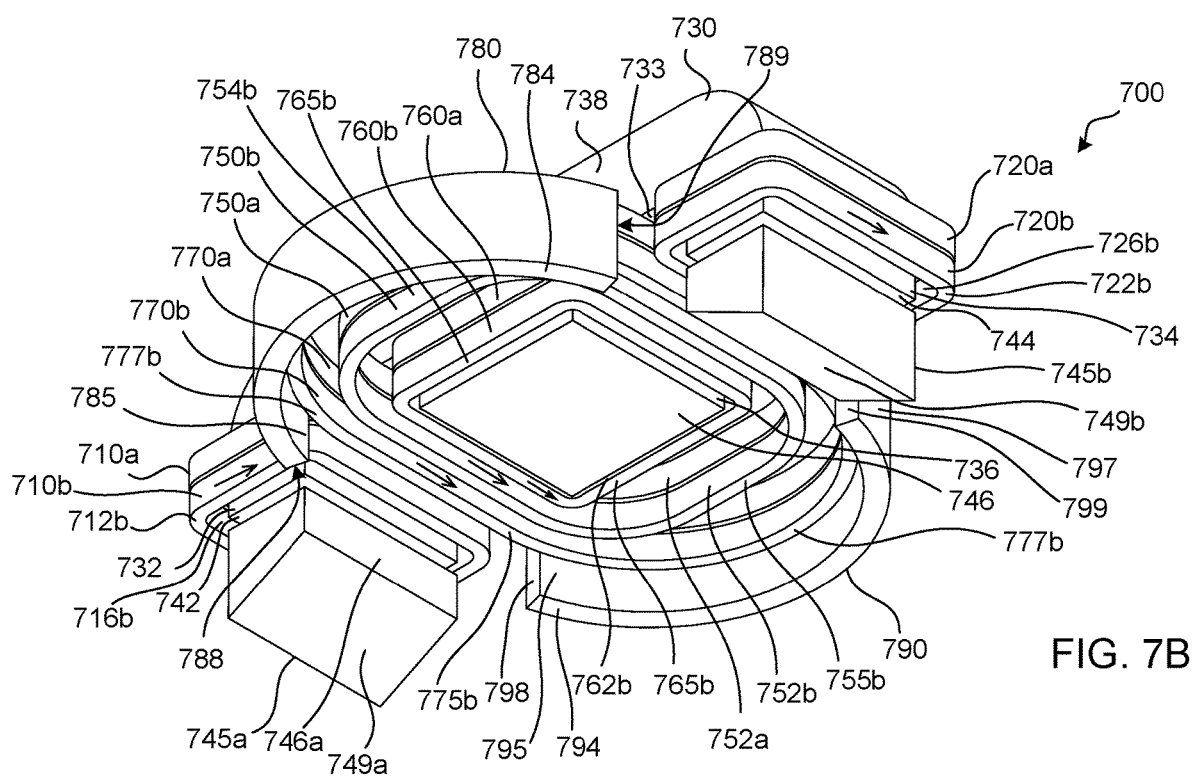
FIG. 7B is a diagram illustrating an underneath perspective of the example treatment coil of FIG. 7A that is configured to generate a changing magnetic field in a target anatomy of a subject.
Figure 7C:
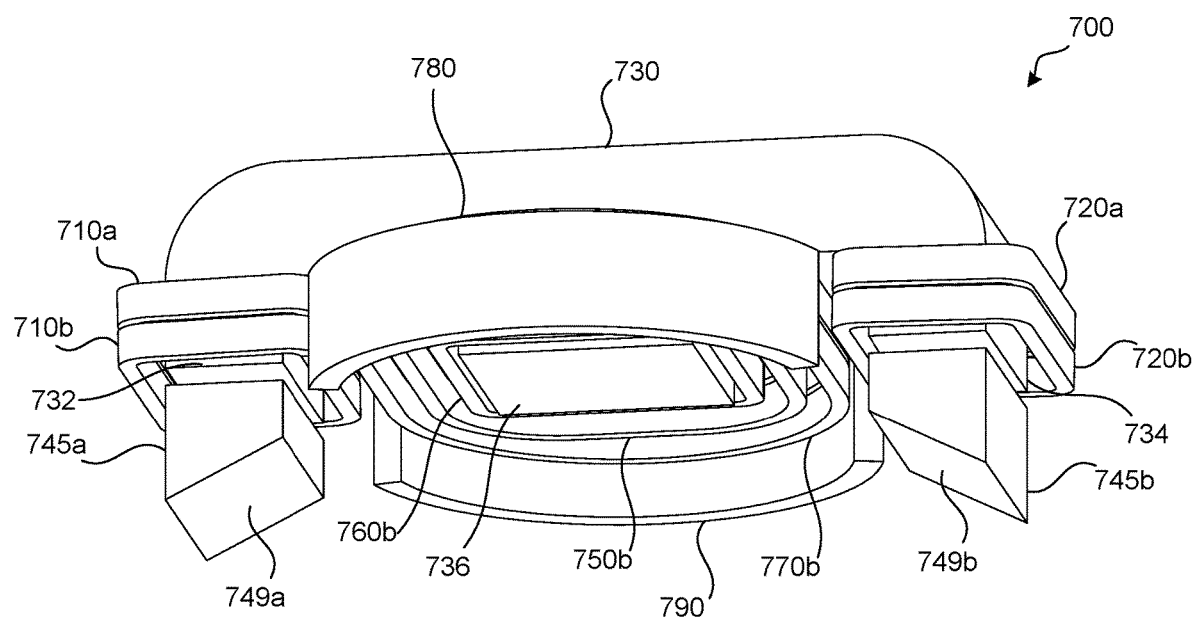
FIG. 7C is a diagram illustrating a side perspective of the example treatment coil of FIG. 7A that is configured to generate a changing magnetic field in a target anatomy of a subject.
Figure 7D:
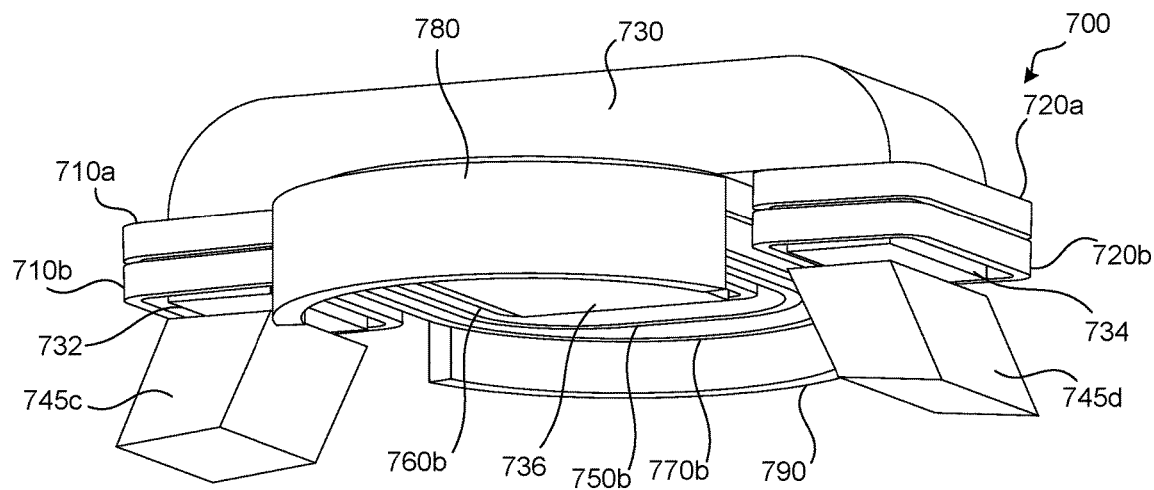
FIG. 7D is a diagram illustrating a side perspective of the example treatment coil of FIG. 7A with the inclusion of different ferromagnetic components.

FIGS. 7A-B illustrate perspective views of the treatment coil 700, while FIGS. 7C-D illustrate side views of the treatment coil 700 with the fourth and fifth ferromagnetic components 750, 755 in two different positions. The conductive elements of the first, second, third, fourth, and fifth pairs of conductive elements 710a/b, 720a/b, 760a/b, 770a/b, 750a/b may be made of any material that exhibits suitable electrical conductivity, such as copper, for example. Further, the conductive elements of each the first, second, third, fourth, and fifth pairs of conductive elements 710a/b, 720a/b, 760a/b, 770a/b, 750a/b may be parallel with one another (e.g., the top and/or bottom surface of the first conductive element 710a may be parallel with the top and/or bottom surface of the first conductive element 710b, etc.). However, it should be appreciated that in some examples, any one or more of the pairs of conductive elements 710a/b, 720a/b, 760a/b, 770a/b, 750a/b may be non-parallel.

The conductive elements of the first and second pairs of conductive elements 710a, 710b, 720a, 720b may be semi-elliptical in shape (e.g., in the shape of a rounded-rectangle). Further, in some examples, the first and second pairs of conductive elements 710a, 710b, 720a, 720b may be another shape, such as circular in shape. The first conductive element 710a may define a bottom surface, an upper surface 714a, an inner surface 716a, and an outer surface 718a. Similarly, first conductive element 710b may define a bottom surface 712b, an upper surface, an inner surface 716b, and an outer surface 718b. Further, the second conductive element 720a may define a bottom surface, an upper surface 724a, an inner surface 726a, and an outer surface 728a. And the second conductive element 722b may define a bottom surface 722b, an upper surface, an inner surface 726b, and an outer surface 728b.

The conductive elements of the third pair of conductive elements 760a, 760b may be shaped with a rounded square (e.g., substantially the same shape as the third pole face 746). Further, in some examples, the conductive elements of the third pair of conductive elements 760a, 760b may be another shape, such as circular in shape. The third conductive element 760a may define an inner surface 762a, an outer surface 764a, an upper surface 763a, and a bottom surface, while the third conductive element 760b may define an inner surface 762b, an outer surface 764b, an upper surface, and a bottom surface 765b.

Each of the conductive elements of the fourth and fifth pairs of conductive elements 770a, 770b, 750a, 750b may be semi-elliptical in shape (e.g., shaped like a rounded-rectangle). Further, in some examples, the conductive elements of the fourth and fifth pairs of conductive elements 770a, 770b, 750a, 750b may be another shape, such as circular in shape. The fourth conductive element 770a may define an inner surface 772a, an outer surface 774a, an upper surface 773a, and a bottom surface. Similarly, the fourth conductive element 770b may define an inner surface 772b, an outer surface 774b, an upper surface, and a bottom surface 775b. Further, the fifth conductive element 750a may define an inner surface 752a, an outer surface 754a, an upper surface 753a, and a bottom surface 755a. And the fifth conductive element 750b may define an inner surface 752b, an outer surface 754b, an upper surface, and a bottom surface 755b.

The upper and bottom surfaces of the conductive elements of the third pair of conductive elements 760a, 760b may be planar (e.g., flat). Similarly, the upper and bottom surfaces of the conductive elements of the fourth and fifth pairs of conductive elements 770a, 770b, 750a, 750b may be planar (e.g., flat). However, it should be appreciated that in some examples, one or more of the conductive elements of the third, fourth, or fifth pairs of conductive elements 760a, 760b, 770a, 770b, 750a, 750b may be bent or curved (e.g., bent downwards). For example, the bottom surfaces of any of the conductive elements of the third, fourth, and fifth pairs of conductive elements 760a, 760b, 770a, 770b, 750a, 750b may be concave, while the upper surfaces of any of the conductive elements of the third, fourth, and fifth pairs of conductive elements 760a, 760b, 770a, 770b, 750a, 750b may be convex. Such curvature may be designed so that the treatment coil 700 better conforms to the target anatomy (e.g., the curvature of a human head).

Further, the fifth pair of conductive elements 750a/b may define a larger circumference than the third pair of conductive elements 760a/b, and the fourth pair of conductive elements 770a/b may define a larger circumference than the fifth pair of conductive elements 750a/b. The third conductive element 760a may, at least partially, reside within an aperture of the fifth conductive element 750a and an aperture of the fourth conductive element 770a, while the third conductive element 770b may, at least partially, reside within an aperture of the fifth conductive element 750b and an aperture of the fourth conductive element 770b. Further, the fifth conductive element 750a may, at least partially, reside within the aperture of the fourth conductive element 770a, while the fifth conductive element 750b may, at least partially, reside within the aperture of the fourth conductive element 770b. Accordingly, the fourth conductive elements 770a may surround (e.g., substantially) the fifth conductive element 750a and the third conductive element 760a, while the fourth conductive elements 770b may surround (e.g., substantially) the fifth conductive element 750b and the third conductive element 760b.

Each conductive element of the first and second pairs of conductive elements 710a, 710b, 720a, 720b may define the same number of turns (e.g., amp-turns), for example, a single turn, as illustrated. Although, it should be appreciated that in some examples, any one or more of the conductive elements of the first and second pairs of conductive elements 710a, 710b, 720a, 720b may define multiple turns. Further, in some examples, the treatment coil 700 may include additional conductive elements and/or conductive elements defining more than a single loop (e.g., amp-turn).

Each of the conductive elements of the first and second pairs of conductive elements 710a, 710b, 720a, 720b may be formed of a single, monolithic piece of conductive material, or, one or more of the conductive elements of the first and second pairs of conductive elements 710a, 710b, 720a, 720b may be formed by multiple strands of wire. In some examples, the treatment coil 700 may include a housing (not shown) that houses the first, second, third, fourth, and fifth pairs of conductive elements 710a/b, 720a/b, 760a/b, 770a/b, 750a/b and the first, second, third, fourth, and fifth ferromagnetic components 730, 780, 780, 745a, 745b.

The planes defined by the upper surfaces of the first through fifth conductive elements 710a, 720a, 760a, 770a, 750a may be substantially planar with one another. Similarly, the planes defined by the bottom surfaces of the first through fifth conductive elements 710a, 720a, 760a, 770a, 750a may be substantially planar with one another. However, it should be appreciated that in some examples, the upper surfaces of any combination of conductive elements 710a, 720a, 760a, 770a, 750a and/or the bottom surfaces of any combination of conductive elements 710b, 720b, 760b, 770b, 750b may be non-planar with one another. For example, any one or more of the conductive elements 710a/b, 720a/b, 760a/b, 770a/b, 750a/b may be shifted such that its top and/or bottom surface is non-planar with the respective top and/or bottom surfaces of the other conductive elements 710a/b, 720a/b, 760a/b, 770a/b, 750a/b. For instance, in some examples, the fourth conductive element 750b may be made larger such that the bottom surface 775b of the fourth conductive element 750b may non-planar with the bottom surfaces of the other conductive elements (e.g., and, for example, be planar with a bottom surface 784, 794 of one or both of the second and third ferromagnetic components 780, 790).

The first ferromagnetic component 730 may be made of any material that exhibits suitable ferromagnetic properties, such as powdered ferromagnetic iron particles. The first ferromagnetic component 730 may comprise a main body 738 and a plurality of poles, such as a first pole 732, a second pole 734, and a third pole 736 that extends from the main body 738. Although illustrated as having three poles, in some examples, the first ferromagnetic component 730 may include more or less than three poles. The plurality of poles (e.g., the first, second, and third poles 732, 734, 736) may extend outward from the main body 738 (e.g., from a bottom surface 733 of the main body 738). The third pole 736 may reside between the first pole 732 and the second pole 734. For example, the first, second, and third poles 732, 734, 736 may be linearly aligned (e.g., as illustrated). However, it should be appreciated that in some examples, one or more of the first, second, and/or third poles 732, 734, 736 may be aligned in a non-linear manner.

The main body 738 of the first ferromagnetic component 730 may define a top surface 731 and a bottom surface 733. The top surface 731 and/or the bottom surface 733 of the main body 738 may be planar (e.g., flat). However, it should be appreciated that in some examples, the main body 738 may be curved, for example, as illustrated by the first ferromagnetic component 630 of the treatment coil 600.

The first pole 732 may define a first pole face 742, the second pole 734 may define a second pole face 744, and the third pole 736 may define a third pole face 746. The first pole 732 may be disposed within apertures defined by each of the first conductive elements 710a/b, the second pole 734 may be disposed within apertures defined by each of the second conductive elements 720a/b, and the third pole may be disposed within apertures defined by each of the third conductive elements 760a/b. Further, the third pole 736 may also reside within (e.g., partially within) apertures of the fourth and fifth conductive elements 770a/b, 750a/b. Accordingly, the third, fourth, and fifth conductive elements 760a/b, 770a/b, 750a/b may be situated such that the third pole 736 of the first ferromagnetic component 730 resides within apertures of the third, fourth, and fifth conductive elements 760a/b, 770a/b, 750a/b.

The first pole 732 may have a cross-sectional shape that is substantially similar to the shape of each of the first conductive elements 710a/b (e.g., a cross-sectional shape that is semi-elliptical), the second pole 734 may have a cross-sectional shape that is substantially similar to the shape of each of the second conductive elements 720a/b (e.g., a cross-sectional shape that is semi-elliptical), and the third pole 736 may have a cross-sectional shape that is substantially similar to the shape of each of the third conductive elements 760a/b (e.g., a cross-sectional shape that is substantially square shaped with rounded corners).

Further, in the illustrated example, the first pole face 742 may be substantially planar with the bottom surface 712b of the first conductive element 710b, the second pole face 744 may be substantially planar with the bottom surface 722b of the second conductive element 720b, and the third pole face 746 may be substantially planar with the bottom surface 762b of the third conductive element 760b. Although, it should be appreciated that in some examples, the first pole face 742 may extend beyond the plane of the bottom surface 712b of the first conductive element 710b, the second pole face 744 may extend beyond the plane of the bottom surface 722b of the second conductive element 720b, and/or the third pole face 746 may extend beyond the plane of the bottom surface 762b of the third conductive element 760b.

The second and third ferromagnetic components 780, 790 may be made of any material that exhibits suitable ferromagnetic properties, such as powdered ferromagnetic iron particles. The second ferromagnetic component 780 may define a bottom surface 784, an inner surface 785, a top surface 786, an outer surface 787, a first pole 788, and a second pole 789. Similarly, the third ferromagnetic component 790 may define a bottom surface 794, an inner surface 795, a top surface 796, an outer surface 797, a first pole 798, and a second pole 799. Each of the bottom surfaces 784, 794, the top surfaces 786, 796, the first poles 788, 798, and the second poles 789, 799 of the second and third ferromagnetic components 780, 790 may be planar (e.g., flat). Although, it should be appreciated that in some examples, one or more of the bottom surfaces 784, 794, the top surfaces 786, 796, the first poles 788, 798, and the second poles 789, 799 of the second and third ferromagnetic components 780, 790 may be curved or otherwise shaped.

The top surfaces 786, 796 of the second and third ferromagnetic components 780, 790 may be planar with a top surface 776a of the fourth conductive elements 770a. However, the bottom surfaces 784, 794 of the second and third ferromagnetic components 780, 790 may extend beyond the plane defined by a bottom surface 777b of the fourth conductive elements 770*b* (e.g., the bottom surfaces 784, 794 may non-planar with the bottom surface 777*b*). However, it should be appreciated that in some examples, one or more of the top surfaces 786, 796 and/or the bottom surfaces 784, 794 may not be planar with the top and/or bottom surfaces of the fourth conductive elements 770*a*, 770*b*, respectively.

The second and third ferromagnetic components 780, 790 may be curved. For example, the inner surfaces 785, 795 of the second and third ferromagnetic components 780, 790 may be concave, while the outer surfaces 787, 797 may be convex. For example, the curvature of the inner and outer surfaces 785, 795, 787, 797 of the second and third ferromagnetic components may be substantially similar to the curvature of the outer surface of the fourth conductive elements 770*a/b*. However, the curvature of the inner and outer surfaces 785, 795, 787, 797 of the second and third ferromagnetic components 780, 790 is not limited to that illustrated in FIGS. 7A-D.

The second and third ferromagnetic components 780, 790 may be substantially the same size and shape. However, in some examples, the second and third ferromagnetic components 780, 790 may have a different size and/or shape than illustrated. Further, in some examples, the size or shape of second ferromagnetic component 780 may be different from the size or shape of the third ferromagnetic component 790 (e.g., to shift the size and/or shape of the magnetic field generated by the treatment coil 700). Also, in some examples, one or both of the second or third ferromagnetic components 780, 790 may be omitted from the treatment coil 700.

The first and second pole faces 788, 789, 798, 799 of the second and third ferromagnetic components 780, 790 may be perpendicular with the other surfaces of the second and third ferromagnetic components 780, 790, respectively. However, it should be appreciated that in some examples, the first and second pole faces 788, 789, 798, 799 may be angled. For example, any one or more of the first and second pole faces 788, 789, 798, 799 may form acute or obtuse angles with any one or more of the other surfaces of the second and third ferromagnetic components 780, 790, respectively. For example, the first and second pole faces 788, 799 may form an obtuse angle with the top surface 786 of the second ferromagnetic component 780, and form an acute angle with the bottom surface 784 of the second ferromagnetic component 780.

The fourth and fifth ferromagnetic components 745*a*, 745*b* may be made of any material that exhibits suitable ferromagnetic properties, such as powdered ferromagnetic iron particles. The fourth ferromagnetic component 745*a* may define an inner surface 746*a*, an outer surface, a top surface, a left and right surface, and a bottom surface that defines a pole 749*a*. Similarly, the fifth ferromagnetic component 745*b* may define an inner surface, an outer surface 747*b*, a top surface, a left and right surface, and a bottom surface that defines a pole 749*b*. The upper surfaces of the fourth and fifth ferromagnetic components 745*a*, 745*b* may be of a similar size and shape (e.g., an identical size and shape) as the first and second pole faces 742, 744, respectively. Further, the upper surfaces of the fourth and fifth ferromagnetic components 745*a*, 745*b* may be parallel with the first and second pole faces 742, 744, respectively. When the treatment coil 700 is in use, the upper surfaces of the fourth and fifth ferromagnetic components 745*a*, 745*b* may be placed proximate to (e.g., and potentially secured to) the first and second pole faces 742, 744, respectively.

The poles 749*a/b* of the fourth and fifth ferromagnetic components 745*a*, 745*b* may be angled. For example, the pole face 749*a* of the fourth ferromagnetic component 745*a* may form an obtuse angle with the inner surface 746*a* of the fourth ferromagnetic component 745*a*, and form an acute angle with the outer surface of the fourth ferromagnetic component 745*a*. Similarly, the pole face 749*b* of the fifth ferromagnetic component 745*b* may form an obtuse angle with the inner surface of the fifth ferromagnetic component 745*b*, and form an acute angle with the outer surface 747*b* of the fifth ferromagnetic component 745*b*.

In some examples, the fourth and fifth ferromagnetic components 745*a*, 745*b* may be omitted from the treatment coil 700, or may be substituted for other ferromagnetic components of any desirable size and shape, such as the sixth and seventh ferromagnetic component 745*c*, 745*d* illustrated in FIG. 7D. The inner and outer surfaces of the sixth and seventh ferromagnetic component 745*c*, 745*d* may not be perpendicular with the top surface of the sixth and seventh ferromagnetic component 745*c*, 745*d* (e.g., whereas the inner and outer surfaces of the fourth and fifth ferromagnetic components 745*a*, 745*b* may be perpendicular with the top surface of the fourth and fifth ferromagnetic components 745*a*, 745*b*). The sixth and seventh ferromagnetic component 745*c*, 745*d* may be shaped differently from the fourth and fifth ferromagnetic components 745*a*, 745*b*, and as a result, the magnetic field generated by the treatment coil 700 may include an electric field in a treatment area that has a different shape.

The treatment coil 700 may be disposed so that the area where the first conductive element 710*b*, the third conductive element 760*b*, the fourth conductive element 770*b*, and the fifth conductive element 750*b* are proximate to each other (e.g., below the bottom surface 733 of the ferromagnetic component 730) may be placed above a first target area, and the area where the second conductive element 720*b*, the third conductive element 760*b*, the fourth conductive element 770*b*, and the fifth conductive element 750*b* are proximate to each other (e.g., below the opposite bottom surface 733 of the ferromagnetic component 730) may be placed above a second target area of the subject. Thereafter, the treatment coil 700 may be driven by a drive circuit of a treatment system and/or magnetic stimulation system. For example, the treatment coil 700 may be configured such that, when driven, currents circulate through the first and second conductive elements 710*a/b*, 720*a/b* in the same direction (e.g., a clockwise direction when viewed from an underneath perspective, as illustrated in FIG. 7B), and currents circulate through the third, fourth, and fifth conductive elements 760*a/b*, 770*a/b*, 750*a/b* in an opposite direction (e.g., a counter-clockwise direction when viewed from the underneath perspective, as illustrated in FIG. 7B), or vice versa.

As a result, the treatment coil 700 may be configured to generate a magnetic field that induces two activation zones, one at each of the target locations, where each of the activation zones have an elliptical shape (e.g., substantially below the area where the first conductive element 710*b*, the third conductive element 760*b*, the fourth conductive element 770*b*, and the fifth conductive element 750*b* are proximate to each other, and the area where the second conductive element 720*b*, the third conductive element 760*b*, the fourth conductive element 770*b*, and the fifth conductive element 750*b* are proximate to each other, respectively). For example, the treatment coil 700 may be configured to generate magnetic fields that induce two activation zones, while also not inducing a stimulation zone in an area under the third pole face 746.

The inclusion of the third, fourth, and fifth conductive elements 760a/b, 770a/b, 750a/b and the second and third ferromagnetic components 780, 790 may act to spread the return currents caused by the magnetic field generated by the treatment coil 700 (e.g., as compared to the treatment coil 700 without the inclusion of the third, fourth, and/or fifth conductive element 760a/b, 770a/b, 750a/b and the second and/or third ferromagnetic components 780, 790 are not included). Any combination of the third, fourth, and fifth conductive elements 760a/b, 770a/b, 750a/b and the second and third ferromagnetic components 780, 790 may be included in the treatment coil 700 to, for example, further pronounce or enhance the two activation zones created by the magnetic field (e.g., under the first and second target areas) and/or prevent the two activation zones from merging into a single activation zone (e.g., a single oval or circular shaped activation zone under the third pole face 746). For instance, the inclusion of the third, fourth, and fifth conductive elements 760a/b, 770a/b, 750a/b distorts the magnetic field generated by the treatment coil 700 by spreading the return currents to areas that are substantially under and proximate to the second and third ferromagnetic components 780, 790, and the inclusion of the second and third ferromagnetic components 780, 790 further enhances this spread of the return currents. For example, the inclusion of the third, fourth, and fifth conductive elements 760a/b, 770a/b, 750a/b may pull the return currents further away from the third pole face 746 to, for example, enhance the two activation zones and prevent a single activation zone (e.g., one big ring) from resulting. Further, the inclusion of the third and fourth conductive elements 660, 670 may make the treatment coil 600 more energy efficient when creating the two activation zones. And the inclusion of the second and third ferromagnetic components 780, 790 may cause the return currents to diverge away from the third pole face 746, which may enhance the currents inside of the two activation zones.

Stated another way, the ferromagnetic components 780, 790 may enhance the electric field generated by the treatment coil 700 by drawing the return currents out towards the respective ferromagnetic component 780, 790 when the return currents are leaving an activation zone (e.g., spreading the return currents out away from the third pole face 746) because, for example, the return currents take the path of least resistance. Without the inclusion of the ferromagnetic components 780, 790, the return currents may take a shorter path, for example, the path defined by the conductive element 760. As such, the ferromagnetic components 780, 790 may assist in ensuring that the two activation zones do not combine (e.g., merge) into one, large activation zone (e.g., a single activation zone that includes the area under the third pole face 746).

Further, the inclusion of the fourth and fifth ferromagnetic components 745a, 745b (e.g., or differently sized and/or shaped ferromagnetic components adjacent to the first and second pole faces 742, 744 of the first ferromagnetic component 730) may allow for the treatment coil 700 to shift the relative location of the two activation zones and/or adjust the shape of the two activation zones. For example, a shift in the relative location and/or the shape of the two activation zones may be desirable when treating patients whose target anatomy (e.g., head) is of differing size and/or shape. For further example, the shift in the relative location and/or the shape of the two activation zones may be desirable during different treatment and/or diagnostic procedures (e.g., when the target locations associated with the two activation zones vary). Such, configurability of the treatment coil 700 may allow for the coil 700 to be optimized for different patients and/or for different treatment/diagnostic procedures.

The treatment coil 700 may be configured such that when the conductive elements 710a/b, 720a/b, 760a/b, 770a/b, 750a/b are driven the resulting activation zone encompasses two independent areas within a brain of a subject. The areas within the brain of the subject may be correlated with different functional regions of the brain. For example, the treatment coil 700 may be used to stimulate two different areas within the brain of the subject, such as a first area located below and proximate to the pole face 749a and a second area located below and proximate to the second pole face 749b of the fourth and fifth ferromagnetic components 745a, 745b, respectively. The currents in the two areas of the brain may move in the same or different directions (e.g., clockwise and/or counter-clockwise).

The activation induced by the magnetic field generated by the treatment coil 700 may be a stimulation zone or sub-stimulation zone. The stimulation zone may be at a level where the induced current caused by the pulsing magnetic field generated by the treatment coil 700 is above a depolarization threshold of neurons of the brain, while a sub-stimulation zone may be at a level where the induced current is below the depolarization threshold of neurons of the brain. Further, although described with reference to two activation zones and two treatment areas, the treatment coil 700 may be used to generate a magnetic field that induces more or less activation zones for more or less treatment areas of the patient (e.g., depending on the specific treatment or diagnostic procedure).

The treatment coil 700 may be configured such that the conductive elements 710a/b, 720a/b, 760a/b, 770a/b, 750a/b and the ferromagnetic components 730, 780, 790, 745a, 745b are supported relative to each other. For example, one or more of the conductive elements 710a/b, 720a/b, 760a/b, 770a/b, 750a/b and the ferromagnetic components 730, 780, 790, 745a, 745b may include one or more complementary attachment members (not shown) that are configured to enable attachment (e.g., releasable attachment) of the conductive elements 710a/b, 720a/b, 760a/b, 77 a/b, 750a/b to the ferromagnetic components 730, 780, 790, 745a, 745b. The one or more attachment members may be configured such that the conductive elements 710a/b, 720a/b, 760a/b, 77 a/b, 750a/b and the ferromagnetic components 730, 780, 790, 745a, 745b are fixedly supported relative to each other. The one or more attachment members may be configured such that the conductive elements 710a/b, 720a/b, 760a/b, 77 a/b, 750a/b and the ferromagnetic components 730, 780, 790, 745a, 745b are movable (e.g., repositionable) relative to each other.

When the conductive elements 710a/b, 720a/b, 760a/b, 77 a/b, 750a/b are supported by (e.g., attached to) one or more of the ferromagnetic components 730, 780, 790, 745a, 745b, the conductive elements 710a/b, 720a/b, 760a/b, 77 a/b, 750a/b may be electrically isolated from the ferromagnetic components 730, 780, 790, 745a, 745b, for example using a dielectric. The dielectric may be air, and the conductive elements 710a/b, 720a/b, 760a/b, 77 a/b, 750a/b may be spaced from (e.g., not in direct contact with) the ferromagnetic components 730, 780, 790, 745a, 745b when the conductive elements 710a/b, 720a/b, 760a/b, 77 a/b, 750a/b are attached to the ferromagnetic components 730, 780, 790, 745a, 745b. The conductive elements 710a/b, 720a/b, 760a/b, 77 a/b, 750a/b may be attached to one or more of the ferromagnetic components 730, 780, 790, 745a, 745b using one or more attachment members that are made of any suitable electrically isolating (e.g., dielectric) material.

Figure 8A:
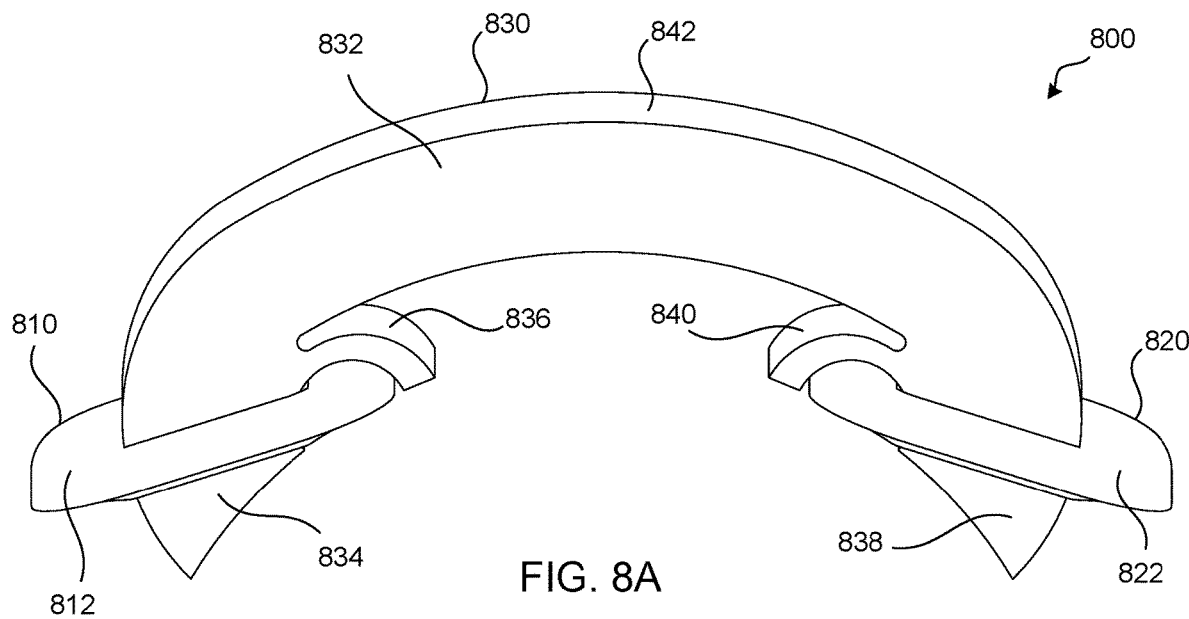
FIG. 8A is a diagram illustrating a side perspective of an example treatment coil that is configured to generate a changing magnetic field in a target anatomy of a subject.
Figure 8B:
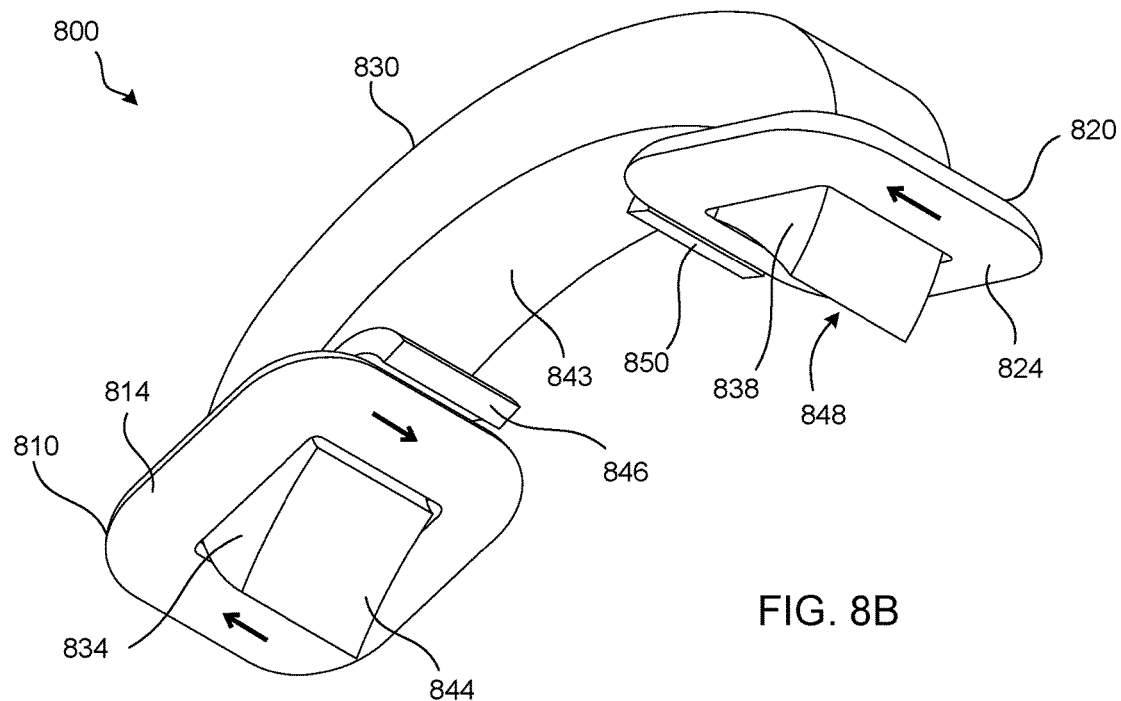
FIG. 8B is a diagram illustrating an underneath perspective of the example treatment coil of FIG. 8A that is configured to generate a changing magnetic field in a target anatomy of a subject.

FIGS. 8A and 8B depict an example treatment coil 800 that is configured to generate a changing magnetic field in a target anatomy of a subject, such as a human subject (not shown). The target anatomy of the subject may be, for example, brain tissue of the subject. The treatment coil 800 includes a first conductive element 810, a second conductive element 820, and a ferromagnetic component 830. The treatment coil 800 may be disposed proximate to the head of the subject in preparation for or during TMS treatment, for example as shown in FIG. 1. The combination of the conductive elements 810, 820 and the ferromagnetic component 830 collectively may be, for example, referred to as an electromagnet. It should be appreciated that the treatment coil 800 may include more or fewer conductive elements than illustrated. The conductive elements may be referred to as conductive windings.

The first and second conductive elements 810, 820 may be semi-elliptical in shape (e.g., having a cross-section in the shape of a rounded-square). Further, in some examples, the first and second conductive elements 810, 820 may be another shape, such as circular in shape. In some examples, the first and second conductive elements 810, 820 may, together, form a figure 8 coil or a B-shaped coil. The first conductive element 810 may define an upper surface 812 and a bottom surface 814. Similarly, the second conductive element 820 may define an upper surface 822 and a bottom surface 824. The upper surfaces 812, 822 may be rounded. For example, the upper surface 812, 822 may be convex in shape. The bottom surface 814, 824 may be arched. For example, the bottom surfaces 814, 824 may be concave in shape. Although illustrated as convex and concave in shape, any one or more of the upper and bottom surfaces of the first and second conductive elements 810, 820 may be planar (e.g., flat). Further, in such examples, the first and/or second conductive element 810, 820 may define one or more sides. The first and second conductive elements 810, 820 may be made of any material that exhibits suitable electrical conductivity, such as copper, for example.

The first and second conductive elements 810, 820 may define the same number of turns (e.g., amp-turns), for example, a single turn, as illustrated. Although, it should be appreciated that in some examples, the first conductive element 810 and/or the second conductive element 820 may define multiple turns. For instance, in some examples, the first conductive element 810 may define a first number of turns, while the second conducive element 820 may define a different, second number of turns. Further, in some examples, the treatment coil 800 may include additional conductive elements and/or conductive elements defining more than a single loop (e.g., amp-turn). For example, the first conductive element 810 may include one or more additional and overlapping conductive elements (e.g., the first conductive element 810 may define more than a single loop) and/or the second conductive element 820 may include one or more additional and overlapping conductive elements (e.g., the second conductive element 820 may define more than a single loop).

The first conductive element 810 and/or the second conductive element 820 may be formed of a single, monolithic piece of conductive material, or, one or more of the first and second conductive elements 810, 820 may be formed by multiple strands of wire. In some examples, the treatment coil 800 may include a housing (not shown) that houses the first and second conductive winding 810, 820 and the ferromagnetic component 830.

The ferromagnetic component 830 may be made of any material that exhibits suitable ferromagnetic properties, such as powdered ferromagnetic iron particles. The ferromagnetic component 830 may comprise a main body 838 and a plurality of poles, such as a first pole 834, a second pole 836, a third pole 838, and a fourth pole 840 that extend from the main body 832. Although illustrated as having four poles, in some examples, the ferromagnetic component 830 may include more or less than four poles. The second pole 836 may reside between the first pole 834 and the fourth pole 840, and the fourth pole 810 may reside between the second pole 836 and the third pole 838. For example, the first, second, third, and fourth poles 834, 836, 838, 840 may be linearly aligned (e.g., as illustrated). However, it should be appreciated that in some examples, one or more of the first, second, third, and fourth poles 834, 836, 838, 840 may be aligned in a non-linear manner.

The first pole 834 and the third pole 838 may extend outward from the main body 832 (e.g., from a bottom surface 843 of the main body 832). The second pole 836 may extend from the first pole 834 (e.g., extend from an inner side of the first pole 834), and the fourth pole 840 may extend from the third pole 838 (e.g., extend from an inner side of the third pole 838). Although, it should be appreciated that in some example, one or more of the second and fourth poles 836, 840 may extend outward from the main body 832 (e.g., from the bottom surface 843 of the main body 832).

The main body 832 of the ferromagnetic component 830 may define a top surface 842 and a bottom surface 843. The main body 832 may be curved, for example, as illustrated. For example, the top surface 842 of the main body 832 may define a convex surface, while the bottom surface 843 of the main body 832 may define a concave surface. Accordingly, the top surface 842 may be non-planar, and the bottom surface 843 may be non-planar. Further, it should be appreciated that in some examples, the curvature of the top and/or bottom surface 842, 843 of the main body 832 may define a greater or lesser curvature than illustrated. Moreover, it should be appreciated that in some examples, the top surface 842 and/or the bottom surface 843 of the main body 832 may be planar (e.g., flat).

The first pole 834 may define a first pole face 844, the second pole 836 may define a second pole face 846, the third pole 838 may define a third pole face 848, and the fourth pole 840 may define a fourth pole face 850. The first pole face 844 and the third pole face 848 may define concave surfaces (e.g., having similar concave curvatures as the bottom surfaces 814, 824 of the first and second conductive elements 810, 820). The first pole 834 may be disposed within an aperture of the first conductive element 810, and the third pole 838 may be disposed within an aperture of the second conductive element 820. The first pole 834 may have a cross-sectional shape that is substantially similar to the shape of the first conductive element 810 (e.g., a cross-sectional shape that is shaped like a rounded square), and the third pole 838 may have a cross-sectional shape that is substantially similar to the shape of the second conductive element 820 (e.g., a cross-sectional shape that is shaped like a rounded square).

Further, in the illustrated example, the first pole face 844 may extend beyond the bottom surface 814 of the first conductive element 810, and the third pole face 848 may extend beyond the bottom surface 824 of the second conductive element 820. Specifically, the first pole face 844 and the bottom surface 814 of the first conductive element 810 may not be parallel with one another, and the third pole face 848 and the bottom surface 824 of the second conductive element 820 may not be parallel with one another. However, in some examples, the first pole 834 and/or the third pole 838 may extend through the first and second conductive elements 810, 820 respectively, such that the first pole face 844 and the bottom surface 814 are parallel (e.g., concentric curvatures) with one another and/or the third pole face 848 and the bottom surface 824 are parallel (e.g., concentric curvatures) with one another. Further, it should be appreciated that in some examples, the first pole face 844 may be substantially planar with the bottom surface 814 of the first conductive element 810, and/or the third pole face 848 may be substantially planar with the bottom surface 824 of the second conductive element 820.

The second pole 836 and/or the fourth pole 850 may be hook shaped (e.g., as illustrated). The second pole 836 and/or the fourth pole 850 may wrap around (e.g., at least partially, for example, as illustrated) the first and second conductive elements 810, 820, respectively. For example, the second pole 836 may extend from the first pole 834 and may wrap around the upper surface 812 of the first conductive element 810. For example, the second pole 836 may be sized and shaped such that the second pole face 846 may be substantially planar with the bottom surface 814 of the first conductive element (e.g., the second pole face 846 may reside in a plane where the top and bottom surfaces 812, 814 meet). Similarly, the fourth pole 840 may extend from the third pole 838 and may wrap around the upper surface 822 of the second conductive element 820. For example, the fourth pole 840 may be sized and shaped such that the fourth pole face 850 may be substantially planar with the bottom surface 824 of the second conductive element 820 (e.g., the fourth pole face 850 may reside in a plane where the top and bottom surfaces 822, 824 meet). However, it should be appreciated that in some examples, the second pole 836 and/or the fourth pole 850 may be sized and shaped such that their respective pole faces may be situated differently.

Although not illustrated, in some examples, the ferromagnetic component 830 may be configured to be adjustable (e.g., the curvature of the ferromagnetic component 830 may be adjustable), for example, relative to the anatomy of the subject's head. For example, the ferromagnetic component 830 may include multiple pieces, such that one or more pieces of the ferromagnetic component 830 may be configured so as to be adjustable relative to one or more other pieces of the ferromagnetic component 830, and/or two or more of the pieces of the ferromagnetic component 830 may be configured to be adjustable (e.g., pivotally adjustable) relative to each other (e.g., through the use of a hinge between the pieces of the ferromagnetic component 830).

The treatment coil 800 may be configured to be driven such that the treatment coil 800 can be used to treat multiple (e.g., two) target areas of a subject. For example, during a treatment or diagnostic procedure, the treatment coil 800 may be disposed so that the area where the first conductive element 810 wraps between the first pole face 844 and the second pole face 846 may be placed above a first target area, and the area where the second conductive element 820 wraps between the third pole face 848 and the fourth pole face 850 may be placed above a second target area of the subject. Thereafter, the treatment coil 800 may be driven by a drive circuit of a treatment system and/or magnetic stimulation system. For example, the treatment coil 800 may be configured such that, when driven, currents circulate through the first conductive element 810 in a first direction (e.g., a clockwise direction when viewed from an underneath perspective, as illustrated in FIG. 8B), and currents circulate through the second conductive element 820 in a second, opposite direction (e.g., a counter-clockwise direction when viewed from an underneath perspective, as illustrated in FIG. 8B), or vice versa.

As a result, the treatment coil 800 may be configured to generate a magnetic field that induces two activation zones, one at each of the target locations. The activation zones may define a semi-elliptical shape (e.g., substantially below the area where the first conductive element 810 wraps between the first pole face 844 and the second pole face 846, and the area where the second conductive element 820 wraps between the third pole face 848 and the fourth pole face 850, respectively). For example, the treatment coil 800 may be configured to generate magnetic fields that induce two activation zones, while also not inducing a stimulation zone in an area under the center of the body 843 of the ferromagnetic component 830.

Further, it should be appreciated that the inclusion of the second and fourth poles 836, 840 of the ferromagnetic component 830 may act to create two activation zones that are more localized and separated than the simulation zones that would be created by a similar treatment coil that included the ferromagnetic component 830 without the second and fourth poles 836, 840. Accordingly, the second and fourth poles 836, 840 act to further accentuate the two activation zones generated by the treatment coil 800. That is, the second and fourth poles 836, 840 may enhance or further pronounce the two activation zones, where, for example, the bigger and/or thicker the second and fourth poles 836, 840 are made, the more pronounced the two activation zones become (e.g., bigger and/or thicker second and fourth poles 836, 840 assist in creating a stronger gradient for the electric field caused by the magnetic field generated by the treatment coil 800). Further, the two activation zones generated by the treatment coil 800 may be mirror images of one another.

As illustrated, the treatment coil 800 may be configured to generate a magnetic field that includes an electric field in the two activation zones are parallel to each other. However, it should be appreciated that in some examples, the treatment coil 800 may be configured such that it generates a magnetic field that includes an electric field in the two activation zones are not parallel to each other. For example, one or more of the poles 834, 836, 838, 840 of the treatment coil 800 may be aligned such that a center of the pole(s) is not parallel with one or more of the other poles 834, 836, 838, 840 of the treatment coil 800. For instance, the first and second poles 834, 836 may be parallel with one another, but not parallel with the third and fourth poles 838, 840.

The treatment coil 800 may be configured such that when the first and second conductive elements 810, 820 are driven the resulting activation zone encompasses two independent areas within a brain of a subject. The areas within the brain of the subject may be correlated with different functional regions of the brain. For example, the treatment coil 800 may be used to stimulate two different areas within the brain of the subject, such as a first area located below and proximate to the first conductive element 810 and a second area located below and proximate to the second conductive element 820. The currents in the two areas of the brain may move in the same or different directions (e.g., clockwise and/or counter-clockwise).

The activation zones induced by the magnetic field generated by the treatment coil 800 may be stimulation zones or sub-stimulation zones. A stimulation zone may be at a level where the induced current caused by the pulsing magnetic field generated by the treatment coil 800 is above a depolarization threshold of neurons of the brain, while a sub-stimulation zone may be at a level where the induced current is below the depolarization threshold of neurons of the brain. Further, although described with reference to two activation zones and two treatment areas, the treatment coil 800 may be used to generate a magnetic field that induces more or less activation zones for more or less treatment areas of the patient (e.g., depending on the specific treatment or diagnostic procedure).

The treatment coil 800 may be configured such that the conductive elements 810, 820 and the ferromagnetic component 830 are supported relative to each other. For example, the treatment coil 800 may be configured such that the ferromagnetic component 530 supports the conductive elements 810, 820. One or both of the conductive elements 810, 820 and the ferromagnetic component 830 may include one or more complementary attachment members (not shown) that are configured to enable attachment (e.g., releasable attachment) of the conductive elements 810, 820 to the ferromagnetic component 830. The one or more attachment members may be configured such that the conductive elements 810, 820 and the ferromagnetic component 830 are fixedly supported relative to each other. The one or more attachment members may be configured such that the conductive elements 810, 820 and the ferromagnetic component 830 are movable (e.g., repositionable) relative to each other.

When the conductive elements 810, 820 are supported by (e.g., attached to) the ferromagnetic component 830, the conductive elements 810, 820 may be electrically isolated from the ferromagnetic component 830, for example using a dielectric. The dielectric may be air, and the conductive elements 810, 820 may be spaced from (e.g., not in direct contact with) the ferromagnetic component 830 when the conductive elements 810, 820 are attached to the ferromagnetic component 830. The conductive elements 810, 820 may be attached to the ferromagnetic component 830 using one or more attachment members that are made of any suitable electrically isolating (e.g., dielectric) material.

Figure 9A:
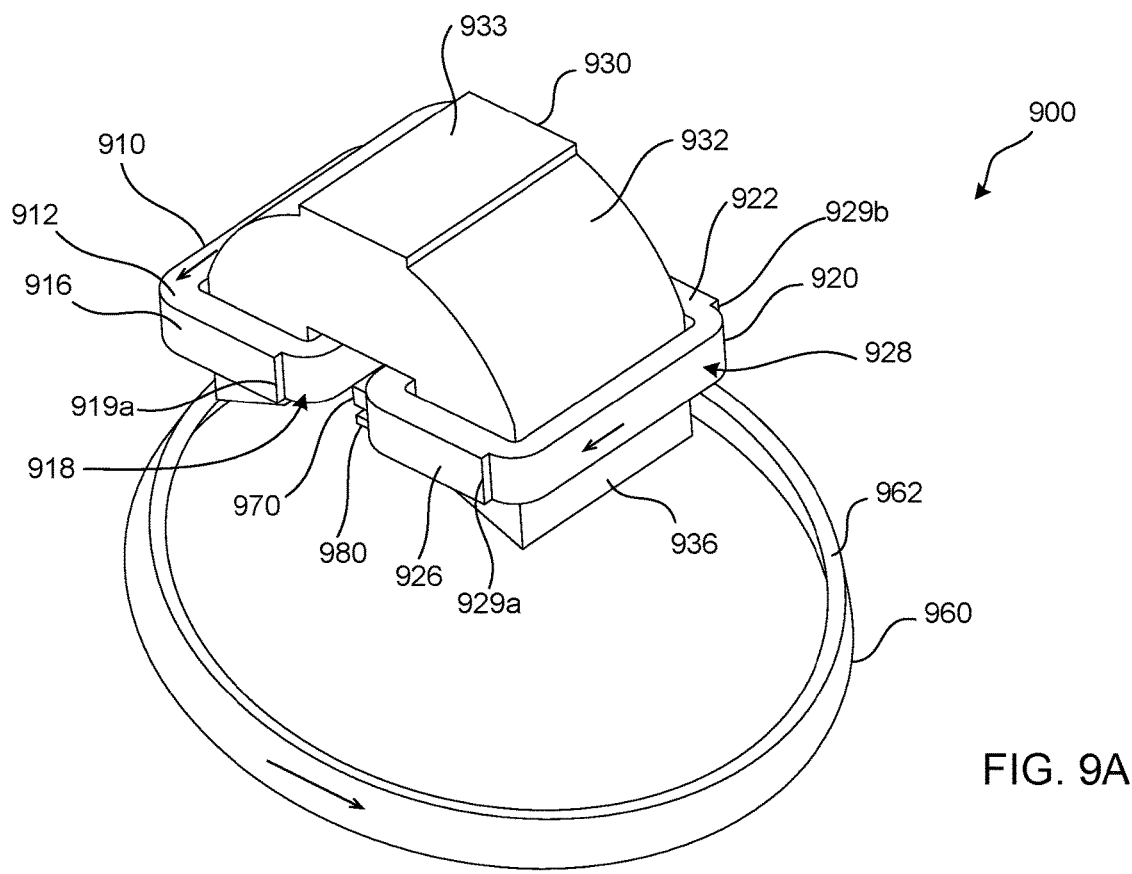
FIG. 9A is a diagram illustrating an overhead perspective of an example treatment coil that is configured to generate a changing magnetic field in a target anatomy of a subject.
Figure 9B:
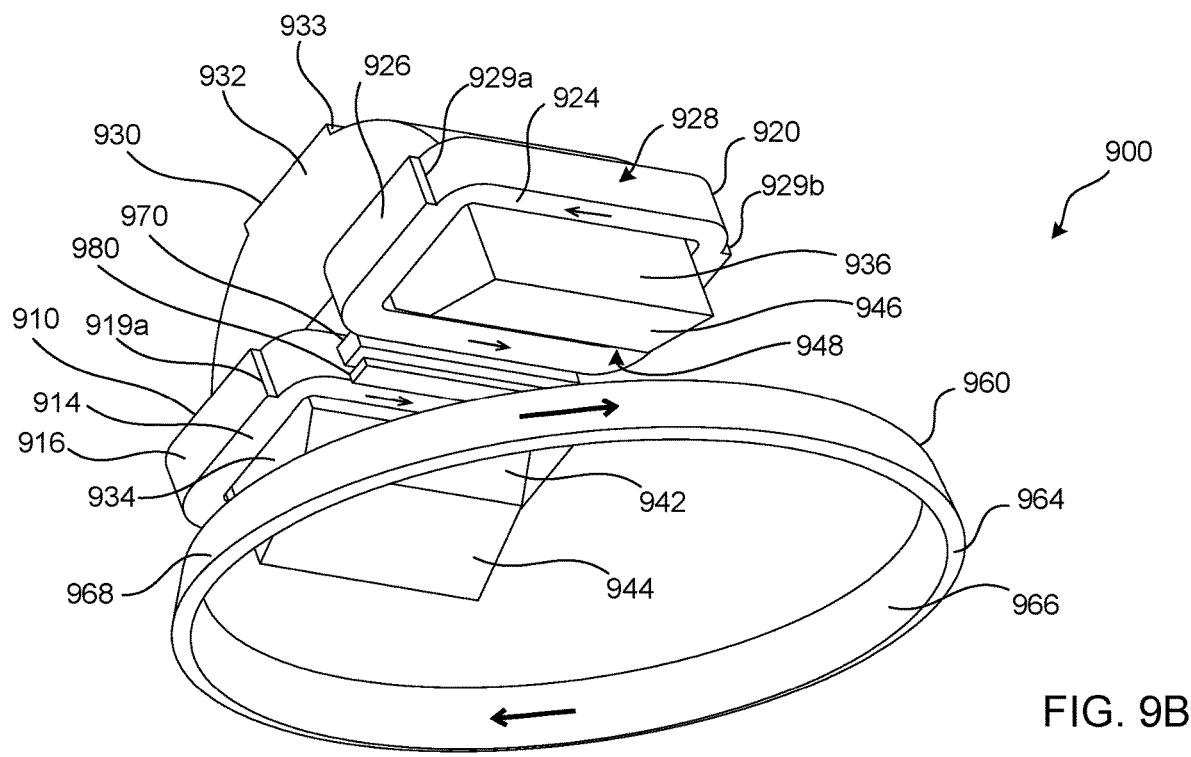
FIG. 9B is a diagram illustrating an underneath perspective of the example treatment coil of FIG. 9A that is configured to generate a changing magnetic field in a target anatomy of a subject.

FIGS. 9A and 9B depict an example treatment coil 900 that is configured to generate a changing magnetic field in a target anatomy of a subject, such as a human subject (not shown). The target anatomy of the subject may be, for example, brain tissue of the subject. The treatment coil 900 includes a first conductive element 910, a second conductive element 920, a third conductive element 960, a first ferromagnetic component 930, a second ferromagnetic component 970, and a third ferromagnetic component 980. The treatment coil 900 may be disposed proximate to the head of the subject in preparation for or during TMS treatment, for example as shown in FIG. 1. The combination of the conductive elements and the ferromagnetic component of the treatment coil 900 collectively may be, for example, referred to as an electromagnet. It should be appreciated that the treatment coil 900 may include more or fewer conductive elements and/or ferromagnetic components than illustrated (e.g., one or both of the ferromagnetic components 970, 980 may be omitted). The conductive elements may be referred to as conductive windings. The first, second, and third conductive elements 910, 920, 960 may be made of any material that exhibits suitable electrical conductivity, such as copper, for example.

The first and second conductive elements 910, 920 may be semi-elliptical in shape (e.g., in the shape of a rounded-rectangle). Further, in some examples, the first and second conductive elements 910, 920 may be another shape, such as circular in shape. In some examples, the first and second conductive elements 910, 920 may, together, form a figure 8 coil or a B-shaped coil. The first conductive element 910 may define an upper surface 912, a bottom surface 914, an inner surface, and an outer surface 916. Similarly, the second conductive element 920 may define an upper surface 922, a bottom surface 924, an inner surface, and an outer surface 926. The outer surface 916 of the first conductive element 910 may define a recess 918 (e.g., an indentation), a first ledge 919a and a second ledge (not shown), where the recess 918 may extend between the first and second ledges of the outer surface 916. Similarly, the outer surface 926 of the second conductive element 920 may define a recess 928, a first ledges 929a and a second ledge 929b, where the recess 928 may extend between the first and second ledges 929a, 929b of the outer surface 926. Further, the treatment coil 900 may be configured such that the first recess 918 resides proximate to the second conductive element 920 (e.g., as illustrated), and the second recess 928 resides along the outside of the treatment coil 900 (e.g., further away from the first conductive element). However, it should be appreciated that the first and second conductive elements 910, 920 may be situated such that their respective recesses 918, 928 reside anywhere around the first and second poles 934, 936 of the first ferromagnetic component 930.

The third conductive element 960 may be circular in shape. Further, in some examples, the third conductive element 960 may be another shape, such as elliptical. The third conductive element 960 may define an upper surface 962, a bottom surface 964, an inner surface 966, and an outer surface 968. The third conductive element 960 may be shaped like a circular truncated cone. For example, the upper surface 962 may define a first circumference and the bottom surface 964 may define a second circumference, and the second circumference may be greater than the first circumference. However, it should be appreciated that in some examples, the upper and bottom surfaces 962, 964 may define the same circumference. Further, it should be appreciated that in some examples, the third conductive element 960 may include one or more bends or kinks. For example, the third conductive element 960 may be bent so that the upper and bottom surfaces 962, 964 of the third conductive element 960 are not planar (e.g., flat). For example, the third conductive element 960 may be bent so that the upper and bottom surfaces 962, 964 each define an acute angle (e.g., so that the third conductive element 960 has a cross-sectional shape of a "V").

The first, second, and third conductive elements 910, 920, 960 may define the same number of turns (e.g., amp-turns), for example, a single turn, as illustrated. Although, it should be appreciated that in some examples, the first conductive element 910, the second conductive element 920, and/or the third conductive element 960 may define multiple turns. For instance, in some examples, any combination of the conductive elements 910, 920, 960 may define a different number of turns (e.g., the third conductive element 960 may define multiple turns while the first and second conductive elements 910, 920 define a single turn). Further, in some examples, the treatment coil 900 may include additional conductive elements and/or conductive elements defining more than a single loop (e.g., amp-turn).

The first conductive element 910, the second conductive element 920, and/or the third conductive element 960 may be formed of a single, monolithic piece of conductive material, or, one or more of the first, second, and third conductive elements 910, 920, 960 may be formed by multiple strands of wire. In some examples, the treatment coil 900 may include a housing (not shown) that houses the conductive elements 910, 920, 960 and the ferromagnetic components 930, 970, 980.

The first ferromagnetic component 930 may be made of any material that exhibits suitable ferromagnetic properties, such as powdered ferromagnetic iron particles. The first ferromagnetic component 930 may comprise a main body 932 and a plurality of poles, such as a first pole 934 and a second pole 936 that extend from the main body 932. Although illustrated as having two poles, in some examples, the first ferromagnetic component 930 may include more or less than two poles. The plurality of poles (e.g., the first and second poles 934, 936) may extend outward from the main body 932 (e.g., from a bottom surface of the main body 932).

The main body 932 of the first ferromagnetic component 930 may define a projection 933 that extends upward from a top surface of the main body 932. Although illustrated with the projection 933, in some example, the first ferromagnetic component 930 may not include the projection 933. The main body 932 may be curved, for example, as illustrated. For example, the top surface of the main body 932 may define a convex surface, while the bottom surface of the main body may define a planar surface (e.g., a flat surface). Accordingly, the top surface may be non-planar, and the bottom surface may be planar. Further, it should be appreciated that in some examples, the curvature of the top and/or bottom surface of the main body 932 may define a greater or lesser curvature than illustrated (e.g., the bottom surface may be curved). Moreover, it should be appreciated that in some examples, the top surface of the main body 932 may be planar (e.g., flat).

The first and second poles 934, 936 may define one or more pole faces. For example, the first pole 934 may define a first pole face 942 and a second pole face 944, and the second pole 936 may define a third pole face 946 and a fourth pole face 948. The first pole 934 may be disposed within an aperture of the first conductive element 910, and the second pole 936 may be disposed within an aperture of the second conductive element 920. The first pole 934 may have a cross-sectional shape that is substantially similar to the shape of the first conductive element 910 (e.g., a cross-sectional shape that is semi-elliptical), and the second pole 936 may have a cross-sectional shape that is substantially similar to the shape of the second conductive element 920 (e.g., a cross-sectional shape that is semi-elliptical).

The first pole face 942 and the second pole face 944 may be angularly offset from one another (e.g., not perpendicular, such as defining an obtuse angle, as illustrated). Similarly, the third pole face 946 and the fourth pole face 948 may be angularly offset from one another (e.g., not perpendicular, such as defining an obtuse angle, as illustrated). The first and second pole faces 942, 944 may be angled towards the third and fourth poles faces 946, 948. For example, a central axis of the first pole face 942 may intersect a central axis of the third pole face 946 (e.g., directly below the center of the body 932), while a central axis of the second pole face 944 may intersect a central axis of the fourth pole face 948 (e.g., directly below the center of the body 932).

Further, in the illustrated example, the first and second pole faces 942, 944 may extend beyond the plane of the bottom surface 914 of the first conductive element 910, and the third and fourth pole faces 946, 948 may extend beyond the plane of the bottom surface 924 of the second conductive element 920. Although, it should be appreciated that in some examples, the one or more of the first and/or second poles 934, 936 may define a single pole, and the single pole may be substantially planar with the bottom surface 914, 924 of the first or second conductive elements 910, 920, respectively.

Although not illustrated, in some examples, the first ferromagnetic component 930 may be configured to be adjustable (e.g., the curvature of the first ferromagnetic component 930 may be adjustable), for example, relative to the anatomy of the subject's head. For example, the first ferromagnetic component 930 may include multiple pieces, such that one or more pieces of the first ferromagnetic component 930 may be configured so as to be adjustable relative to one or more other pieces of the first ferromagnetic component 930, and/or two or more of the pieces of the first ferromagnetic component 930 may be configured to be adjustable (e.g., pivotally adjustable) relative to each other (e.g., through the use of a hinge between the pieces of the first ferromagnetic component 930).

The treatment coil 900 may also include the second and third ferromagnetic components 970, 980. The second and third ferromagnetic components 970, 980 may be linear shaped (e.g., having a cross-sectional shape of an elongated rectangle). The second and third ferromagnetic components 970, 980 may be disposed between the first and second poles 934, 936 of the first ferromagnetic component 930 (e.g., and between the first and second conductive elements 910, 920). The second and third ferromagnetic components 970, 980 may be used to alter the shape of the magnetic field (e.g., lower the field deeper into the head of the patient) generated by the treatment coil 900 (e.g., as compared to the magnetic field generated by the treatment coil 900 without the inclusion of the second and third ferromagnetic components 970, 980). Further, the second and third ferromagnetic components 970, 980 may also improve the electrical shielding of the treatment coil 900 and/or reduce surface proximate stimulation caused by the magnetic field generated by the treatment coil 900 (e.g., as compared to the magnetic field generated by the treatment coil 900 without the inclusion of the second and third ferromagnetic components 970, 980).

The third conductive element 960 may be referred to as an external conductive element or halo conductive element, for example, because the third conductive element 960 may be configured to go around a coronal plane of the patient. Further, the first and second conductive elements 910, 920 and the ferromagnetic components 930, 970, 980 may be configured such that they reside above an aperture of the third conductive element 960. As such, the third conductive element 960 may be considered to be external to the rest of the treatment coil 900. For example, a respective central axis of any combination (e.g., including all) of the first and second conductive elements 910, 920 and the first and second poles 934, 936 (e.g., one or more of the pole faces 942, 944, 946, 948 of the first and second poles 934, 936) may pass through the aperture of the third conductive element 960.

Further, the first and second conductive elements 910, 920 may be disposed such that they are asymmetrically offset from a central axis of the third conductive element 960. For example, the first and second conductive elements 910, 920 and the ferromagnetic components 930, 970, 980 may be offset from the central axis of the third conductive element 960. That is, the treatment coil 900 may be configured such that the first conductive element 910 resides closer to the third conductive element 960 than the second conductive element 920 resides to the third conductive element 960. For example, a central axis of the first conductive element 910 may be closer to the third conductive element 960 than a central axis of the second conductive element 920 is to the third conductive element 960. Accordingly, as will be discussed in more detail herein, the third conductive element 960 may act to spread return currents and reduce currents outside of the activation zones (e.g., reduce surface proximate stimulation, for example, around the eyes, sinuses, etc. during a TMS procedure).

The treatment coil 900 may be configured to be driven such that the treatment coil 900 can be used to treat multiple (e.g., two) target areas of a subject. For example, during a treatment or diagnostic procedure, the treatment coil 900 may be disposed so that the area where the first conductive element 910 is proximate to the third conductive element 960 may be placed above a first target area of the subject. For instance, the treatment coil 900 may be disposed so that the area where the outer surface 916 of the first conductive element 910 is proximate to an inner surface 966 of the third conductive element 960 may be placed above the first target area of the subject. Further, the treatment coil 900 may be disposed so that the area under the second and third ferromagnetic components 970, 980 may be placed above a second target area. Thereafter, the treatment coil 900 may be driven by a drive circuit of a treatment system and/or magnetic stimulation system. For example, the treatment coil 900 may be configured such that, when driven, currents circulate through the first and third conductive elements 910, 960 in the one direction (e.g., a clockwise direction when viewed from an underneath perspective, as illustrated in FIG. 9B), while currents circulate through the second conductive element 920 is an opposite direction (e.g., a counter-clockwise direction when viewed from an underneath perspective, as illustrated in FIG. 9B).

As a result, the treatment coil 900 may be configured to generate a magnetic field that induces two activation zones, one at each of the target locations. The first activation zone may define an elongated oval shape (e.g., substantially below the area where the outer surface 916 of the first conductive element 910 is proximate to an inner surface 966 of the third conductive element 960). The second activation zone may define a semi-elliptical shape substantially (e.g., below the second and third ferromagnetic components 970, 980). For example, the first activation zone may define a stretched-out rounded-rectangle shape, for example, a rounded-rectangular shape that is stretched along a curvature defined by the curvature of the third conductive element 960. The treatment coil 900 may be configured to create two activation zones, and may be configured to do so by ensuring that the return currents for both of the activation zones are on one side of the treatment coil 900. For example, the return currents of the conductive elements 910, 920, 960 may be situated proximate to each other, while the activation zones are also located proximate to each other). For instance, the treatment coil 900 may be driven such that the return currents reside proximate to an area below the bottom surface 964 and/or an outer surface 968 of the third conductive element 960 and proximate to an area below the recess 928 of the second conductive element 920 (e.g., the return currents are both situation on one side of the treatment coil 900), while, for example, the activation areas may be proximate to the two target areas described above. Further, it should be appreciated that the inclusion of the ferromagnetic components 970, 980 may act to further separate or pronounce the two activation zones.

Moreover, it should be appreciated that the treatment coil 900 may be configured to generate magnetic fields that induce two activation zones, while also not inducing a stimulation zone in an area between the first and second activation zones. Further, the treatment coil 900 may also be configured to not induce a stimulation zone in an area that is below the bottom surface 964 and/or an outer surface 968 of the third conductive element 960. That is, the treatment coil 900 may be configured to induce multiple activation zones within and/or under the aperture defined by the third conductive element 960, but not induce a stimulation zone outside of the area below the aperture of the third conductive element 960.

Further, it should be appreciated that, due in part to the offset of the first and second conductive elements 910, 920 and the ferromagnetic components 930, 970, 980 from the central axis of the third conductive element 960, the third conductive element 960 may act to spread return currents and reduce currents outside of the activation zones (e.g., reduce surface proximate stimulation, for example, around the eyes, sinuses, etc. during a TMS procedure). For instance, the combination of the first and second conductive elements 910, 920 and the ferromagnetic components 930, 970, 980 may be configured to be tilted towards the third conductive element 960 to generate the first activation zone (e.g., where the currents are going in the same direction) and tilted away from the third conductive element 960 on the opposite side (e.g., where the currents are in opposite directions, for example, so the currents are not fighting each other).

The treatment coil 900 may be used in a variety of treatment and diagnostic procedures. For instance, the treatment coil 900 may be used to stimulate the frontal pole above each of the eyes of a patient. In such instances, it is desirable to avoid having current flowing through the eye sockets or the sinuses of the patient. In some examples, the third conductive element 960 may be disposed around the patient's head like a headband, the area where the first conductive element 910 is proximate to the third conductive element 960 may be placed above the frontal pole of one of the eyes of the subject, and the area under the second and third ferromagnetic components 970, 980 may be placed above the frontal pole of the other o of the eyes of the subject.

The treatment coil 900 may be configured such that when the conductive elements are driven the resulting activation zone encompasses two independent areas within a brain of a subject. The areas within the brain of the subject may be correlated with different functional regions of the brain. For example, the treatment coil 900 may be used to stimulate two different areas within the brain of the subject, such as a first area located below and proximate to the first conductive element 910 and a second area located below and proximate to the area where the first conductive element 910 is proximate to the third conductive element 960. The currents in the two areas of the brain may move in the same or different directions (e.g., clockwise and/or counter-clockwise).

The activation zone induced by the magnetic field generated by the treatment coil 900 may be a stimulation zone or sub-stimulation zone. The stimulation zone may be at a level where the induced current caused by the pulsing magnetic field generated by the treatment coil 900 is above a depolarization threshold of neurons of the brain, while a sub-stimulation zone may be at a level where the induced current is below the depolarization threshold of neurons of the brain. Further, although described with reference to two activation zones and two treatment areas, the treatment coil 900 may be used to generate a magnetic field that induces more or less activation zones for more or less treatment areas of the patient (e.g., depending on the specific treatment or diagnostic procedure).

The treatment coil 900 may be configured such that the conductive elements 910, 920, 960 and the ferromagnetic components 930, 970, 980 are supported relative to each other. For example, the treatment coil 900 may be configured such that the first ferromagnetic component 930 supports the conductive elements 910, 920, 960 and the second and third ferromagnetic components 970, 980. One or more of the conductive elements 910, 920, 960 and the ferromagnetic components 930, 970, 980 may include one or more complementary attachment members (not shown) that are configured to enable attachment (e.g., releasable attachment) of the conductive elements 910, 920, 960 and the second and third ferromagnetic components 970, 980 to the first ferromagnetic component 930. The one or more attachment members may be configured such that the conductive elements 910, 920, 960 and the ferromagnetic components 930, 970, 980 are fixedly supported relative to each other. The one or more attachment members may be configured such that the conductive elements 910, 920, 960 and the ferromagnetic components 930, 970, 980 are movable (e.g., repositionable) relative to each other.

When the conductive elements 910, 920, 960 and the second and third ferromagnetic components 970, 980 are supported by (e.g., attached to) the first ferromagnetic component 930, the conductive elements 910, 920, 960 may be electrically isolated from the ferromagnetic components 930, 970, 980 for example using a dielectric. The dielectric may be air, and the conductive elements 910, 920, 960 may be spaced from (e.g., not in direct contact with) the ferromagnetic components 930, 970, 980 when the conductive elements 910, 920, 960 are attached to the ferromagnetic components 930, 970, 980. The conductive elements 910, 920, 960 and the second and third ferromagnetic components 970, 980 may be attached to the first ferromagnetic component 930 using one or more attachment members that are made of any suitable electrically isolating (e.g., dielectric) material. Further, it should be appreciated that in some examples, the combination of the first and second conductive elements 910, 920 and the ferromagnetic components 930, 970, 980 may be supported relative to one another, while the third conductive element 960 may be interchanged in and out of the treatment coil 900.

Figure 10A:
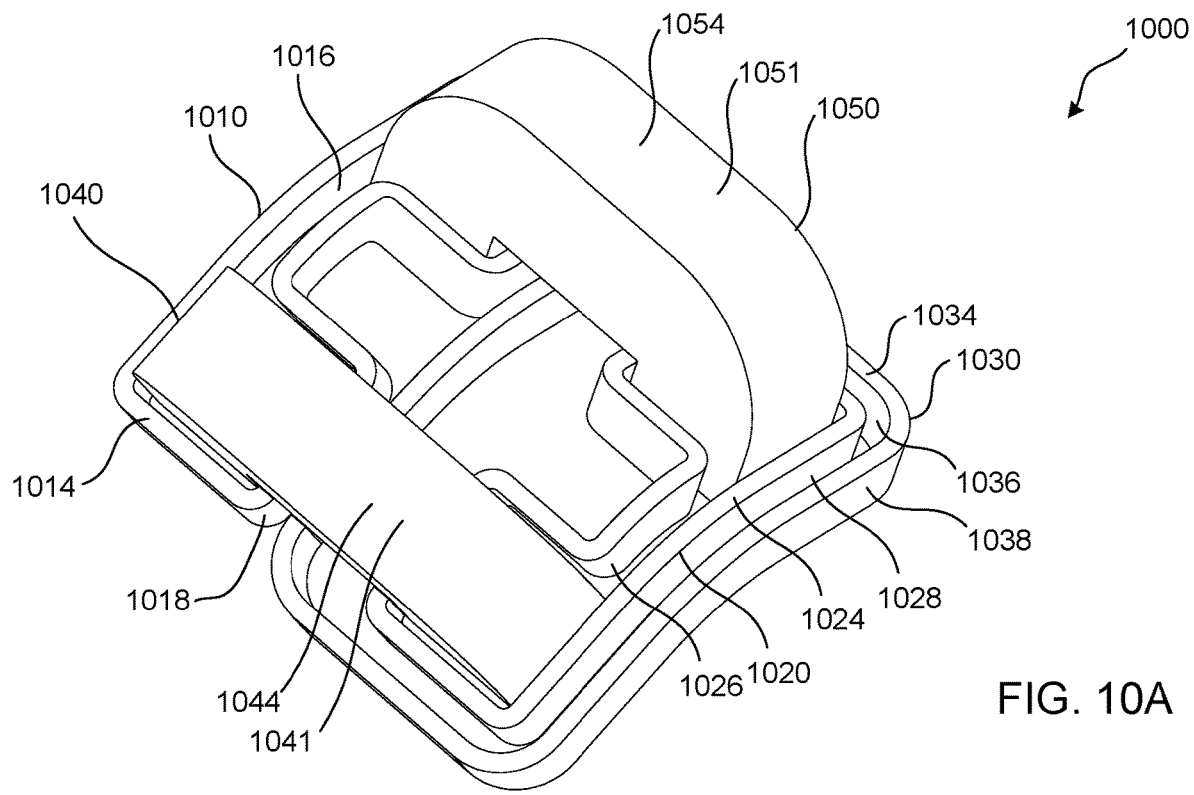
FIG. 10A is a diagram illustrating an overhead perspective of an example treatment coil that is configured to generate a changing magnetic field in a target anatomy of a subject.
Figure 10B:
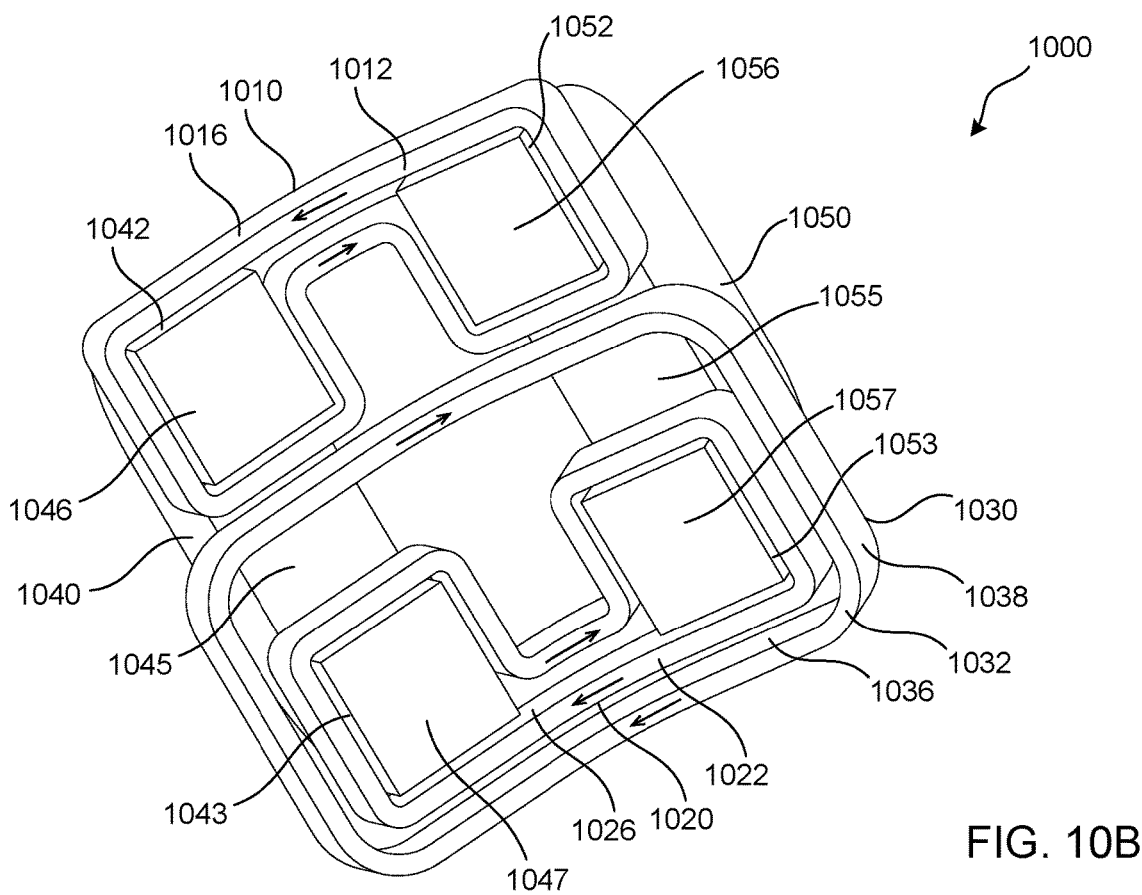
FIG. 10B is a diagram illustrating an underneath perspective of the example treatment coil of FIG. 10A that is configured to generate a changing magnetic field in a target anatomy of a subject.

FIGS. 10A-B depict an example treatment coil 1000 that is configured to generate a changing magnetic field in a target anatomy of a subject, such as a human subject (not shown). The target anatomy of the subject may be, for example, brain tissue of the subject. The treatment coil 1000 includes a first conductive element 1010, a second conductive element 1020, a third conductive element 1030, a first ferromagnetic component 1040, and a second ferromagnetic component 1050. The treatment coil 1000 may be disposed proximate to the head of the subject in preparation for or during TMS treatment, for example as shown in FIG. 1. The combination of the conductive elements 1010, 1020, 1030 and the ferromagnetic components 1040, 1050 collectively may be, for example, referred to as an electromagnet. It should be appreciated that the treatment coil 1000 may include more or fewer conductive elements and/or ferromagnetic components than illustrated. The conductive elements may be referred to as conductive windings.

The first, second, and third conductive elements 1010, 1020, 1030 may be made of any material that exhibits suitable electrical conductivity, such as copper, for example. The first and second conductive elements 1010, 1020 may include one or more bends. For example, the first conductive element 1010 may form a B-shaped coil, and similarly, the second conductive element 1020 may form a B-shaped coil. The first conductive element 1010 may define a bottom surface 1012, an upper surface 1014, an inner surface 1016, and an outer surface 1018. The second conductive element 1020 may define a bottom surface 1022, an upper surface 1024, an inner surface 1026, and an outer surface 1028.

The third conductive element 1030 may be semi-elliptical in shape (e.g., in the shape of a rounded-rectangle). Further, in some examples, the third conductive element 1030 may be another shape, such as circular in shape. The third conductive element 1030 may define a bottom surface 1032, an upper surface 1034, an inner surface 1036, and an outer surface 1038. The second conductive element 1020 may be disposed within an aperture of the third conductive element 1030. For example, the third conductive element 1030 may be configured to surround the second conductive element 1020. Further, the first, second, and/or third conductive elements may be curved. For example, the upper surfaces 1014, 1024, 1034 of the first, second, and/or third conductive elements may be concave, while the bottom surface 1012, 1022, 1032 of the first, second, and/or third conductive elements may be convex. However, it should be appreciated that in some examples, one or more of the upper and/or bottom surfaces 1014, 1012, 1024, 1022, 1034, 1032 of the first, second, and/or third conductive elements 1010, 1020, 1030 may be planar (e.g., flat).

The first, second, and/or third conductive elements 1010, 1020, 1030 may define the same number of turns (e.g., amp-turns), for example, a single turn, as illustrated. Although, it should be appreciated that in some examples, any one or more of the first, second, and/or third conductive elements 1010, 1020, 1030 may define multiple turns. Further, any combination of the first, second, and/or third conductive elements 1010, 1020, 1030 may define a different number of turns as another of the first, second, and/or third conductive elements 1010, 1020, 1030. Moreover, it should be appreciated that in some examples, the treatment coil 1000 may include additional conductive elements and/or conductive elements defining more than a single loop (e.g., amp-turn). For example, the first conductive element 1010 may include one or more additional and overlapping conductive elements (e.g., the first conductive element 1010 may defines more than a single loop), the second conductive element 1020 may include one or more additional and overlapping conductive elements (e.g., the second conductive element 1020 may define more than a single loop), and/or the third conductive element 1030 may include one or more additional and overlapping conductive elements (e.g., the third conductive element 1030 may define more than a single loop). The first, second, and/or third conductive elements 1010, 1020, 1030 may, individually, be formed of a single, monolithic piece of conductive material, or, one or more of the first, second, and/or third conductive elements 1010, 1020, 1030 may be formed by multiple strands of wire.

The first and second ferromagnetic components 1040, 1050 may be made of any material that exhibits suitable ferromagnetic properties, such as powdered ferromagnetic iron particles. The first ferromagnetic component 1040 may comprise a main body 1041 and a plurality of poles, such as a first pole 1042 and a second pole 1043 that extend from the main body 1041. Similarly, the second ferromagnetic component 1050 may comprise a main body 1051 and a plurality of poles, such as a first pole 1052 and a second pole 1053 that extend from the main body 1051. The first and second poles 1042, 1043 of the first ferromagnetic component 1040 may extend outward from the main body 1041 (e.g., from the bottom surface 1045 of the main body 1041). Similarly, the first and second pole 1052, 1053 of the second ferromagnetic component 1050 may extend outward from the main body 1051 (e.g., from the bottom surface 1055 of the main body 1051). Although illustrated as having two poles, in some examples, one or both of the first and second ferromagnetic components 1040, 1050 may include more or less than two poles. Further, in some examples, the first ferromagnetic component 1040 may include a different number of poles than the second ferromagnetic component 1050.

The main body 1041 of the first ferromagnetic component 1040 may define a top surface 1044 and a bottom surface 1045. The top surface 1044 and/or the bottom surface 1045 of the main body 1041 of the first ferromagnetic component 1040 may be planar (e.g., flat). However, it should be appreciated that in some examples, the main body 1041 may be curved, for example, as illustrated by the first ferromagnetic component 630 of the treatment coil 600. Similarly, the main body 1051 of the second ferromagnetic component 1050 may define a top surface 1054 and a bottom surface 1055. The top surface 1054 and/or the bottom surface 1055 of the main body 1051 of the second ferromagnetic component 1050 may be planar (e.g., flat). However, it should be appreciated that in some examples, the main body 1051 may be curved, for example, as illustrated by the first ferromagnetic component 630 of the treatment coil 600.

The first pole 1042 of the first ferromagnetic component 1040 may define a first pole face 1046, and the second pole 1043 may define a second pole face 1047. The first pole 1042 may be disposed within an aperture (e.g., a first loop of the "B" shape) defined by the first conductive element 1010, while the second pole 1043 may be disposed within an aperture (e.g., a first loop of the "B" shape) defined by the second conductive element 1020. Similarly, the first pole 1052 of the second ferromagnetic component 1050 may define a first pole face 1056, and the second pole 1053 may define a second pole face 1057. The first pole 1052 may be disposed within an aperture (e.g., a second loop of the "B" shape) defined by the first conductive element 1010, while the second pole 1053 may be disposed within an aperture (e.g., a second loop of the "B" shape) defined by the second conductive element 1020. Accordingly, the first and second pole faces 1042, 1043, 1052, 1053 of the first and second ferromagnetic components 1040, 1050 may be disposed within apertures of the first and second conductive elements 1010, 1020.

The first pole 1042 and the second pole 1043 of the first ferromagnetic component 1040 may have a cross-sectional shape that square-shaped (e.g., similar to a single loop of the "B" shape defined by the first and second conductive elements 1010, 1020). Similarly, the first pole 1052 and the second pole 1053 of the second ferromagnetic component 1050 may have a cross-sectional shape that square-shaped (e.g., similar to a single loop of the "B" shape defined by the first and second conductive elements 1010, 1020).

Further, in the illustrated example, the first pole face 1046 of the first ferromagnetic component 1040 may be substantially planar with the bottom surface 1016 of the first conductive element 1010, and the second pole face 1047 may be substantially planar with the bottom surface 1026 of the second conductive element 1020. Similarly, the first pole face 1056 of the second ferromagnetic component 1050 may be substantially planar with the bottom surface 1016 of the first conductive element 1010, and the second pole face 1057 may be substantially planar with the bottom surface 1026 of the second conductive element 1020. Although, it should be appreciated that in some examples, one or more of the first and/or second pole faces 1046, 1047, 1056, 1057 of the first and second ferromagnetic components 1040, 1050 may extend beyond the plane of the bottom surface 1016, 1026 of the respective first and second conductive elements 1010, 1020.

Although not illustrated, in some examples, one or both of the first and/or second ferromagnetic components 1040, 1050 may be configured to be adjustable (e.g., the curvature of the ferromagnetic component 1040, 1050 may be adjustable), for example, relative to the anatomy of the subject's head. For example, the first and/or second ferromagnetic component 1040, 1050 may include multiple pieces, such that one or more pieces of the ferromagnetic component 1040, 1050 may be configured so as to be adjustable relative to one or more other pieces of the ferromagnetic component 1040, 1050, and/or two or more of the pieces of the ferromagnetic component 1040, 1050 may be configured to be adjustable (e.g., pivotally adjustable) relative to each other (e.g., through the use of a hinge between the pieces of the ferromagnetic component 1040, 1050).

The treatment coil 1000 may be configured to be driven such that the treatment coil 1000 can be used to treat multiple (e.g., two) target areas of a subject. For example, during a treatment or diagnostic procedure, the treatment coil 1000 may be disposed so that the area where the first conductive element 1010 is proximate to the third conductive element 1030 under the bottom surface 1045 of the first ferromagnetic component 1040 may be placed above a first target area, and the area where the first conductive element 1010 is proximate to the third conductive element 1030 under the bottom surface 1055 of the second ferromagnetic component 1050 may be placed above a second target area of the subject. Thereafter, the treatment coil 1000 may be driven by a drive circuit of a treatment system and/or magnetic stimulation system. For example, the treatment coil 1000 may be configured such that, when driven, currents circulate through the first conductive element 1010 in a first same direction (e.g., a counter-clockwise direction when viewed from an underneath perspective, as illustrated in FIG. 10B), and currents circulate through the second and third conductive elements 1020, 1030 in a second, different direction (e.g., a clockwise direction when viewed from an underneath perspective, as illustrated in FIG. 10B).

As a result, the treatment coil 1000 may be configured to generate a magnetic field that induces two activation zones, one at each of the target locations. The activation zones may define a semi-elliptical shape (e.g., in a first target area proximate to the area where the first conductive element 1010 is proximate to the third conductive element 1030 under the bottom surface 1045 of the first ferromagnetic component 1040 may be placed above a first target area, and in a second target area proximate to the area where the first conductive element 1010 is proximate to the third conductive element 1030 under the bottom surface 1055 of the second ferromagnetic component 1050, respectively). For example, the treatment coil 1000 may be configured to generate magnetic fields that induce two activation zones, while also not inducing a stimulation zone in an area between the first and second ferromagnetic components 1040, 1050.

The two activation zones may have currents that flow in the same direction. For example, since the currents flowing through the first conductive element 1010 and the third conductive element 1030 are flowing in the same direction where the first and third conductive elements 1010, 1030 are closest to each other, the treatment coil 1000 may be configured to generate two activation zones that have currents that flow in the same direction. In some example procedures, the treatment coil 1000 may be disposed such that the first pole face 1046 of the first ferromagnetic component 1040 is disposed proximate to one eye of a patient, the first pole face 1056 is disposed proximate to the other eye of the patient, and the second pole faces 1047, 1057 of the first and second ferromagnetic components 1040, 1050 are located near the top of the patient's head.

It should be appreciated that, in some examples, one or both of the ferromagnetic components 1040, 1050 may be shifted so that the ferromagnetic components 1040, 1050 are not parallel with one another. In such instances, the treatment coil 1000 may be configured to generate two activation zones that are shifted from the illustrated embodiments of FIG. 10A-B. Alternatively or additionally, in some examples, one or both of the ferromagnetic components 1040, 1050 may be extended or shortened in length. Finally, in some examples, one or more of the conductive elements 1010, 1020, 1030 may be planar, for example, so that the treatment coil 1000 may be configured to accommodate different head shapes.

The treatment coil 1000 may be configured such that when the first, second, and third conductive elements 1010, 1020, 1030 are driven the resulting activation zone encompasses two independent areas within a brain of a subject. The areas within the brain of the subject may be correlated with different functional regions of the brain. For example, the treatment coil 1000 may be used to stimulate two different areas within the brain of the subject, such as a first area located below and proximate to the second pole face 1047 of the first ferromagnetic component and a second area located below and proximate to the second pole face 1057 of the second ferromagnetic component. The currents in the two areas of the brain may move in the same or different directions (e.g., clockwise and/or counter-clockwise).

The activation zone induced by the magnetic field generated by the treatment coil 1000 may be a stimulation zone or sub-stimulation zone. The stimulation zone may be at a level where the induced current caused by the pulsing magnetic field generated by the treatment coil 1000 is above a depolarization threshold of neurons of the brain, while a sub-stimulation zone may at a level where the induced current is below the depolarization threshold of neurons of the brain. Further, although described with reference to two activation zones and two treatment areas, the treatment coil 1000 may be used to generate a magnetic field that induces more or less activation zones for more or less treatment areas of the patient (e.g., depending on the specific treatment or diagnostic procedure).

In some examples, the treatment coil 1000 may include a housing (not shown) that houses the first, second, and third conductive winding 1010, 1020, 1030 and the first and second ferromagnetic components 1040, 1050. Also, in some examples, the first conductive elements 1010 may be replaced with two, semi-elliptical conductive elements, where the first pole of the first ferromagnetic component 1040 is configured to be disposed within an aperture of one conductive element, and where the first pole face of the second ferromagnetic component 1050 is configured to be disposed within an aperture of the other conducive element. Similarly, the second conductive element 1020 may also be replaced with two, semi-elliptical conductive elements.

The treatment coil 1000 may be configured such that the conductive elements 1010, 1020, 1030 and the ferromagnetic components 1040, 1050 are supported relative to each other. For example, the treatment coil 1000 may be configured such that the ferromagnetic components 1040, 1050 supports the conductive elements 1010, 1020, 1030. One or both of the conductive elements 1010, 1020, 1030 and the ferromagnetic components 1040, 1050 may include one or more complementary attachment members (not shown) that are configured to enable attachment (e.g., releasable attachment) of the conductive elements 1010, 1020, 1030 to the ferromagnetic components 1040, 1050. The one or more attachment members may be configured such that the conductive elements 1010, 1020, 1030 and the ferromagnetic components 1040, 1050 are fixedly supported relative to each other. The one or more attachment members may be configured such that the conductive elements 1010, 1020, 1030 and the ferromagnetic components 1040, 1050 are movable (e.g., repositionable) relative to each other.

When the conductive elements 1010, 1020, 1030 are supported by (e.g., attached to) the ferromagnetic components 1040, 1050, the conductive elements 1010, 1020, 1030 may be electrically isolated from the ferromagnetic components 1040, 1050, for example using a dielectric. The dielectric may be air, and the conductive elements 1010, 1020, 1030 may be spaced from (e.g., not in direct contact with) the ferromagnetic components 1040, 1050 when the conductive elements 1010, 1020, 1030 are attached to the ferromagnetic components 1040, 1050. The conductive elements 1010, 1020, 1030 may be attached to the ferromagnetic components 1040, 1050 using one or more attachment members that are made of any suitable electrically isolating (e.g., dielectric) material.

FIGS. 11A-H depict an example treatment coil 1100 that is configured to generate a changing magnetic field in a target anatomy of a subject, such as a human subject (not shown). The target anatomy of the subject may be, for example, brain tissue of the subject. The treatment coil 1100 includes a first conductive element 1110, a second conductive element 1120, a third conductive element 1130, a first ferromagnetic component 1140, a second ferromagnetic component 1150, a third ferromagnetic component 1160, a fourth ferromagnetic component 1170, a fifth ferromagnetic component 1175, a sixth ferromagnetic component 1180, a seventh ferromagnetic component 1185, an eighth ferromagnetic component 1190*a*, and a ninth ferromagnetic component 1190*b*. The treatment coil 1100 may be disposed proximate to the head of the subject in preparation for or during TMS treatment, for example as shown in FIG. 1. The combination of the conductive elements and the ferromagnetic components collectively may be, for example, referred to as an electromagnet. The conductive elements may be referred to as conductive windings.

In FIGS. 11C-H, the ferromagnetic components (e.g., the first, second, third, ninth and tenth ferromagnetic components 1140, 1150, 1160, 1190*a*, 1190*b*) may be separated from the treatment coil 1100 for purposes of illustration and explanation. However, it should be appreciated that, when the treatment coil 1100 is put into use, the gaps between the ferromagnetic components (e.g., the first, second, third, ninth and tenth ferromagnetic components 1140, 1150, 1160, 1190*a*, 1190*b*) themselves, and/or the gaps between the ferromagnetic components (e.g., the first, second, third, ninth and tenth ferromagnetic components 1140, 1150, 1160, 1190*a*, 1190*b*) and the conductive elements may be reduced or eliminated. Further, as described in more detail herein, the treatment coil 1100 may include more or fewer conductive elements and/or ferromagnetic components than illustrated. For example, any combination of the ferromagnetic components may be eliminated from the treatment coil 1100 based on, for example, the treatment or diagnostic procedure (e.g., the target anatomy), the size and/or shape of the patient (e.g., the patient's head), etc.

Figure 11A:
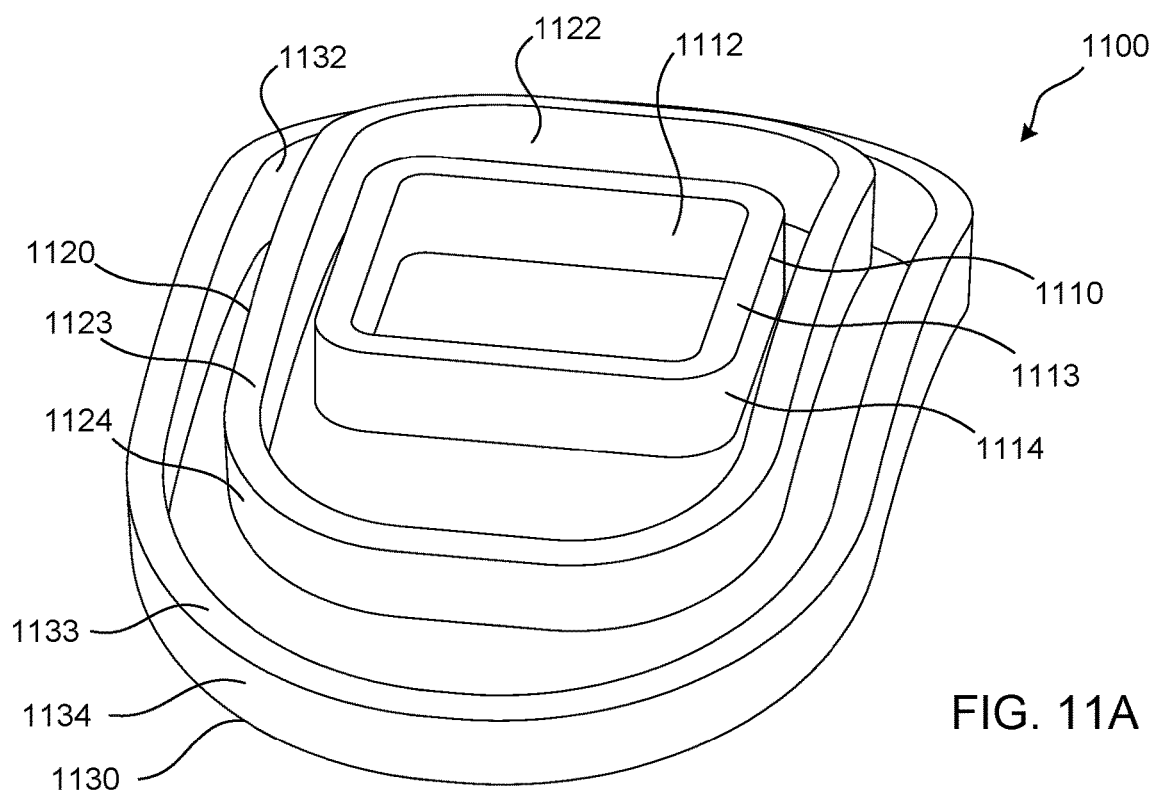
FIG. 11A is a diagram illustrating an overhead perspective of a portion of an example treatment coil that is configured to generate a changing magnetic field in a target anatomy of a subject.
Figure 11B:
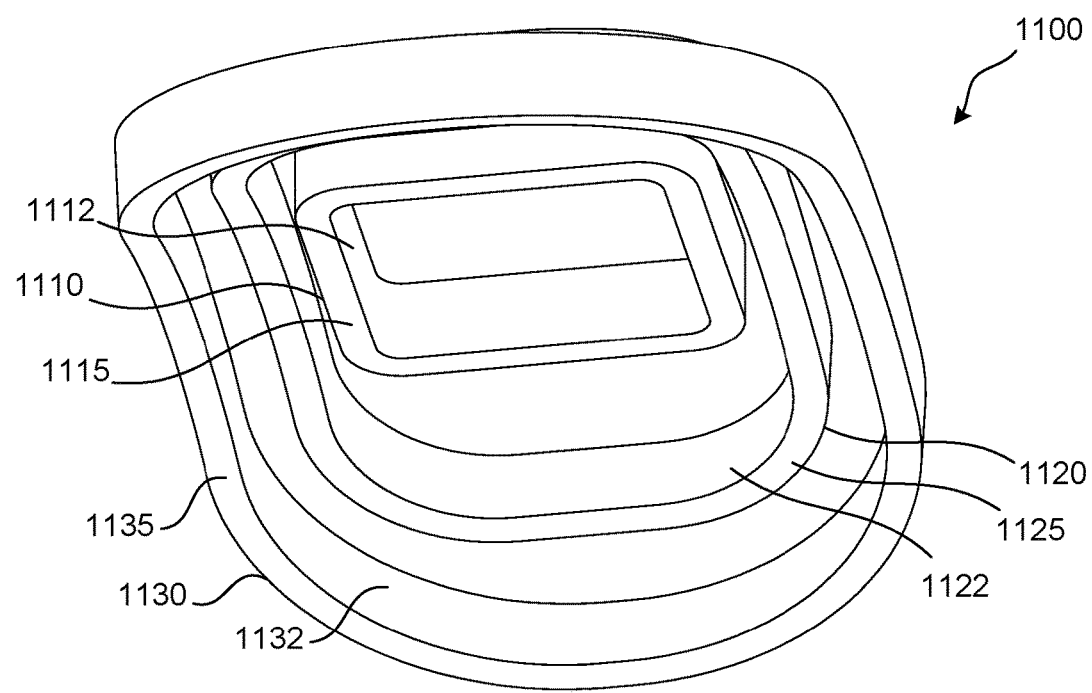
FIG. 11B is a diagram illustrating an underneath perspective of the example treatment coil of FIG. 11A that is configured to generate a changing magnetic field in a target anatomy of a subject.

FIGS. 11A-B illustrate the first conductive element 1110, the second conductive element 1120, and the third conductive element 1130. The first, second, and third conductive elements 1110, 1120, 1130 may be made of any material that exhibits suitable electrical conductivity, such as copper, for example. The first conductive element 1110 may be semi-elliptical in shape (e.g., in the shape of a rounded-square). However, it should be appreciated that in some examples, the first conductive element 1110 may be another shape, such as circular in shape. The first conductive element 1110 may define an inner surface 1112, an outer surface 1114, an upper surface 1113, and a bottom surface 1115.

The second and third conductive elements 1120, 1130 may be semi-elliptical in shape (e.g., shaped like a rounded-rectangle). Further, it should be appreciated that in some examples, the second and third conductive elements 1120, 1130 may be another shape, such as circular in shape. The second conductive element 1120 may define an inner surface 1122, an outer surface 1124, an upper surface 1123, and a bottom surface 1125. Similarly, the third conductive element 1130 may define an inner surface 1132, an outer surface 1134, an upper surface 1133, and a bottom surface 1135. The second and/or third conductive elements 1120, 1130 may be bent downwards, for example, as illustrated. For example, the bottom surface 1125 of the second conductive element 1120 may be concave, while the upper surface 1123 may be convex. Similarly, the bottom surface 1135 of the third conductive element 1130 may be concave, while the upper surface 1133 may be convex. Although, it should be appreciated that in some examples, one or more of the upper and/or bottom surfaces 1123/1125, 1133/1135 of the second and/or the third conductive elements 1120, 1130 may be planar (e.g., such that the second and/or the third conductive element 1120, 1130 is not bent).

The third conductive element 1130 may define a larger circumference than the second conductive element 1120, and the second conductive element 1120 may define a larger circumference than the first conductive element 1110. The first conductive element 1110 may, at least partially, reside within an aperture of the second conductive element 1120, and the second conductive element 1120 may, at least partially, reside within an aperture of the third conductive element 1130. That is, the third conductive element 1130 may surround (e.g., entirely or substantially surround) one or more of the first and/or second conductive elements 1110, 1120, and the second conductive element 1120 may surround (e.g., entirely or substantially surround) the first conductive element 1110.

The first, second, and/or third conductive element 1110, 1120, 1130 may be formed of a single, monolithic piece of conductive material, or, one or more of the first, second, and/or third conductive elements 1110, 1120, 1130 may be formed by multiple strands of wire. Any combination of the first, second, and/or third conductive element 1110, 1120, 1130 may define the same number of turns (e.g., amp-turns), for example, a single turn, as illustrated. Although, it should be appreciated that in some examples, the second conductive element 1120 and/or the third conductive element 1130 may define multiple turns. For instance, in some examples, the first conductive element 1100 may define a first number of turns, while one or both of the second and/or third conducive elements 1120, 1130 may define a different, second number of turns.

Figure 11C:
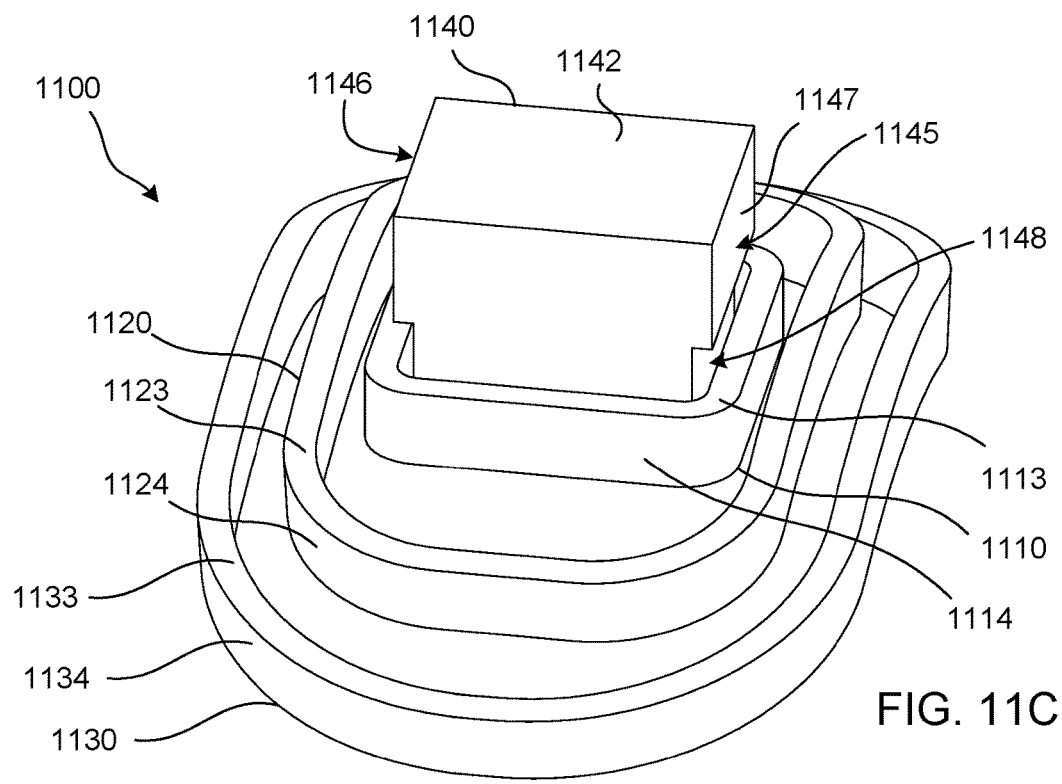
FIG. 11C is a diagram illustrating an overhead perspective of the example treatment coil of FIG. 11A with the inclusion of a ferromagnetic component.
Figure 11D:
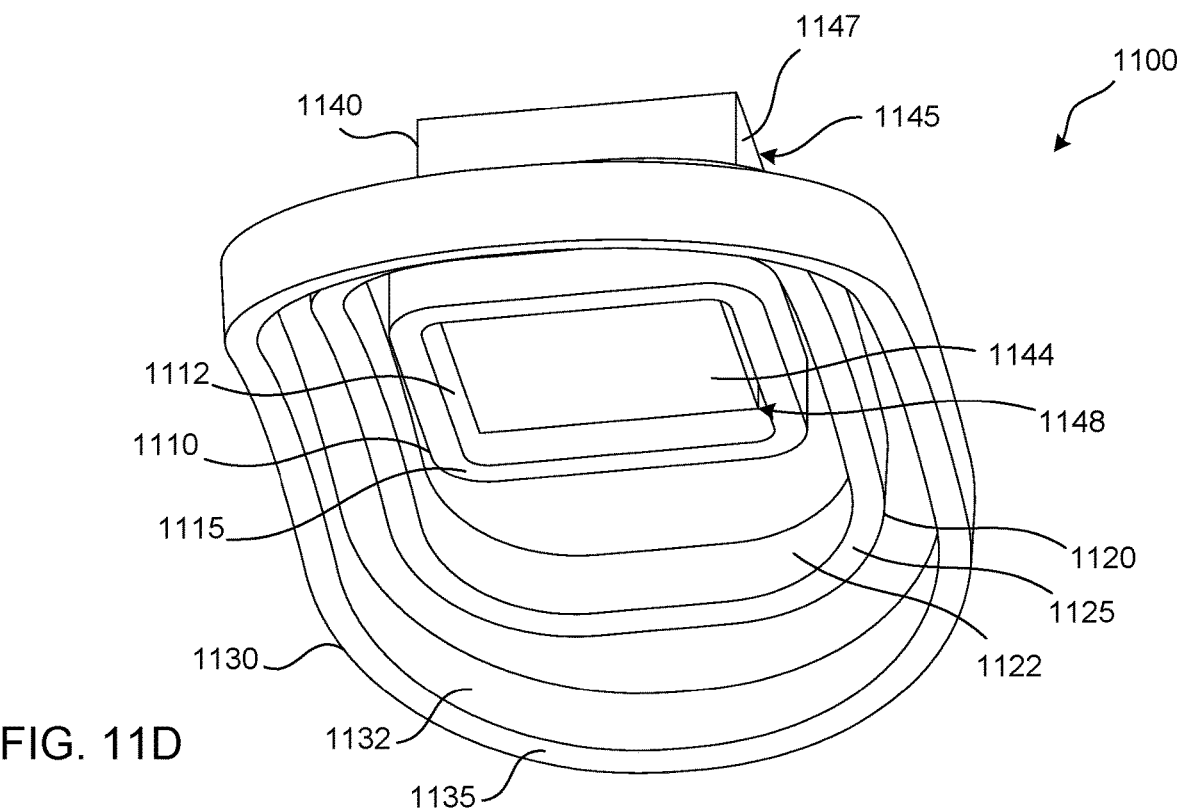
FIG. 11D is a diagram illustrating an underneath perspective of the example treatment coil of FIG. 11C.

FIGS. 11C-D illustrate the first conductive element 1110, the second conductive element 1120, the third conductive element 1130, and the first ferromagnetic component 1140. The first ferromagnetic component 1140 may be made of any material that exhibits suitable ferromagnetic properties, such as powdered ferromagnetic iron particles. The first ferromagnetic component 1140 may define a top surface 1142, a bottom surface 1144, and eight outer surfaces (not labeled). Each of the top surface 1142, the bottom surface 1144, and the outer surfaces may be planar. Although, it should be appreciated that in some examples, one or more of the top surface 1142, the bottom surface 1144, and/or any combination of the outer surfaces may be curved or otherwise shaped. The bottom surface 1144 may be referred to as a pole face of the first ferromagnetic component 1140.

The first ferromagnetic component 1140 may be sized and shaped so that the first ferromagnetic component 1140 may reside at least partially within an aperture of the first conductive element 1110. For example, the first ferromagnetic component 1140 may include a wider, top portion 1145, and a narrower, bottom portion 1148. For example, the first ferromagnetic component 1140 may be shaped such that a cross-sectional shape of the first ferromagnetic component 1140 is "T" shaped. However, it should be appreciated that in some examples, the first ferromagnetic component 1140 may be other shapes, and for example, may define a uniform width throughout.

The top portion 1145 may include opposite sides 1146, 1147. The top portion 1145 may reside above the top surface 1113 of the first conductive element 1110, and outside of the aperture of the first conductive element 1110, while the bottom portion 1148 may reside within (e.g., partially or entirely within) the aperture of the first conductive element 1110. Further, the bottom surface 1144 of the first ferromagnetic component 1140 may be planar or non-planar (e.g., as shown) with the bottom surface 1115 of the first conductive element 1110. Finally, it should be appreciated that the first ferromagnetic component 1140 may reside within (e.g., partially or entirely within) the apertures of one or more of the second or third conductive elements 1120, 1130 (e.g., since the first conductive element 1110 may reside at least partially within the apertures of one or more of the second or third conductive elements 1120, 1130).

Figure 11E:
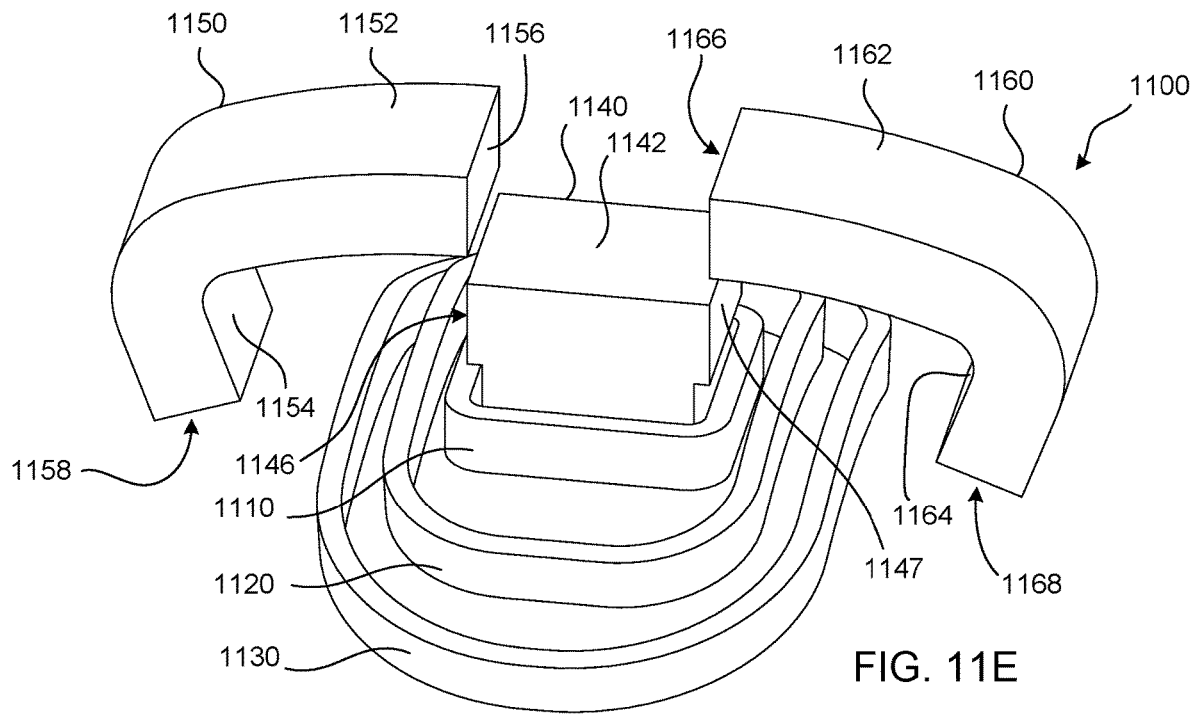
FIG. 11E is a diagram illustrating an overhead perspective of the example treatment coil of FIG. 11A with the inclusion of multiple ferromagnetic components.
Figure 11F:
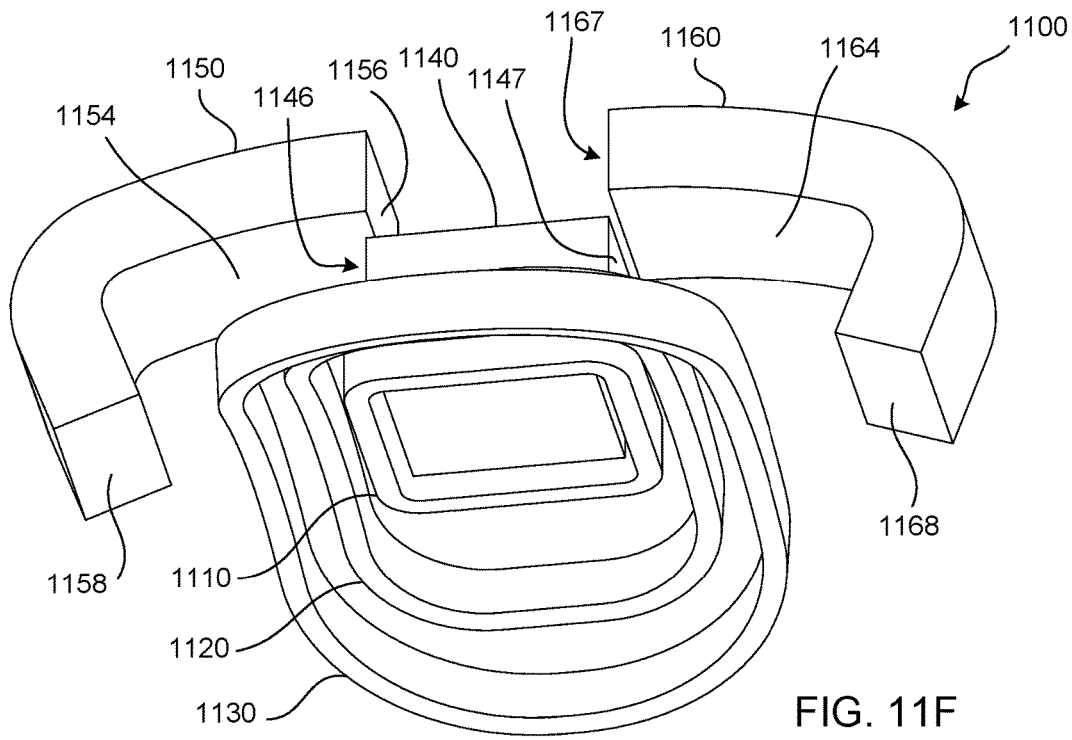
FIG. 11F is a diagram illustrating an underneath perspective of the example treatment coil of FIG. 11E.

FIGS. 11E-F illustrate the first conductive element 1110, the second conductive element 1120, the third conductive element 1130, the first ferromagnetic component 1140, the second ferromagnetic component 1150, and the third ferromagnetic component 1160. The second and third ferromagnetic components 1150, 1160 may be made of any material that exhibits suitable ferromagnetic properties, such as powdered ferromagnetic iron particles. The second ferromagnetic component 1150 may define a top surface 1152, a bottom surface 1154, a first pole face 1156, and a second pole face 1158. The second ferromagnetic component 1150 may be curved, for example, as illustrated. For example, the top surface 1152 may define a convex surface, while the bottom surface 1154 may define a concave surface. Accordingly, the top surface 152 may be non-planar, and the bottom surface 1154 may be non-planar. Further, it should be appreciated that in some examples, the curvature of the top and/or bottom surface 1152, 1154 of the second ferromagnetic component 1150 may define a greater or lesser curvature than illustrated. Moreover, it should be appreciated that in some examples, the top surface 1152 and/or the bottom surface 1154 of the second ferromagnetic component 1150 may be planar (e.g., flat).

The third ferromagnetic component 1160 may define a top surface 1162, a bottom surface 1164, a first pole face 1166, and a second pole face 1168. The third ferromagnetic component 1160 may be curved, for example, as illustrated. For example, the top surface 1162 may define a convex surface, while the bottom surface 1164 may define a concave surface. Accordingly, the top surface 162 may be non-planar, and the bottom surface 1164 may be non-planar. Further, it should be appreciated that in some examples, the curvature of the top and/or bottom surface 11652, 1164 of the third ferromagnetic component 1160 may define a greater or lesser curvature than illustrated. Moreover, it should be appreciated that in some examples, the top surface 1162 and/or the bottom surface 1164 of the third ferromagnetic component 1160 may be planar (e.g., flat). Further, although the first and second pole faces 1156, 1158, 1166, 1168 of the second and third ferromagnetic components 1150, 1160 are illustrated as planar (e.g., flat), any combination of the first and second pole faces 1156, 1158, 1166, 1168 of the second and third ferromagnetic components 1150, 1160 may be curved.

Although illustrated as being raised (e.g., from the perspective of FIG. 11E), the second and third ferromagnetic components 1150, 1160 may be lowered to align with the first ferromagnetic component 1140 (e.g., when the treatment coil 1100 is in use). For example, the first pole face 1156 of the second ferromagnetic component 1150 may be disposed proximate to the side 1146 of the first ferromagnetic component 1140, and the first pole face 1166 of the third ferromagnetic component 1160 may be disposed proximate to the side 1147 of the first ferromagnetic component 1140. As such, the top surfaces 1152, 1162 of the second and third ferromagnetic components 1150, 1160 may align with the top surface 1142 of the first ferromagnetic component, the bottom surfaces 1154, 1164 may align with the interface between the top and bottom portions 1145, 1148 of the first ferromagnetic component 1140, and the outer surfaces of the first, second, and third ferromagnetic components 1140, 1150, 1160 may align. Further, in some examples, when lowered to align with the first ferromagnetic component 1140, the second pole faces 1158, 1168 of the second and third ferromagnetic components 1150, 1160 may be planar with the bottom surface 1135 of the third conductive element 1130.

The first, second, and third ferromagnetic components 1140, 1150, 1160 may be linearly aligned (e.g., as illustrated). For example, outer surfaces of the first, second, and third ferromagnetic components 1140, 1150, 1160 may reside within the same plane. However, it should be appreciated that in some examples, one or more of the first, second, and/or third ferromagnetic components 1140, 1150, 1160 may be aligned in a non-linear manner.

The second and third ferromagnetic components 1150, 1160 may be substantially the same size and shape. However, in some examples, the second and third ferromagnetic components 1150, 1160 may have a different size and/or shape than illustrated. Further, in some example, the size or shape of second ferromagnetic component 1150 may be different from the size or shape of the third ferromagnetic component 1160 (e.g., to shift the size and/or shape of the magnetic field generated by the treatment coil 1100).

Figure 11G:
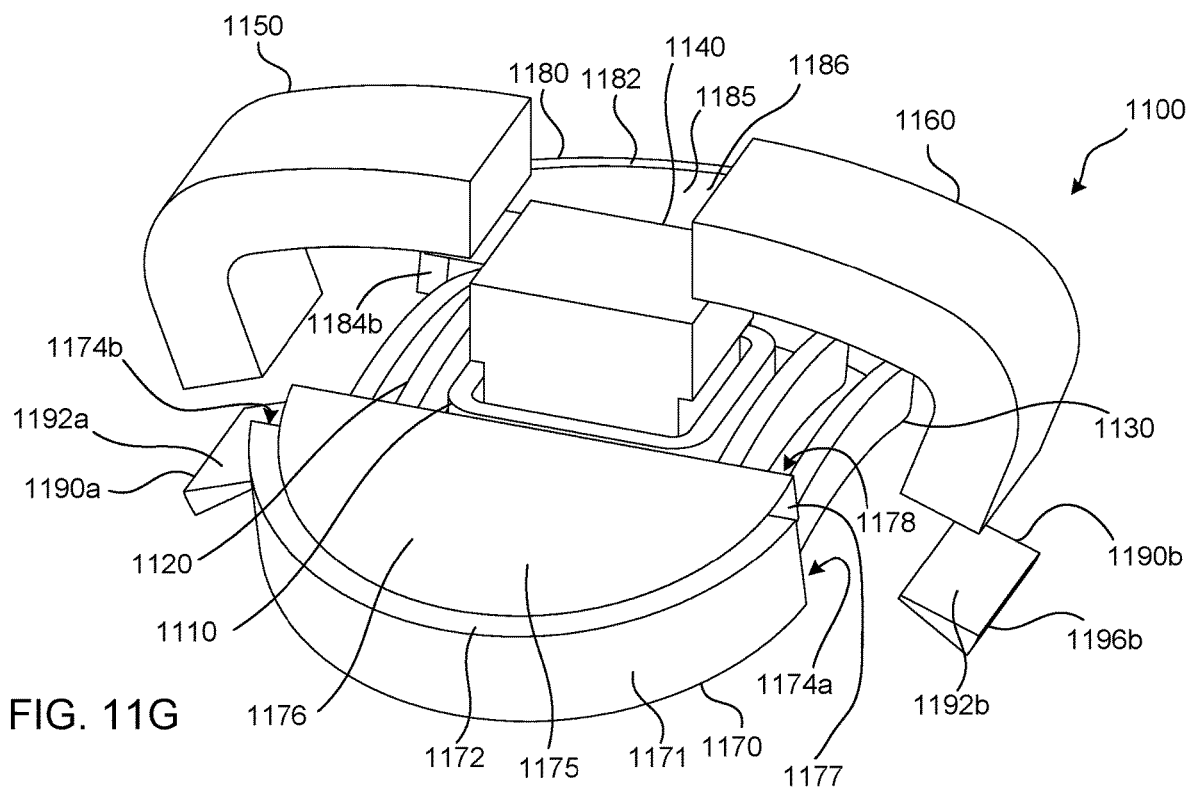
FIG. 11G is a diagram illustrating an overhead perspective of the example treatment coil of FIG. 11A with the inclusion of multiple ferromagnetic components.
Figure 11H:
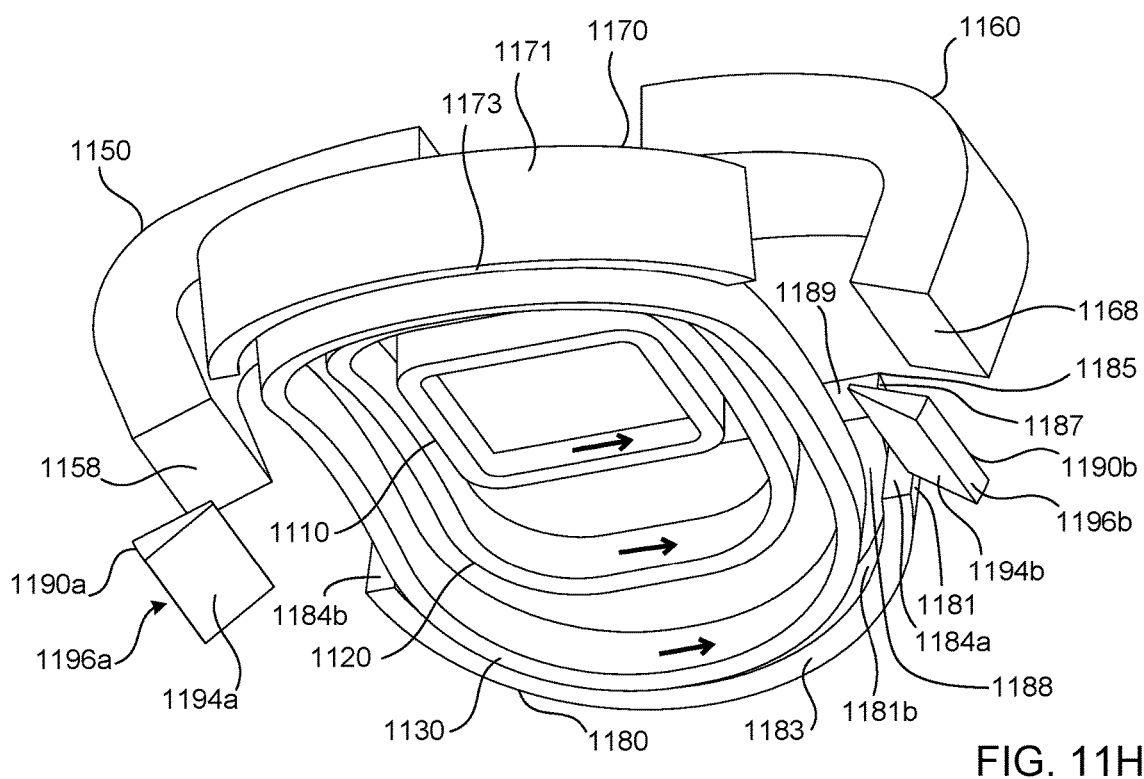
FIG. 11H is a diagram illustrating an underneath perspective of the example treatment coil of FIG. 11G.

FIGS. 11G-H illustrate the first conductive element 1110, the second conductive element 1120, the third conductive element 1130, the first ferromagnetic component 1140, the second ferromagnetic component 1150, the third ferromagnetic component 1160, a fourth ferromagnetic component 1170, a fifth ferromagnetic component 1175, a sixth ferromagnetic component 1180, a seventh ferromagnetic component 1185, an eighth ferromagnetic component 1190a, and a ninth ferromagnetic component 1190b. The fourth, fifth, sixth, seventh, eighth, and ninth ferromagnetic components 1170, 1175, 1180, 1185, 1190a, 1190b may be made of any material that exhibits suitable ferromagnetic properties, such as powdered ferromagnetic iron particles.

The fourth ferromagnetic component 1170 may define an outer surface 1171, an inner surface (not shown), an upper surface 1172, a bottom surface 1173, and two end surfaces 1174a, 1174b. Similarly, the sixth ferromagnetic component 1180 may define an outer surface 1181, an inner surface 1181a, an upper surface 1182, a bottom surface 1183, and two end surfaces 1184a, 1184b. Each of the upper surfaces 1172, 1182, the bottom surfaces 1173, 1183, and the end surfaces 1174a/b, 1184a/b of the fourth and sixth ferromagnetic components 1170, 1180 may be planar. Although, it should be appreciated that in some examples, one or more of the upper surfaces 1172, 1182, the bottom surfaces 1173, 1183, and the end surfaces 1174a/b, 1184a/b of the fourth and sixth ferromagnetic components 1170, 1180 may be curved or otherwise shaped.

The fourth and sixth ferromagnetic components 1170, 1180 may be curved. For example, the inner surfaces of the fourth and sixth ferromagnetic components 1170, 1180 may be concave, while the outer surfaces 1171, 1181 of the fourth and sixth ferromagnetic components 1170, 1180 may be convex. For example, the curvature of the inner and outer surfaces of the fourth and sixth ferromagnetic components 1170, 1180 may be substantially similar to the curvature of the outer surfaces of the fifth and seventh ferromagnetic elements 1175, 1185, respectively, and/or similar to the curvature of the third conductive elements 1130. However, the curvature of the inner and outer surfaces of the fourth and sixth ferromagnetic components 1170, 1180 is not limited to that illustrated in FIGS. 13G-H.

The fourth and sixth ferromagnetic components 1170, 1180 may be substantially the same size and shape. However, in some examples, the fourth and sixth ferromagnetic components 1170, 1180 may have a different size and/or shape than illustrated. Further, in some example, the size or shape of fourth ferromagnetic component 1170 may be different from the size or shape of the sixth ferromagnetic component 1180 (e.g., to shift the size and/or shape of the magnetic field generated by the treatment coil 1100).

The fifth ferromagnetic component 1175 may define an upper surface 1176, an outer surface 1177, a bottom surface (not shown), and an inner surface 1178. Similarly, the seventh ferromagnetic component 1185 may define an upper surface 1186, an outer surface 1187, a bottom surface 1188, and an inner surface 1189. The fifth and seventh ferromagnetic components 1175, 1185 may be curved (e.g., partially curved). For example, the outer surfaces 1177, 1187 of the fifth and seventh ferromagnetic components 1175, 1185 may be convex. For example, the fifth and seventh ferromagnetic components 1175, 1185 may have a semi-circular cross-sectional shape.

The inner surfaces of the fifth and seventh ferromagnetic components 1175, 1185 may be planar (e.g., flat). For example, the inner surfaces of the fifth and seventh ferromagnetic components 1175, 1185 may be parallel with outer surfaces of the first ferromagnetic component 1140. The combination of the fourth and fifth ferromagnetic components 1170, 1175 may cover a portion (e.g., a top and outer portion) of one or more of the first, second, and/or third conductive elements 1110, 1120, 1130. Similarly, the combination of the sixth and seventh ferromagnetic components

1180, 1185 may cover a portion (e.g., a top and outer portion) of one or more of the first, second, and/or third conductive elements 1110, 1120, 1130.

Further, in some examples, when the second and third ferromagnetic components 1150, 1160 are aligned with the first ferromagnetic component 1140, there may be a gap between the inner surfaces of the fifth and/or seventh ferromagnetic component 1175, 1185 and an outer surface of the first, second, and third ferromagnetic components 1140, 1150, 1160. However, it should be appreciated that in some examples, there may not be a gap between the inner surfaces of the fifth and/or seventh ferromagnetic component 1175, 1185 and an outer surface of the first, second, and third ferromagnetic components 1140, 1150, 1160 when the second and third ferromagnetic components 1150, 1160 are aligned with the first ferromagnetic component 1140.

The eighth ferromagnetic component 1190a may define an outer surface 1196a, a top surface 1192a, a left and right surface, and a bottom surface that defines a pole 1194a. Similarly, the ninth ferromagnetic component 1190b may define an outer surface 1196b, a top surface 1192b, a left and right surface, and a bottom surface that defines a pole 1194b. The upper surfaces of the eighth and ninth ferromagnetic components 1190a, 1190b may be of a similar size and shape (e.g., an identical size and shape) as the second pole faces 1158, 1168, respectively. Further, the upper surfaces of the eighth and ninth ferromagnetic components 1190a, 1190b may be parallel with the second pole faces 1158, 1168, respectively. When the treatment coil 1100 is in use, the upper surfaces of the eighth and ninth ferromagnetic components 1190a, 1190b may be placed proximate to (e.g., and potentially secured to) the second pole faces 1158, 1168, respectively.

The poles 1158, 1168 of the eighth and ninth ferromagnetic components 1190a, 1190b may be angled. For example, the pole face 1158 of the eighth ferromagnetic component 1090a may form an acute angle with the upper surface 1192a of the eighth ferromagnetic component 1090a. Similarly, the pole face 1168 of the ninth ferromagnetic component 1090b may form an acute angle with the upper surface 1192b of the ninth ferromagnetic component 1090b. In some examples, the eighth and ninth ferromagnetic components 1190a, 1190b may be omitted from the treatment coil 1100, or may be substituted for other ferromagnetic components of any desirable size and shape, such as the fourth and fifth ferromagnetic components 745a, 745b illustrated in FIG. 7C, the sixth and seventh ferromagnetic component 745c, 745d illustrated in FIG. 7D, and/or the like.

In FIGS. 11C-H, the ferromagnetic components (e.g., the first, second, third, ninth and tenth ferromagnetic components 1140, 1150, 1160, 1190a, 1190b) may be separated from the treatment coil 1100 for purposes of illustration and explanation. However, it should be appreciated that, when the treatment coil 1100 is put into use, the gaps between the ferromagnetic components (e.g., the first, second, third, ninth and tenth ferromagnetic components 1140, 1150, 1160, 1190a, 1190b) themselves, and/or the gaps between the ferromagnetic components (e.g., the first, second, third, ninth and tenth ferromagnetic components 1140, 1150, 1160, 1190a, 1190b) and the conductive elements may be reduced or eliminated.

The treatment coil 1100 may be disposed so that the area where the first, second, and third conductive elements 1010, 1020, 1030 are proximate to the bottom surface 1154 of the second ferromagnetic component 1150 may be placed above a first target area, and the area where the first, second, and third conductive elements 1010, 1020, 1030 are proximate to the bottom surface 1164 of the third ferromagnetic component 1160 may be placed above a second target area of the subject (e.g., or, if the ninth ferromagnetic component 1190b is included, then the pole 1194b may be placed above the second target area). Thereafter, the treatment coil 1100 may be driven by a drive circuit of a treatment system and/or magnetic stimulation system. For example, the treatment coil 1100 may be configured such that, when driven, currents circulate through the first, second, and third conductive elements 1110, 1120, 1130 in the same direction (e.g., a counter-clockwise direction when viewed from an underneath perspective, as illustrated in FIG. 11H), or vice versa.

As a result, the treatment coil 1100 may be configured to generate a magnetic field that induces two activation zones, one at each of the target locations, where each of the activation zones have an elliptical shape (e.g., substantially below the area where the first, second, and third conductive elements 1010, 1020, 1030 are proximate to the bottom surface 1154 of the second ferromagnetic component 1150, and substantially below the area where the first, second, and third conductive elements 1010, 1020, 1030 are proximate to the bottom surface 1164 of the third ferromagnetic component 1160, respectively). For example, the treatment coil 1100 may be configured to generate magnetic fields that induce two activation zones, while also not inducing a stimulation zone in an area under the bottom surface 1144 of the first ferromagnetic component 1140.

Further, the inclusion of the fourth, fifth, sixth, and seventh ferromagnetic components 1170, 1175, 1180, 1185 may act to spread the return currents caused by the magnetic field generated by the treatment coil 1000 (e.g., as compared to when the fourth, fifth, sixth, and seventh ferromagnetic components 1170, 1175, 1180, 1185 are not included) to, for example, further pronounce the two activation zones (e.g., under the first and second target areas) created by the magnetic field and prevent the two activation zones from merging into a single activation zone (e.g., a single oval or circular shaped activation zone that includes the area under the bottom surface 1144 of the first ferromagnetic component 1140). That is, the inclusion of the fourth, fifth, sixth, and seventh ferromagnetic components 1170, 1175, 1180, 1185 distorts the magnetic field generated by the treatment coil 1100 by spreading the return currents to areas that are substantially under and proximate to the fourth and sixth ferromagnetic components 1170, 1180. For example, the inclusion of the fourth, fifth, sixth, and seventh ferromagnetic components 1170, 1175, 1180, 1185 may pull the return currents further away from the bottom surface 1144 of the first ferromagnetic component 1040 to, for example, enhance the two activation zones and prevent a single activation zone (e.g., one big ring) from resulting. That is, without the inclusion of the ferromagnetic components 1170, 1175, 1180, 1185, the return currents may take a shorter path, for example, the path defined by the first conductive element 1010. As such, the ferromagnetic components 1170, 1175, 1180, 1185 may assist in ensuring that the two activation zones do not combine (e.g., merge) into one, large activation zone (e.g., a single activation zone that includes the area under the bottom surface 1144 of the first ferromagnetic component 1040).

It should be appreciated that the treatment coil 1100 may include more or fewer conductive elements and/or ferromagnetic components than illustrated. For example, any combination of the ferromagnetic components may be eliminated from the treatment coil 1100 based on, for example, the treatment or diagnostic procedure (e.g., the target anatomy), the size and/or shape of the patient (e.g., the patient's head), etc. In some examples, the eighth and ninth ferromagnetic components 1190*a*, 1190*b* may be omitted (e.g., due to the patient's head size and/or shape). Further, in some examples, any combination of the fourth, fifth, sixth, and/or seventh ferromagnetic components 1170, 1175, 1180, 1185 may be omitted based on, for example, the treatment or diagnostic procedure (e.g., the particular target areas). For example, omission of any combination of the fourth, fifth, sixth, and/or seventh ferromagnetic components 1170, 1175, 1180, 1185 may result in a change to the separation of the stimulation zones, a change to the relative direction of the electric field in the two stimulation zones, a change to the shape of one or more of the stimulation zones, a change or move to the return currents, a reduction in the stimulation of a cranial nerve, and/or the like.

The treatment coil 1100 may be configured such that when the conductive elements 1110, 1120, 1130 are driven the resulting activation zone encompasses two independent areas within a brain of a subject. The areas within the brain of the subject may be correlated with different functional regions of the brain. For example, the treatment coil 1100 may be used to stimulate two different areas within the brain of the subject, such as a first area located below and proximate to the second pole face 1158 of the second ferromagnetic component 1150, and a second area located below and proximate to the second pole face 1168 of the third ferromagnetic component 1160. The currents in the two areas of the brain may move in the same or different directions (e.g., clockwise and/or counter-clockwise).

The activation zone induced by the magnetic field generated by the treatment coil 1100 may be a stimulation zone or sub-stimulation zone. The stimulation zone may be at a level where the induced current caused by the pulsing magnetic field generated by the treatment coil 1100 is above a depolarization threshold of neurons of the brain, while a sub-stimulation zone may be at a level where the induced current is below the depolarization threshold of neurons of the brain. Further, although described with reference to two activation zones and two treatment areas, the treatment coil 1100 may be used to generate a magnetic field that induces more or less activation zones for more or less treatment areas of the patient (e.g., depending on the specific treatment or diagnostic procedure).

In some examples, the treatment coil 1100 may include a housing (not shown) that houses the any combination of the conductive elements 1110, 1120, 1130 and the ferromagnetic components 1140, 1150, 1160, 1170, 1175, 1180, 1185, 1190*a*, 1190*b*. The treatment coil 1100 may be configured such that the conductive elements 1110, 1120, 1130 and the ferromagnetic components 1140, 1150, 1160, 1170, 1175, 1180, 1185, 1190*a*, 1190*b* are supported relative to each other. For example, one or more of the conductive elements 1110, 1120, 1130 and the ferromagnetic components 1140, 1150, 1160, 1170, 1175, 1180, 1185, 1190*a*, 1190*b* may include one or more complementary attachment members (not shown) that are configured to enable attachment (e.g., releasable attachment) of the conductive elements 1110, 1120, 1130 to the ferromagnetic components 1140, 1150, 1160, 1170, 1175, 1180, 1185, 1190*a*, 1190*b*. The one or more attachment members may be configured such that the conductive elements 1110, 1120, 1130 and the ferromagnetic components 1140, 1150, 1160, 1170, 1175, 1180, 1185, 1190*a*, 1190*b* are fixedly supported relative to each other. The one or more attachment members may be configured such that the conductive elements 1110, 1120, 1130 and the ferromagnetic components 1140, 1150, 1160, 1170, 1175, 1180, 1185, 1190*a*, 1190*b* are movable (e.g., repositionable) relative to each other.

When the conductive elements 1110, 1120, 1130 are supported by (e.g., attached to) one or more of the ferromagnetic components 1140, 1150, 1160, 1170, 1175, 1180, 1185, 1190*a*, 1190*b*, the conductive elements 1110, 1120, 1130 may be electrically isolated from the ferromagnetic components 1140, 1150, 1160, 1170, 1175, 1180, 1185, 1190*a*, 1190*b*, for example using a dielectric. The dielectric may be air, and the conductive elements 1110, 1120, 1130 may be spaced from (e.g., not in direct contact with) the ferromagnetic components 1140, 1150, 1160, 1170, 1175, 1180, 1185, 1190*a*, 1190*b* when the conductive elements 1110, 1120, 1130 are attached to the ferromagnetic components 1140, 1150, 1160, 1170, 1175, 1180, 1185, 1190*a*, 1190*b*. The conductive elements 1110, 1120, 1130 may be attached to one or more of the ferromagnetic components 1140, 1150, 1160, 1170, 1175, 1180, 1185, 1190*a*, 1190*b* using one or more attachment members that are made of any suitable electrically isolating (e.g., dielectric) material.

Figure 12:
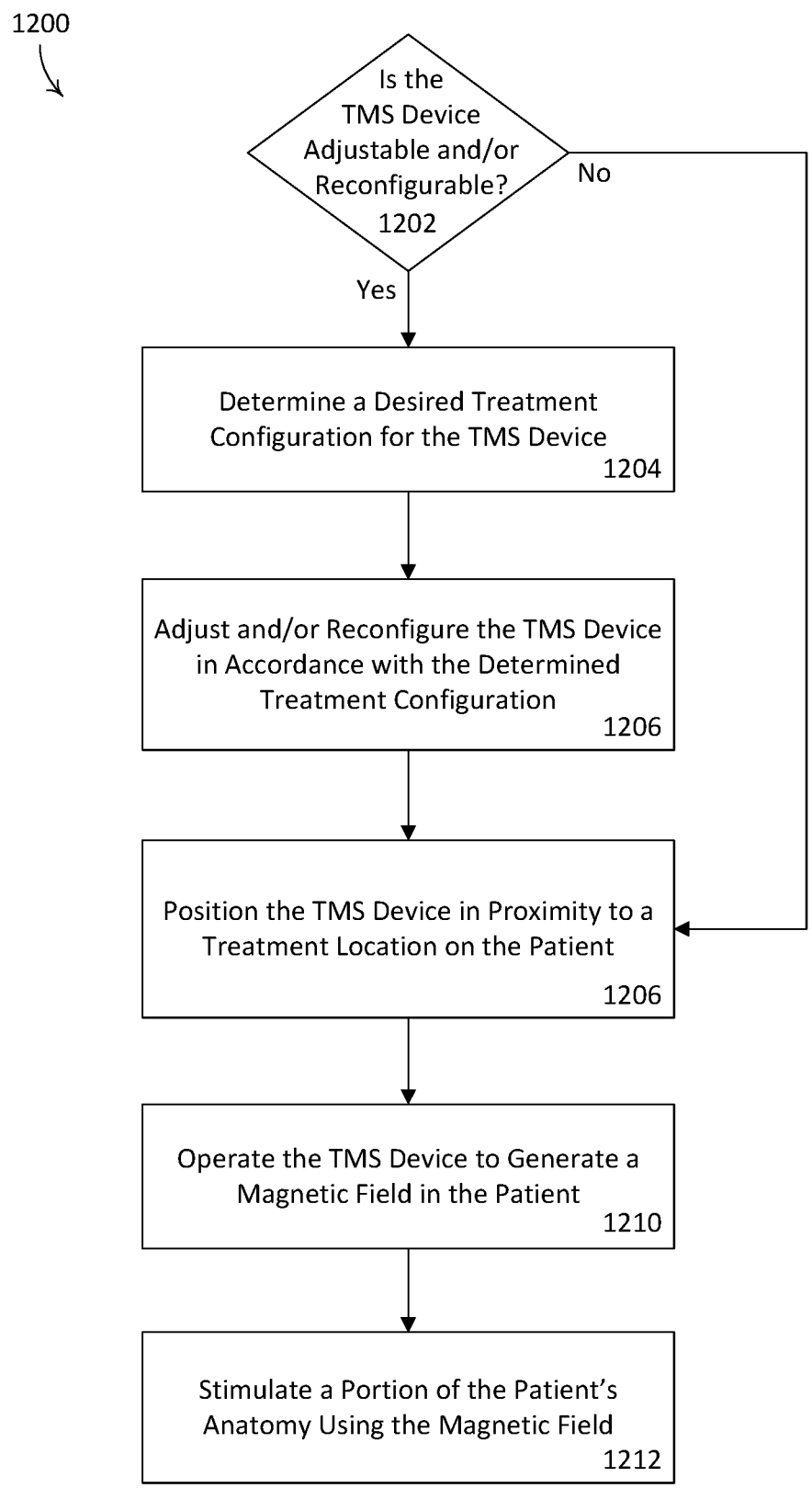
FIG. 12 is a flow diagram of an example TMS treatment process.

FIG. 12 is a flow diagram of an example TMS treatment process 1200. The TMS treatment process 1200 may be performed using a TMS device, such as one of the example TMS devices described herein (e.g., any of the treatment coils 300, 400, 500, 600, 700, 800, 900, 1000, or 1100).

At 1202, a TMS device (e.g., a treatment coil) may be selected for use in the TMS treatment process 1200. The TMS device may have a static configuration (e.g., in accordance with treatment coils 300, 400, 500, 600, 700, 800, 900, 1000, or 1100) or may have an adjustable and/or reconfigurable configuration. If the selected TMS device has a static configuration, the treatment process 1200 may advance to 1208. If the selected TMS device has an adjustable and/or reconfigurable configuration, the treatment process 1200 may advance to 1204.

At 1204, a desired treatment configuration for the TMS device may be determined. This determination may be made based upon the anatomy of the subject at a desired treatment location. For example, the determination may be made in accordance with one or more of a size of the subject's head, a portion of the subject's brain that is to be treated, the particular treatment or diagnostic procedure, and/or the like.

At 1206, the TMS device may be adjusted and/or reconfigured in accordance with the determined treatment configuration. For example, if the TMS device 1100 is selected as the TMS device for the treatment process 1200, the treatment coil may be reconfigured by removing and/or replacing one or more ferromagnetic components (e.g., the eighth and/or ninth ferromagnetic components 1190*a*, 1190*b*). The treatment process 1200 may advance to 1208 when the TMS device has been adjusted and/or reconfigured in accordance with the determined treatment configuration.

At 1208, the TMS device may be positioned in proximity to a desired treatment location on the subject (e.g., proximate to the subject's head). For example, if the TMS device is mounted to a positioning apparatus, the positioning apparatus may be operated such that the one or more treatment coils of the TMS device are disposed near a cutaneous location on the subject's head.

At 1210, the TMS device may be operated to generate a magnetic field in the subject (e.g., in the subject's head). For example, a control circuit that is in electrical communication with the TMS device may be operated to deliver pulses of electrical current to the TMS device. At 1212, the magnetic field generated by the TMS device may be used to stimulate one or more portions of the subject's anatomy (e.g., one or more activation zones within of the subject's brain). In an example, the one or more portions of the subject's brain may be stimulated in accordance with one or more stimulation cycles, with each stimulation cycle including five seconds of stimulation followed by a five second rest period. The stimulation may be performed at a frequency rate of approximately fifteen Hertz (15 Hz), for example.

The treatment process 1200 may include using the TMS device to determine a motor threshold location of the subject. The TMS device may be configured such that localization is not required during the motor threshold location procedure. For example, the TMS device (e.g., any of the treatment coils 300, 400, 500, 600, 700, 800, 900, 1000, or 1100) may be configured to generate a magnetic field in the subject's brain that stimulates a strip shaped region of the subject's brain (e.g., in an anterior-posterior direction) that encompasses the motor threshold location. A motor threshold location may be determined using localization of the TMS device. For example, the TMS device may be moved over an area of the subject's head until an indication of positioning is observed (e.g., until the subject's thumb moves or twitches indicating a motor threshold location). The motor threshold location may be determined, for example, using a stimulation frequency rate of approximately one (1) Hz. From the motor threshold location, the TMS device may be moved to the desired treatment location on the subject. In an example, the desired treatment location may be approximately five centimeters (5 cm) anteriorly from the determined motor threshold location.

TMS devices, such as the example treatment coils described herein (e.g., any of the treatment coils 300, 400, 500, 600, 700, 800, 900, 1000, or 1100), may be used to treat a number of conditions or disorders, for example depression, incontinence, and weight control issues. Such treatments may be applied to a subject, for example, using the example TMS devices in accordance with the example TMS treatment process 1200. The example TMS devices may be used to treat other conditions or disorders. For example, the TMS devices may be used in the rehabilitation of muscles. The TMS devices may be used in the treatment of peripheral nervous system disorders.

The example TMS devices may be used in one or more of the following treatment contexts, including major depressive disorder, epilepsy, schizophrenia, Parkinson's disease, Tourette's syndrome, amyotrophic lateral sclerosis (ALS), multiple sclerosis (MS), Alzheimer's disease, attention deficit/hyperactivity disorder (ADHD), obesity, bipolar disorder and/or mania, anxiety disorders (e.g., panic disorder with and without agoraphobia, social anxiety disorder, acute stress disorder, generalized anxiety disorder), post-traumatic stress disorder (PTSD), obsessive compulsive disorder (OCD), pain (e.g., migraine, trigeminal neuralgia), chronic pain disorders (e.g., pain due to diabetic neuropathy, post-herpetic neuralgia), idiopathic pain disorders (e.g., fibromyalgia, regional myofascial pain syndrome), rehabilitation following stroke (neuro-plasticity induction), tinnitus, stimulation of implanted neurons to facilitate integration, substance-related disorders (e.g., dependence, abuse, and/or withdrawal diagnoses for alcohol, cocaine, amphetamine, caffeine, nicotine, *cannabis*, etc.), spinal cord injury and regeneration and/or rehabilitation, head injury, sleep deprivation reversal, primary sleep disorders (e.g., primary insomnia, primary hypersomnia, or circadian rhythm sleep disorder), cognitive enhancements, dementias, premenstrual dysphoric disorder (PMS), drug delivery systems (e.g., changing cell membrane permeability to a drug), induction of protein synthesis (e.g., induction of transcription and translation), stuttering, aphasia, dysphagia, essential tremor, and eating disorders (e.g., bulimia, anorexia, binge eating).

It should be appreciated that the example TMS devices may be employed for uses other than treatment applications. For example, the example TMS devices may be used (e.g., in accordance with the example TMS treatment process 1200) to perform diagnoses of one or more conditions in a subject. To illustrate, the example TMS devices may be used to diagnose a subject's response to drugs or other therapies, and/or may be used to quantify an effectiveness of such therapies. For example, a pharmaceutical may be known to have effects (e.g., direct or secondary effects) on the performance of the central nervous system. Such effects may be observed using the example TMS devices, for example by providing TMS and observing one or more of evoked potentials, motor response, conduction velocities, or other responses. Observed changes in one or more such response may be used, for example, to quantify a performance of the pharmaceutical or to determine an optimal dosing of the pharmaceutical.

The example TMS devices may be used (e.g., in accordance with the example TMS treatment process 1200) to perform diagnoses of one or more pathologies in a subject, for example by observing neurological response. Such pathologies may include, but are not limited to, degenerative diseases, extent of a traumatic injury, progression of a disease, systemic deficiencies, and congenital anomalies. To illustrate, the example TMS devices may be used in the diagnosis of, for example, compromised motor function, Alzheimer's disease, Parkinson's disease, ALS, MS, diabetic neuropathy, chronic demyelinating neuropathy, acute demyelinating neuropathy, epilepsy, vitamin B12 deficiency (e.g., pernicious anemia), vitamin E deficiency, neurosarcoidosis, tinnitus, and stroke. The example TMS devices may be used to evaluate the efficacy of treatments for such pathologies. For example, the TMS devices may be used to assess and/or measure the effect of pharmaceuticals, for example anti-convulsives, Alzheimer's medications, antipsychotics, pain medications, antianxiety medications, hypnotics (sedatives), analgesics (central), ADHD medications, or anesthetics.

It should be appreciated that the example TMS devices described herein (e.g., any of the treatment coils 300, 400, 500, 600, 700, 800, 900, 1000, or 1100) are not limited to their illustrated configurations. For example, one or more components from a first one of the example TMS devices may be implemented in a second one of the example TMS devices. In an example illustration, the fourth ferromagnetic component 745*a* and/or a fifth ferromagnetic component 745*b* may be added to the treatment coil 500 and/or the treatment coil 600. In another example illustration, the second ferromagnetic component 680 and/or the third ferromagnetic component 690 of the treatment coil 600 may be substituted for the fourth, fifth, sixth, and/or seventh ferromagnetic components 1170, 1175, 1180, 1185 of the treatment coil 1100. One of ordinary skill in the art will appreciate that these and other different configurations of the example TMS devices may be implemented without departing from the scope and spirit of the instant disclosure.

What is claimed is:

1. A system for treating or diagnosing a patient, the system comprising:
    an electromagnet comprising a first conductive winding and a second conductive winding;
    a drive circuit electrically coupled to the electromagnet; and a controller configured to control the drive circuit to provide current to the electromagnet to generate a pulsing magnetic field;

wherein the first conductive winding defines an inner surface and an outer surface, the outer surface comprising a convex portion and a concave portion, wherein the concave portion of the outer surface of the first conductive winding defines a concavity, and wherein at least a portion of the second conductive winding resides within the concavity of the first conductive winding.

2. The system of claim 1, wherein the first conductive winding is crescent shaped.

3. The system of claim 1, wherein the first conductive winding does not encapsulate the second conductive winding.

4. The system of claim 1, wherein the first conductive winding defines a non-circular or non-oval shape.

5. The system of claim 1, wherein, together, the first conductive winding forms a kidney shape.

6. The system of claim 1, wherein the first and second conductive winding are configured at a relative distance to one another such that when the first and second conductive windings are driven they generate at least a first and second independent stimulation zones within a brain of the patient, wherein the stimulation zones each comprise a region of the brain where an induced current is above a depolarization threshold of neurons of the brain.

7. The system of claim 6, wherein the first stimulation zone comprises currents moving in a first direction and the second stimulation zone comprises currents moving in a second, different direction.

8. The system of claim 6, wherein the first and second stimulation zones relate to two different functional regions of the brain.

9. The system of claim 1, wherein the first conductive winding comprises a first number of turns and the second conducive winding comprises a second number of turns, the first and second number of turns being different.

10. The system of claim 1, wherein the electromagnet further comprises a magnetic core.

11. The system of claim 10, wherein the magnetic core comprises a powdered magnetic material, a laminated magnetic material, or an amorphous magnetic material.

12. The system of claim 10, wherein the magnetic core comprises one or more of an alloy of iron, nickel, or cobalt.

13. The system of claim 10, wherein the magnetic core comprises gadolinium, neodymium, or holmium.

14. The system of claim 10, wherein the magnetic core comprises a single ferromagnetic component defining two poles, a first pole defining a substantially circular cross-sectional shape, and a second pole defining a crescent cross-sectional shape.

15. The system of claim 14, wherein the first pole defines a first pole face and the second pole defines a second pole face, the first and second pole faces being non-planar with one another.

16. The system of claim 10, wherein the magnetic core comprises a plurality of ferromagnetic components.

17. A system for treating or diagnosing a patient, the system comprising:

an electromagnet comprising a first conductive winding, a second conductive winding, and a magnetic core;

a drive circuit electrically coupled to the electromagnet; and a controller configured to control the drive circuit to provide current to the electromagnet to generate a pulsing magnetic field;

wherein the first conductive winding defines an inner surface and an outer surface, the outer surface comprising a convex portion and a concave portion, and wherein the second conductive winding resides proximate to the concave portion of the outer surface of the first conductive winding.

18. The system of claim 17, wherein the magnetic core comprises a single ferromagnetic component defining two poles, a first pole defining a substantially circular cross-sectional shape, and a second pole defining a crescent cross-sectional shape.

19. The system of claim 18, wherein the first pole defines a first pole face and the second pole defines a second pole face, the first and second pole faces being non-planar with one another.

20. The system of claim 17, wherein the magnetic core comprises a powdered magnetic material, a laminated magnetic material, or an amorphous magnetic material.

21. The system of claim 17, wherein the first conductive winding is crescent shaped or kidney shaped.

22. The system of claim 17, wherein the first conductive winding defines a non-circular or non-oval shape, and wherein the first conductive winding does not encapsulate the second conductive winding.

23. The system of claim 17, wherein the first conductive winding comprises a first number of turns and the second conducive winding comprises a second number of turns, the first and second number of turns being different.

24. A system for treating or diagnosing a patient, the system comprising:

an electromagnet comprising a first conductive winding and a second conductive winding;

a drive circuit electrically coupled to the electromagnet; and a controller configured to control the drive circuit to provide current to the electromagnet to generate a pulsing magnetic field;

wherein the first conductive winding defines an inner surface and an outer surface, the outer surface comprising a convex portion and a concave portion, wherein the concave portion of the outer surface of the first conductive winding defines a curvature, and wherein a portion of an outer surface of the second conductive winding defines a curvature that is congruent with the curvature of the outer surface of the concave portion of the first conductive winding.

25. The system of claim 24, wherein the portion of the outer surface of the second conductive winding resides within a cavity defined by the outer surface of the concave portion of the first conductive winding.

26. The system of claim 24, wherein the second conductive winding resides proximate to the concave portion of the outer surface of the first conductive winding.

27. The system of claim 24, wherein the first conductive winding is crescent shaped or kidney shaped.

28. The system of claim 24, wherein the first conductive winding defines a non-circular or non-oval shape, and wherein the first conductive winding does not encapsulate the second conductive winding.

29. The system of claim 24, wherein the electromagnet further comprises a magnetic core.

* * * * *